US011826408B2

(12) United States Patent
Olin

(10) Patent No.: US 11,826,408 B2
(45) Date of Patent: *Nov. 28, 2023

(54) CD200 INHIBITORS AND METHODS OF USE THEREOF

(71) Applicant: REGENTS OF THE UNIVERSITY OF MINNESOTA, Minneapolis, MN (US)

(72) Inventor: Michael Olin, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 302 days.

This patent is subject to a terminal disclaimer.

(21) Appl. No.: 17/114,193

(22) Filed: Dec. 7, 2020

(65) Prior Publication Data

US 2021/0106665 A1    Apr. 15, 2021

Related U.S. Application Data

(62) Division of application No. 15/773,527, filed as application No. PCT/US2016/060164 on Nov. 2, 2016, now Pat. No. 10,888,609.

(60) Provisional application No. 62/250,376, filed on Nov. 3, 2015.

(51) Int. Cl.
| | | |
|---|---|---|
| *A61K 39/00* | (2006.01) | |
| *A61K 39/39* | (2006.01) | |
| *C07K 7/06* | (2006.01) | |
| *C07K 7/08* | (2006.01) | |
| *C07K 14/705* | (2006.01) | |
| *A61P 35/02* | (2006.01) | |
| *A61K 9/00* | (2006.01) | |
| *A61K 31/203* | (2006.01) | |
| *A61K 31/404* | (2006.01) | |
| *A61K 31/675* | (2006.01) | |
| *A61K 31/7068* | (2006.01) | |
| *A61K 38/20* | (2006.01) | |

(52) U.S. Cl.
CPC ........ *A61K 39/0011* (2013.01); *A61K 9/0019* (2013.01); *A61K 39/39* (2013.01); *A61P 35/02* (2018.01); *C07K 7/06* (2013.01); *C07K 7/08* (2013.01); *C07K 14/70503* (2013.01); *A61K 31/203* (2013.01); *A61K 31/404* (2013.01); *A61K 31/675* (2013.01); *A61K 31/7068* (2013.01); *A61K 38/2013* (2013.01); *A61K 2039/545* (2013.01); *A61K 2039/55516* (2013.01); *A61K 2039/55561* (2013.01); *A61K 2039/585* (2013.01); *A61K 2039/6081* (2013.01); *A61K 2039/80* (2018.08); *A61K 2300/00* (2013.01)

(58) Field of Classification Search
CPC .. A61K 39/0011; A61K 9/0019; A61K 39/39; A61K 2039/545; A61K 2300/00; C07K 7/08

See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,683,202 | A | 7/1987 | Mullis |
| 4,820,508 | A | 4/1989 | Wortzman |
| 4,873,192 | A | 10/1989 | Kunkel |
| 4,938,949 | A | 7/1990 | Borch et al. |
| 4,992,478 | A | 2/1991 | Geria |
| 5,350,674 | A | 9/1994 | Boenisch et al. |
| 5,585,362 | A | 12/1996 | Schwarz et al. |
| 5,744,585 | A | 4/1998 | Medenica et al. |
| 5,928,906 | A | 7/1999 | Koster et al. |
| 6,955,811 | B2 | 10/2005 | Gorczynski et al. |
| 7,205,386 | B2 | 4/2007 | Gorczynski |
| 7,902,151 | B2 | 3/2011 | Gorczynski et al. |
| 8,709,415 | B2 | 4/2014 | Bowdish et al. |
| 9,737,598 | B2 | 8/2017 | Olin et al. |
| 10,888,609 | B2 | 1/2021 | Olin |
| 2002/0168364 | A1 | 11/2002 | Gorczynski et al. |
| 2010/0291085 | A1 | 11/2010 | Rother et al. |
| 2016/0166680 | A1 | 6/2016 | Olin |

FOREIGN PATENT DOCUMENTS

| | | |
|---|---|---|
| WO | 2012048190 A1 | 4/2012 |
| WO | 2013076374 A1 | 5/2013 |

OTHER PUBLICATIONS

Moertel et al J Immunother Cancer, 2: 46, online published Dec. 16, 2014, IDS, #39, filed Mar. 30, 2021 (Year: 2014).*
Ali, S. , et al., "Combined immunostimulation and conditional cytotoxic gene therapy provide long-term survival in a large glioma model", Cancer Res 65(16), 7194-7204 (2005).
Anandkumar , et al., "Tumour immunomodulation: mucins in resistance to initiation and maturation of immune response against tumours", Scand J Immunol 78(1), 1-7 (2013).
Callahan, MK , et al., "At the bedside: CTLA-4- and PD-1-blocking antibodies in cancer immunotherapy", J Leukoc Biol 94(1), 41-53 (2013).
Candolfi, M., et al., "Release of HMGB1 in response to proapoptotic glioma killing strategies: efficacy and neurotoxicity", Clin Cancer Res 15(13), 4401-4414 (2009).
Chen, D , et al., "Synthetic peptides from the N-terminal regions of CD200 and CD200R1 modulate immunosuppressive and anti-inflammatory effects of CD200-CD200R1 interaction", International Immunology 17(3), 289-296 (2005).

(Continued)

*Primary Examiner* — Lei Yao
(74) *Attorney, Agent, or Firm* — Viksnins Harris Padys Malen LLP

(57) ABSTRACT

The present invention provides in certain embodiments compositions comprising at least one CD200 inhibitor, and methods of reversing or modulating immune suppression in a patient having a disease or disorder arising from abnormal cell growth, function or behavior, which method comprises administering to a patient in need thereof a CD200 inhibitor composition.

22 Claims, 39 Drawing Sheets

Specification includes a Sequence Listing.

(56) References Cited

OTHER PUBLICATIONS

Chitnis, T., et al., "Elevated neuronal expression of CD200 protects Wlds mice from inflammation-mediated neurodegeneration", Am J Pathol 170(5), 1695-1712 (2007).
Curran, MA, et al., "PD-1 and CTLA-4 combination blockade expands infiltrating T cells and reduces regulatory T and myeloid cells within B16 melanoma tumors", Proc Natl Acad Sci 107(9), 4275-4280 (2010).
Curtin, JF, et al., "Fms-like tyrosine kinase 3 ligand recruits plasmacytoid dendritic cells to the brain", J Immunol 176(6), 3566-3577 (2006).
Curtin, JF, et al., "HMGB1 mediates endogenous TLR2 activation and brain tumor regression", PLoS Med 6(1), e10, (2009).
Curtin, JF, et al., "Treg depletion inhibits efficacy of cancer immunotherapy: implications for clinical trials", PLoS One 3(4), e1983 (2008).
Donson, AM, et al., "Immune gene and cell enrichment is associated with a good prognosis in ependymoma", J Immunol 183(11), 7428-7440 (2009).
Forde, PM, et al., "New strategies in lung cancer: epigenetic therapy for non-small cell lung cancer", Clin Cancer Res 20(9), 2244-2248 (2014).
Ghulam, Muhammad Ak, et al., "Antiglioma immunological memory in response to conditional cytotoxic/immune-stimulatory gene therapy: humoral and cellular immunity lead to tumor regression", Clin Cancer Res 15(19), 6113-6127 (2009).
Gorczynski, et al., "Augmented Induction of CD4+CD25+ Treg using monoclonal antibodies to CD200R", Transplantation 79(9), 1180-1183 (2005).
Gorczynski, R., et al., "CD200 is a ligand for all members of the CD200R family of immunoregulatory molecules", J Immunol 172 (12), 7744-7749 (2004).
Gorczynski, Reg, et al., "Peptides of CD200 Modulate LPS-Induced TNF-alpha induction and mortality in vivo", Journal of Surgical Research 145, 87-96 (2008).
Gorczynski, et al., "Receptor engagement on cells expressing a ligand for the tolerance-inducing molecule OX2 induces an immunoregulatory population that inhibits alloreactivity in vitro and in vivo", J Immunol 165 (9), 4854-4860 (2000).
Gorczynski, R.M., "Review Article, CD200:CD200R-Mediated Regulation of Immunity", International Scholarly Research Network, ISRN Immunology, vol. 2012, Article ID 682168, 18 pages (2012).
Gorczynski, et al., "Structural and functional heterogeneity in the CD200R family of immunoregulatory molecules and their expression at the feto-maternal interface", Am J Reprod Immunol 52(2), 147-163 (2004).
Hoek, RM, et al., "Down-regulation of the macrophage lineage through interaction with OX2 (CD200)", Science 290(5497), 1768-1771 (2000).
Hoffman, LM, et al., "Molecular sub-group-specific immunophenotypic changes are associated with outcome in recurrent posterior fossa ependymoma", Acta Neuropathol 127(5), 731,745 (2014).
Holmannova, et al., "CD200/CD200R paired potent inhibitory molecules regulating immune and inflammatory responses; Part I: CD200/CD200R structure, activation, and function", Acta Medica 55(1), 12-7 (2012).
Inaba, K, et al., "Generation of large Nos. of dendritic cells from mouse bone marrow cultures supplemented with granulocyte/macrophage colony-stimulating factor", J Exp Med 176(6), 1693-1702 (1992).
Janne, PA, "Ongoing first-line studies of epidermal growth factor receptor tyrosine kinase inhibitors in select patient populations", Semin Oncol. 32 (6 Suppl 10), S9-15 (2005).
Kawasaki, BT, et al., "Co-expression of the toleragenic glycoprotein, CD200, with markers for cancer stem cells", Biochem Biophys Res Commun 364(4), 778-782 (2007).
Kerkar, SP, et al., "Cellular constituents of immune escape within the tumor microenvironment", Cancer Res 72(13), 3125-3130 (2012).

King, GD, et al., "Flt3L and TK gene therapy eradicate multifocal glioma in a syngeneic glioblastoma model", Neuro Oncol 10(1), 19-31 (2008).
Kirkwood, JM, et al., "Immunotherapy of cancer in 2012", Cancer J Clin 62(5), 309-335 (2012).
Kong, S, et al., "Suppression of human glioma xenografts with second-generation IL13R-specific chimeric antigen receptor-modified T cells", Clin Cancer Res 18(21), 5949-5960 (2012).
Koning, N, et al., "Distribution of the immune inhibitory molecules CD200 and CD200R in the normal central nervous system and multiple sclerosis lesions suggests neuron-glia and glia-glia interactions", J Neuropathol Exp Neurol 68(2), 159-167 (2009).
Koning, N., et al., "Downregulation of macrophage inhibitory molecules in multiple sclerosis lesions", Ann Neurol 62 (5), 504-514 (2007).
Kretz-Rommel, Anke, et al., "Blockade of CD200 in the Presence or Absence of Antibody Effector Function: Implications for Anti-CD200 Therapy", Journal of Immunology 180 (2), 699-705 (2008).
Kunkel, T, "Rapid and efficient site specific mutagenesis without phenotypic selection", Proc. Natl Acad Sci vol. 82, 488-492 (1985).
Kunkel, T, et al., "Rapid and Efficient Site-Specific Mutagenesis without Phenotypic Selection", Meth Enzymol 154, 367-382 (1987).
Li, Y, et al., "Aberrant CD200/CD200R1 expression and function in systemic lupus erythematosus contributes to abnormal T-cell responsiveness and dendritic cell activity", Arthritis Res Ther 14 (3), R123 (2012).
Mantovani, A., et al., "Tumor-associated macrophages and the related myeloid-derived suppressor cells as a paradigm of the diversity of macrophage activation", Hum Immunol 70(5), 325-330 (2009).
McGhee, J, et al., "New Perspectives in Mucosal Immunity with Emphasis on Vaccine Development", Seminars in Hematology, vol. 30 (4), Suppl 4, 3-15 (1993).
Mesias, E, et al., "Use of CD200 blockade inhibitor to enhance glioma immunotherapy", Journal Immunotherapy of Cancer 3(2), P38 (2015).
Moertel, CL, et al., "CD200 in CNS tumor-induced immunosuppression: the role for CD200 pathway blockade in targeted immunotherapy", J Immunother Cancer 2(1), 46, 10 pages (2014).
Murdoch, C., et al., "The role of myeloid cells in the promotion of tumour angiogenesis", Nat Rev Cancer 8, 618-631 (2008).
Ohlfest, Jr, et al., "Vaccine injection site matters: qualitative and quantitative defects in CD8 T cells primed as a function of proximity to the tumor in a murine glioma model", J Immunol 190(2), 613-620 (2013).
Okada, H., et al., "Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in p", J Clin Oncol 29(3), 330-336 (2011).
Olin, MR, et al., "Oxygen is a master regulator of the immunogenicity of primary human glioma cells", Cancer Res 71 (21), 6583-6589 (2011).
Olin, MR, et al., "Superior efficacy of tumor cell vaccines grown in physiologic oxygen", Clin Cancer Res 16(19), 4800-4808 (2010).
Olin, M., et al., "Vaccination with dendritic cells loaded with allogeneic brain tumor cells for recurrent malignant brain tumors induces a CD4(+)IL17(+) response", J Immunother Cancer 2, 4 (2014).
Patent Cooperation Treaty, International Searching Authority, Search Report and Written Opinon for PCT/US2016/060164, 10 pages, dated Feb. 21, 2017.
Petermann, KB, et al., "CD200 is induced by ERK and is a potential therapeutic target in melanoma", J Clin Invest 117 (12), 3922-3929 (2007).
Prins, RM, et al., "Gene expression profile correlates with T-cell infiltration and relative survival in glioblastoma patients vaccinated with dendritic cell immunotherapy", Clin Cancer Res 17(6), 1603-1615 (2011).
Puntel, M., et al., "Gene transfer into rat brain using adenoviral vectors", Curr Protoc Neurosci Chapt 4, Unit 4.24 (2010).

(56) References Cited

OTHER PUBLICATIONS

Ramaswamy, V., et al., "Recurrence patterns across medulloblastoma subgroups: an integrated clinical and molecular analysis", Lancet Oncol 14(12), 1200-1207 (2013).
Schroeder, K., et al., "Children are not just little adults: recent advances in understanding of diffuse intrinsic pontine glioma biology", Pediatric Research 75, 205-209 (2013).
Southgaie, T., et al., "Gene transfer into neural cells in vitro using adenoviral vectors", Curr Protoc Neurosci, Chapter 4, Unit 4.23 (2008).
Stupp, R., et al., "Effects of radiotherapy with concomitant and adjuvant temozolomide versus radiotherapy alone on survival in glioblastoma in a randomised phase III study: 5-year analysis of the EORTC-NCIC trial", Lancet Oncol 10(5), 459-466 (2009).
Stupp, R., et al., "Radiotherapy plus concomitant and adjuvant temozolomide for glioblastoma", N Engl J Med 352, 987-996 (2005).
Walker, DG, et al., "Decreased expression of CD200 and CD200 receptor in Alzheimer's disease: a potential mechanism leading to chronic inflammation", Exp Neurol 215(1), 5-19 (2009).
Weber, J., "Immune checkpoint proteins: a new therapeutic paradigm for cancer—preclinical background: CTLA-4 and PD-1 blockade", Semin Oncol 37(5), 430-439 (2010).
Wick, DA, et al., "Profound CD8+ T cell immunity elicited by sequential daily immunization with exogenous antigen plus the TLR3 agonist poly(I:C)", Vaccine 29 (5), 984-993 (2011).
Witt, H., et al., "Delineation of two clinically and molecularly distinct subgroups of posterior fossa ependymoma", Cancer Cell 20(2), 143-157 (2011).
Wong, KK, et al., "Soluble CD200 is critical to engraft chronic lymphocytic leukemia cells in immunocompromised mice", Cancer Res 72(19), 4931-4943 (2012).
Wright, et al., "Characterization of the CD200 receptor family in mice and humans and their interactions with CD200", J Immunol 171(6), 3034-3046 (2003).
Xiong, Z., et al., "Effective CpG immunotherapy of breast carcinoma prevents but fails to eradicate established brain metastasis", Clin Cancer Res 14(17), 5484-5493 (2008).
Xiong, Z, et al., "Tumor-derived vaccines containing CD200 inhibit immune activation: implications for immunotherapy", Immunotherapy 8(9), 1059-1071 (2016).

* cited by examiner

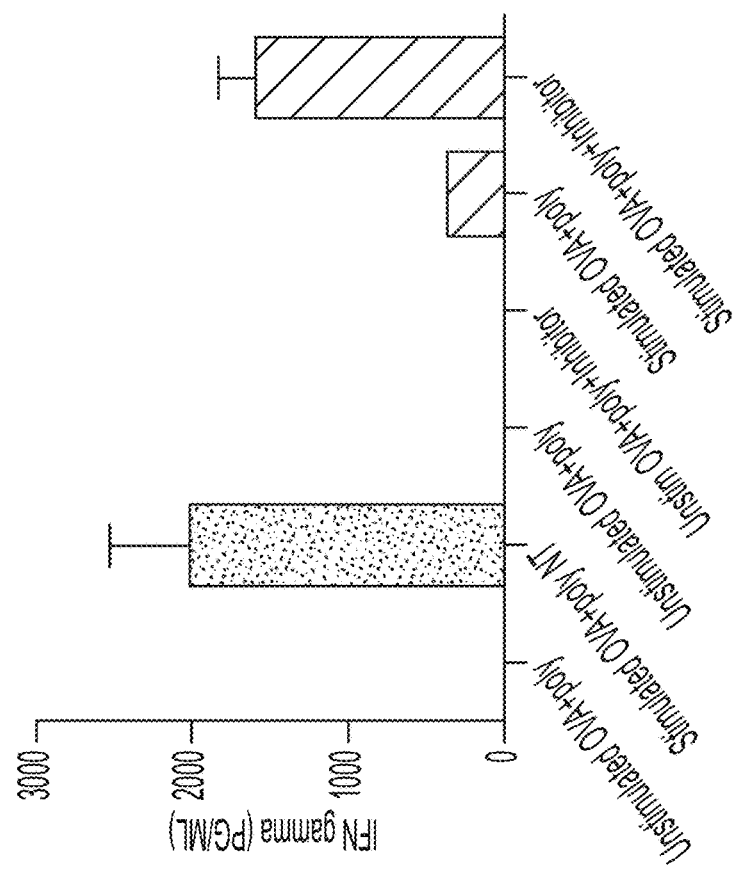
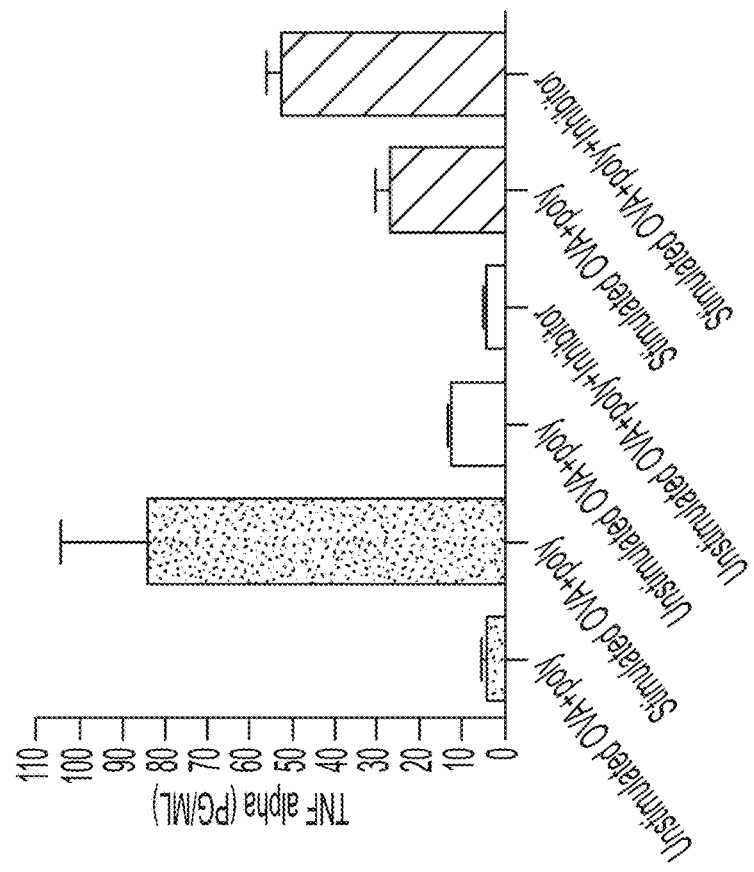
Re-stimulation
Figure 4A
Figure 4B

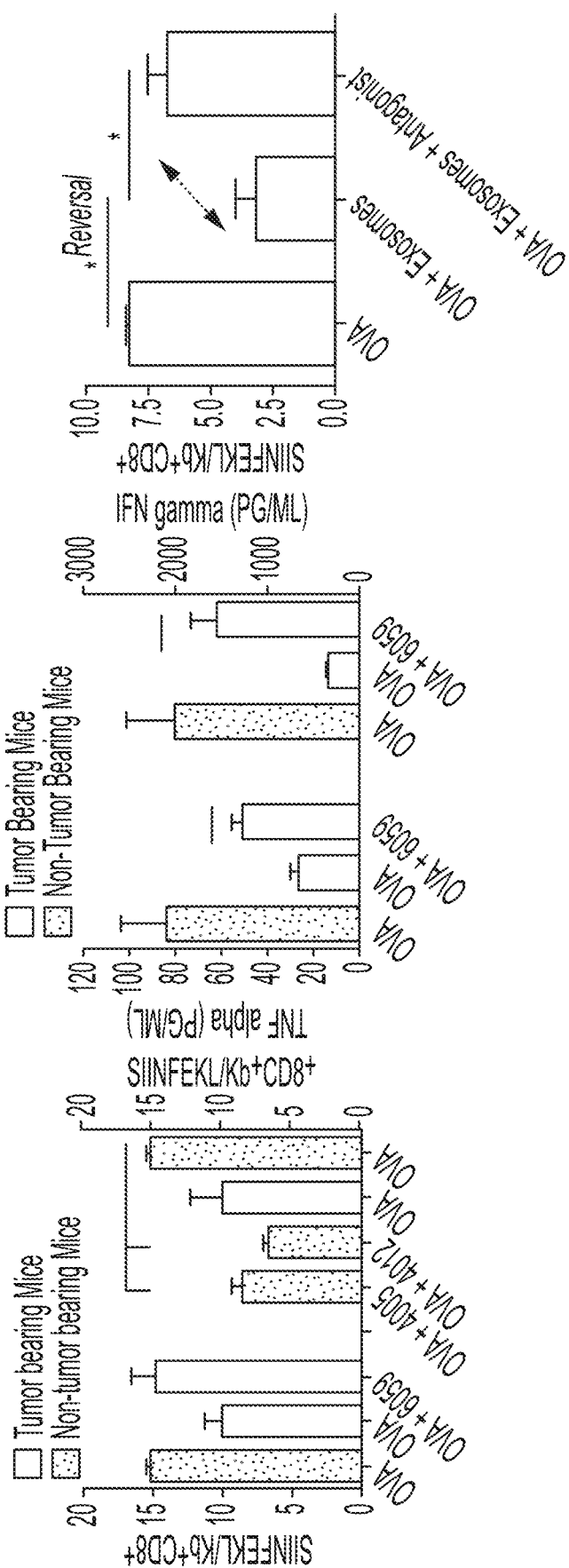
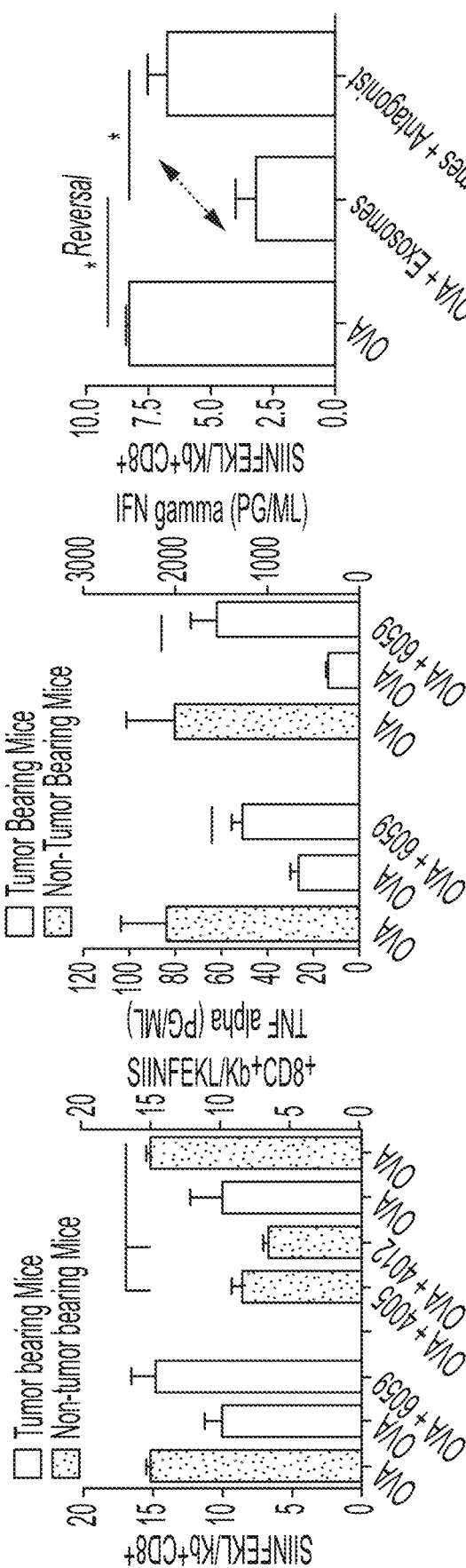
Figure 12A
Figure 12B
Figure 12C

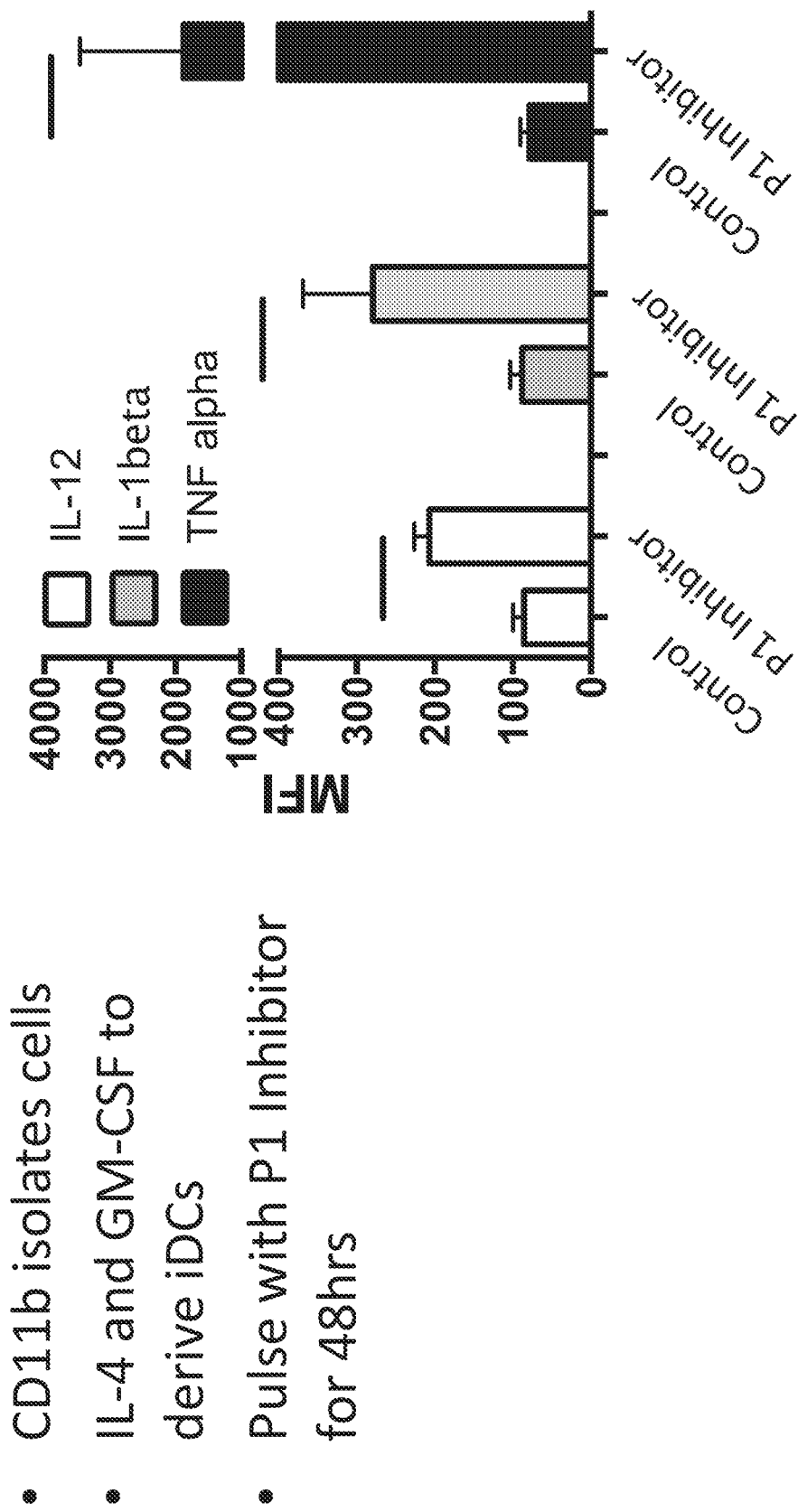

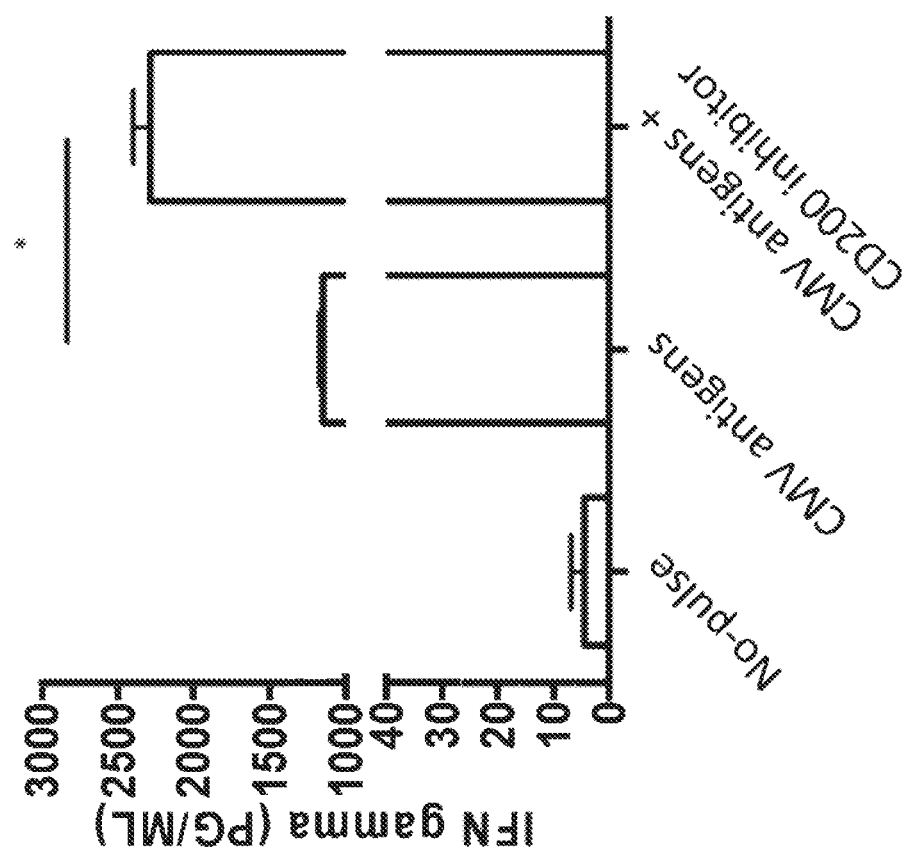

Tumor regression

- Dogs exhibit Flu like symptoms
- Increased lymphocyte infiltration

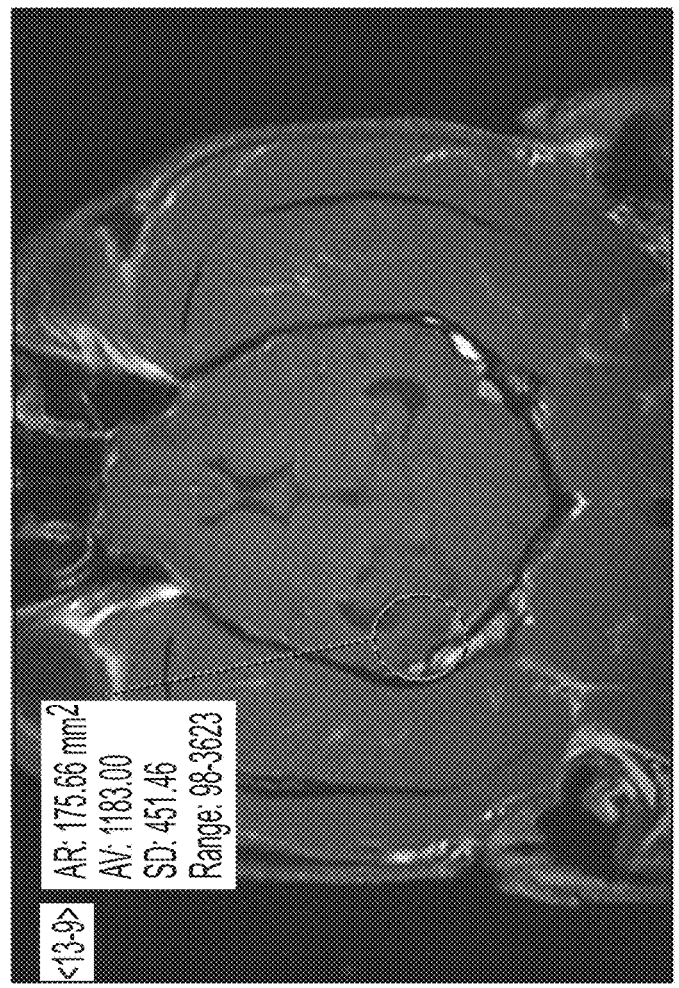
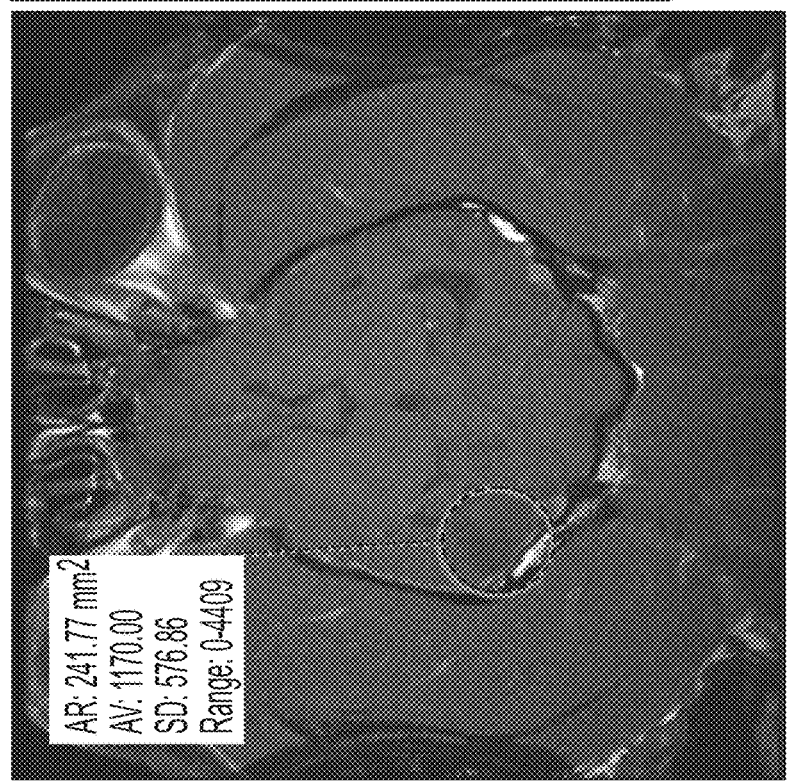
Tumor regression
Figure 17C
Figure 17D

Experimental Model

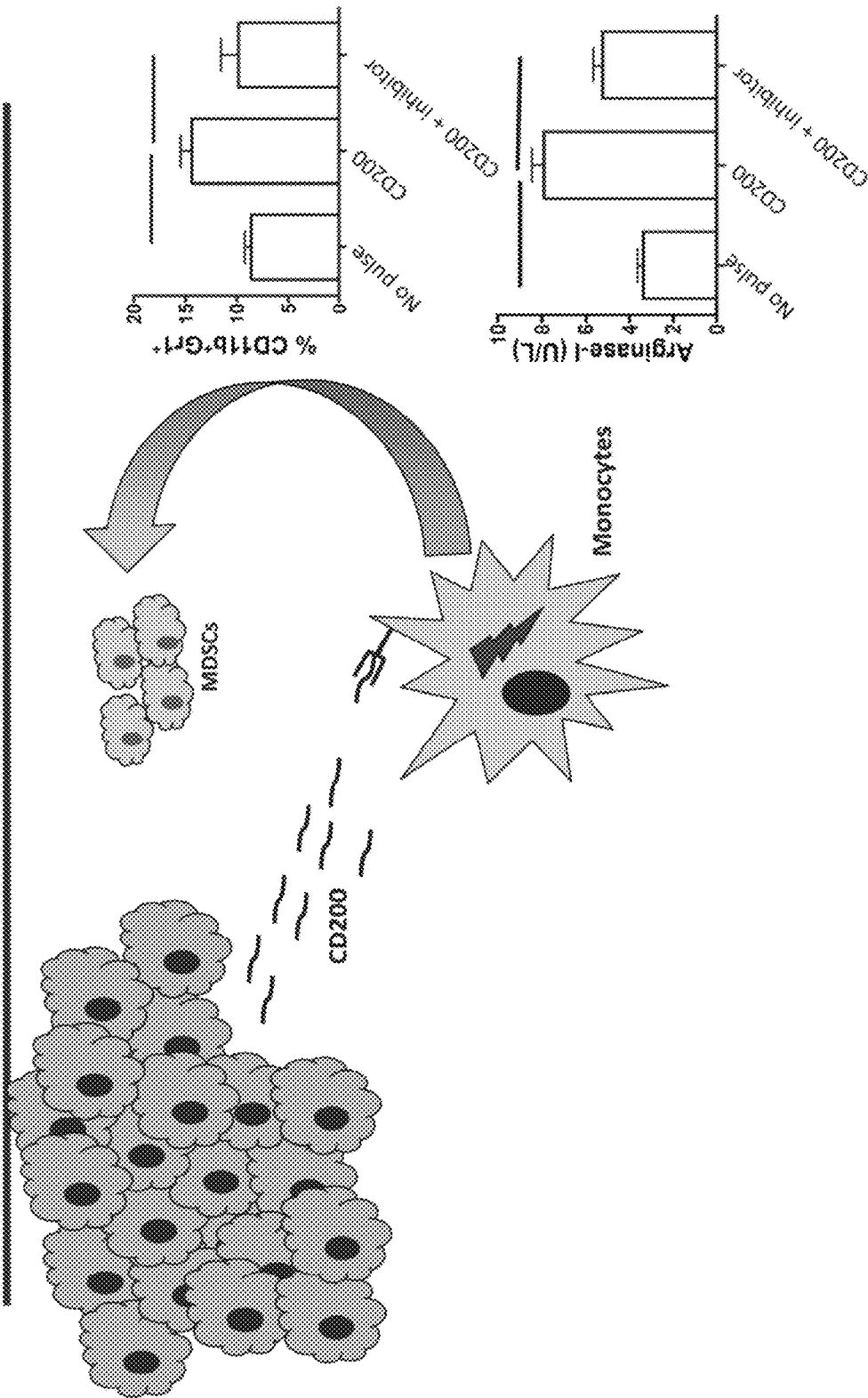

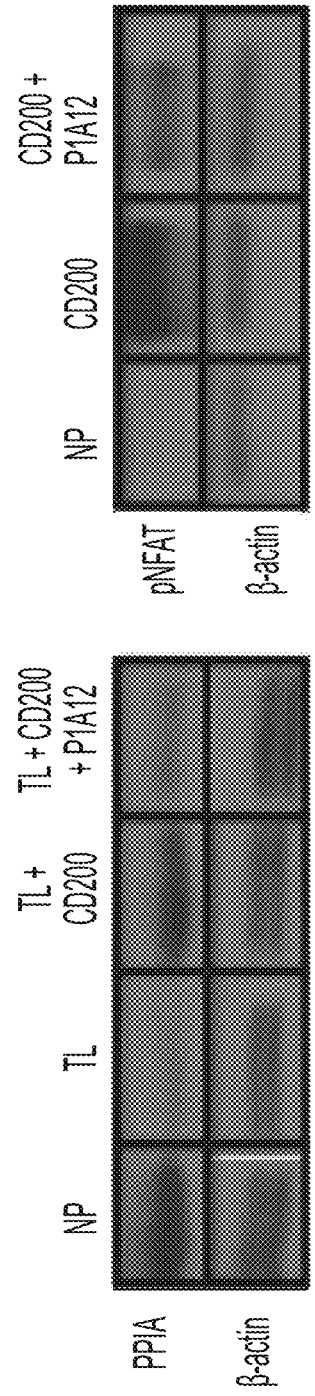

CD200R antagonist Enhances Chemotaxis

Tumor lysate + CpG + Antagonist (24 hrs)

SEQUENCE LISTING

```
<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Thr Ile Gly Asp Gly Gly Cys Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Cys Ser Leu Lys Thr Ser Gln Glu
1               5
```

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Ala Ser Leu Arg Cys Ser Leu Lys Thr Ser Gln Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Phe Asn Thr Phe Gly Ser Gln Lys Val Ser Gly Thr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gln Lys Val Ser Gly Thr Ala Cys Leu Thr Leu Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Pro Glu Asn Met Val Thr Tyr Ser Lys Thr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Tyr Ser Lys Thr His Gly Val Val Thr Gln
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Val Thr Trp Gln Lys Lys Ala Val Ser Pro Glu Asn
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Thr Trp Gln Lys Lys Ala Val Ser Pro Ala Asn
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Ile Thr Leu Glu Asp Glu Gly Cys Tyr Met Cys Leu Phe Asn
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Thr Phe Ser Glu Asn His Gly Val Val Ile Gln Pro Ala Tyr
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Leu Phe Asn Thr Phe Gly Phe Gly Lys Ile Ser Gly Thr Ala
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Lys Val Ser Ala Thr Ala Cys Leu Thr Leu Tyr
1               5                   10

<210> SEQ ID NO 14
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Thr Trp Gln Lys Val Lys Pro Val Ser Leu Glu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Thr Thr Leu Glu Asp Glu Gly Cys Tyr Lys Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Phe Asn Thr Phe Gly Ser Gly Lys Ile Ser Gly
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Ala Ser Leu Arg Cys Ser Leu Gln Asn Pro Glu
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ile Ile Asn Phe Glu Lys Leu
1               5

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Ser Gln Leu Glu Gln Leu Glu Ser Ile Ile Asn Phe Glu Lys
```

```
1               5               10              15
Leu Thr Glu Glu Trp Thr Ser Ser Asn Val Met
                20              25

<210> SEQ ID NO 20
<211> LENGTH: 9
<212> TYPE: PRT
<213> ORGANISM: Cytomegalovirus

<400> SEQUENCE: 20

Asn Leu Val Pro Met Val Ala Thr Val
1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Thr Trp Gln Lys Lys Ala Ala Val Ser Pro Glu Asn
1               5                   10
```

CD200 INHIBITORS AND METHODS OF USE THEREOF

RELATED APPLICATIONS

This application is a divisional of U.S. patent application Ser. No. 15/773,527, filed May 3, 2018, which is a 35 U.S.C. § 371 application of International Application Serial No. PCT/US2016/060164, filed Nov. 2, 2016; which claims the benefit of U.S. Provisional Application Ser. No. 62/250,376, filed Nov. 3, 2015. The entire content of the applications referenced above are hereby incorporated by reference herein.

SEQUENCE LISTING

The instant application contains a Sequence Listing which has been submitted in ASCII format via EFS-Web and is hereby incorporated by reference in its entirety. Said ASCII copy, created on Jun. 30, 2020, is named 09531_368US1_SL.txt and is 5,645 bytes in size.

BACKGROUND OF THE INVENTION

Despite advances in cancer research, there are still no adequate treatments for many cancers. For example, malignant glioma is a devastating disease that arises in over 14,000 patients a year in the United States. Due to the ability of glioma cells to migrate several centimeters from the bulk tumor cavity, current standard of care only results in marginal improvements, with a 5-year survival below 30%. Patients with glioblastoma exhibit systemic immune suppression resulting in deficient adaptive immune responses. These deficiencies' are due to the enriched immunosuppressive factors secreted by the tumor suppressing T cell proliferation and cytotoxic function. Immunosuppression plays an important role in tumor progression in patients with glioblastoma. If the immune suppression could be reversed allowing an effective immune targeting, then patients with glioma will have less tumor progression and improved outcomes.

Accordingly, new compositions and methods to treat cancer are needed. In particular, new compositions that reverse the immunologically suppressed microenvironment caused by tumors are needed.

SUMMARY OF THE INVENTION

The present invention provides a composition comprising at least one CD200 inhibitor. In certain embodiments, the composition further comprises a cancer vaccine. In certain embodiments, the cancer vaccine is a tumor lysate. In certain embodiments, the tumor lysate is substantially devoid of CD200. As used herein "substantially devoid" means that the substance (e.g., tumor lysate) has a diminished level of CD200, e.g., between 1-100% less CD200 than an unprocessed substance. In certain embodiments, the CD200 is removed by absorption using standard methods. In certain embodiments, the CD200 inhibitor is a peptide that has a length of 5 to 20 amino acids. In certain embodiments, the peptide is a non-naturally occurring peptide. In certain embodiments, the peptide comprises one or more mutations (e.g., an alanine substitution), as compared to a naturally occurring peptide derived from a CD200 domain. In certain embodiments, the peptide has the amino acid sequence of SEQ ID NO:1, SEQ ID NO:2, SEQ ID NO:3, SEQ ID NO:4, SEQ ID NO:5, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17. In certain embodiments, the at least one CD200 inhibitor is a peptidomimetic. In certain embodiments, the peptidomimetic comprises one or more D-isomer amino acids. In certain embodiments, the peptidomimetic comprises one or more unnatural amino acids. In certain embodiments, the at least one CD200 inhibitor is an antibody.

The present invention in certain embodiments provides a pharmaceutical composition that comprises a pharmaceutically acceptable carrier or diluent and, as an active ingredient, at least one CD200 inhibitor, and optionally a cancer vaccine (e.g., a tumor lysate) as described above. In certain embodiments, the pharmaceutical composition is formulated for oral administration or injection. In certain embodiments, the pharmaceutical composition is used in a method of treatment of a human or animal body for therapy. In certain embodiments, the composition further comprises a cancer therapy.

The present invention in certain embodiments provides a use of a pharmaceutical composition which that comprises a pharmaceutically acceptable carrier or diluent and, as an active ingredient, at least one CD200 inhibitor, and optionally a cancer vaccine (e.g., a tumor lysate) as defined above for use or in the manufacture of a medicament for treating a disease or disorder arising from abnormal cell growth, function or behavior. In certain embodiments, the disease or disorder is cancer. In certain embodiments, the cancer is selected from solid tumors of the colon, breast, brain, liver, ovarian, gastric, lung, and head and neck. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention in certain embodiments provides a method of treating a disease or disorder arising from abnormal cell growth, function or behavior, which method comprises administering to a patient in need thereof a therapeutic regimen comprising at least one CD200 inhibitor and a cancer vaccine (e.g., a tumor lysate) administered sequentially. In certain embodiments, the therapeutic regimen is administered at least twice. In certain embodiments, the administration comprises administering at least three doses of the therapeutic regimen. In certain embodiments, the administration comprises administering at least five doses of the therapeutic regimen. In certain embodiments, the administration comprises administering at least ten doses of the therapeutic regimen. In certain embodiments, at least two consecutive dosages of the administration are separated by an interval of about one week, or about one month. In certain embodiments, the method further comprises administering an adjuvant before, concurrently or after administration of the therapeutic regimen.

In certain embodiments, the present invention comprises a method of reversing or modulating immune suppression in a patient having a disease or disorder arising from abnormal cell growth, function or behavior, which method comprises administering to a patient in need thereof the composition or therapeutic regimen described above.

In certain embodiments, the present invention comprises a method of reversing or modulating immune suppression in a tumor microenvironment or sentinel lymph nodes in a patient having a disease or disorder arising from abnormal cell growth, function or behavior, which method comprises administering to a patient in need thereof the composition or therapeutic regimen described above. In certain embodiments, the disease or disorder is cancer. In certain embodiments, the cancer is selected from glioblastoma, melanoma, prostate, endometrial, ovarian, breast, lung, head and neck, hepatocellular, and thyroid cancers.

In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

In certain embodiments, the present invention provides a method, wherein the delivering comprises administering the composition to the animal intravenously.

In certain embodiments, the present invention provides a method wherein the composition is administered to the animal using a systemic pump.

In certain embodiments, the present invention further provides administering a chemotherapy agent. In certain embodiments, the chemotherapy agent is sunititib, ontak, cyclophosphamide, gemcitabine, and/or retionoic acid.

In certain embodiments, the animal is a human.

In certain embodiments, the present invention provides process for producing a pharmaceutical composition comprising combining in the composition described above with a pharmaceutically acceptable carrier.

In certain embodiments, the present invention provides a kit for treating cancer, comprising (a) a first pharmaceutical composition comprising a composition described above; and (b) instructions for use.

In certain embodiments, the present invention provides a nucleic acid molecule encoding a CD200 inhibitor, wherein the CD200 inhibitor is a peptide.

In certain embodiments, the present invention provides an expression cassette comprising a nucleic acid molecule encoding a CD200 inhibitor, wherein the inhibitor is a peptide. In certain embodiments, the expression cassette further comprises a promoter.

In certain embodiments, the present invention provides a viral vector comprising the expression cassette described above. In certain embodiments, the vector is an adenovirus (Ad), such as Ad5.

BRIEF DESCRIPTION OF DRAWINGS

FIG. 2C) Purified CD11b cells were pulsed with CD200 inhibitor (P1A12); RNA was analyzed by NanoSight for 575 immune related genes. FIG. 2D). To determine if the CD200 inhibitor dictates the suppressive CD200 protein, we compared results from three groups treated with: CD200 inhibitor (white bar), CD200 protein (red bar), and CD200 protein+CD200 inhibitor (blue bar). Each treatment group was normalized to non-pulsed controls.

FIG. 3A) Vaccination scheme. FIG. 3B) Tumor bearing or non-tumor bearing mice were vaccinated on day 2 and 8 with an agonist (4012) or CD200 inhibitor (6059) only, and on days 3-6 and 10 g with OVA+Poly:ICLC+/−the agonist (4012) or CD200 inhibitor (6059). B) Mice were bled on day 10, whole blood was stained with an anti-CD8 and SIINFEKL specific detramer (SEQ ID NO: 18), lysed and analyzed by flow cytometry. This experiment demonstrated that the competitive inhibitor reversed the suppressive effects of the tumor microenvironment.

FIGS. 4A-4B. Tumor bearing or non-tumor bearing mice were vaccinated on day 2 and 8 with an agonist or CD200 inhibitor only, and on days 3-6 and 10 with OVA+Poly:ICLC+/−the CD200 inhibitor 6059. On day 10, were harvested and stimulated with OVA protein to measure a recall response via cytokine release. FIG. 4A) TNF alpha (PG/ML) levels from tumor bearing mice. FIG. 4B) IFN gamma (PG/ML) levels in tumor bearing mice. This experiment demonstrated that the competitive inhibitor reversed the suppressive effects of the tumor microenvironment.

FIG. 5A) GL261 tumor bearing mice were inoculated with 50 μg of CD200 inhibitor 6059 one day prior to vaccination with tumor lysate (65 μg)+/−the CD200 inhibitor (50 μg). FIG. 5B) Mice were imaged weekly for tumor growth. The following groups were studied: saline (1), tumor lysate (2), and tumor lysate+CD200 inhibitor (6059) (3). FIG. 5C) Percent survival post inoculation for saline (1), tumor lysate (2), and tumor lysate+CD200 inhibitor (3) groups. This experiment demonstrated that the use of our competitive inhibitor slowed tumor growth enhancing survival by 30%.

FIG. 6A) GL261 tumor bearing mice were inoculated with 10 μg of CD200 inhibitor on day 2 into the tumor site then with 50 μg of CD200 inhibitor one day prior to vaccination with tumor lysate (65 μg)+the CD200 inhibitor (50 μg). FIG. 6B) Mice were imaged weekly for tumor growth. The following groups were studied: saline (1), tumor lysate+CD200 inhibitor (2), and CNS+tumor lysate+CD200 inhibitor (3) groups. Inoculating mice in the CNS further suppressed tumor growth demonstrating a reversal of tumor induced suppression in the CNS.

FIG. 9A. Vaccination scheme of tumor bearing and non-tumor bearing mice. Mice were bled on day 7. FIG. 9B. Whole blood was stained with an anti-CD8 and SIINFEKL specific detramer (SEQ ID NO: 18), lysed and analyzed by flow cytometry. Results in tumor bearing or non-tumor bearing mice.

FIG. 11B) IL-2 and IL-17 production. Error bars indicate+/−SEM (n=4/group; *P<0.05; **P<0.01).

FIGS. 12A-12C. CD200 inhibitor reverses the suppressive effects of the tumor environment. Tumor and non-tumor bearing mice were vaccinated with OVA+Poly:ICLC+/−the CD200 inhibitor 6059 and analyzed for FIG. 12A) SIINEKL/Kb$^+$CD8$^+$ T cell expansion ("SIINFEKL" disclosed as SEQ ID NO: 18). FIG. 12B) Lymphocytes were harvested and stimulated with SIINFEKL peptide (SEQ ID NO: 18). Supernatants were analyzed for TNFα and IFNγ secretion. FIG. 12C) The CD200 inhibitor 6059 was added to OVA+exosomes. Error bars indicate+/−SEM (n=4/group; *P<0.05; by t-test).

FIGS. 13A-13B. Human CD 11b cells were isolated. Purified CD11b cells were differentiated to immature dendritic cells using GM-CSF and IL4. Cells were pulsed with P1, P2, P3 and P4 CD200 inhibitors (see Table 2). Supernatants were analyzed for FIG. 13A) cytokine or FIG. 13B) chemokine production.

FIG. 15. CD200 inhibitor enhances an antigen specific response. CMV positive human CD11b were maturated to immature dendritic cell (iDC) and pulsed with the CMV antigen pp65+/−hCD200 inhibitor. Immature dendritic cell were maturated to mature DCs. Autologous T cells were added to cells, supernatants were analyzed for IFN gamma production.

FIGS. 17A-17E. Dogs come to the clinic and are diagnosed with brain tumors. The canines' tumors are used to develop their vaccines and are subsequently treated with their personalized vaccines plus the canine specific CD200 inhibitor (LFNTFGSGKISG-amide) (SEQ ID NO: 16)). Unlike the previous glioma bearing dogs that have been treated, a regression of the tumor that remained following surgery is observed. MRI images of a specific dog are shown in A-D. Specifically, approximately 60% of the glioma was resected from this dog that came to the clinic with a glioma (FIGS. 17A, 17C). Tumor was used to make a tumor lysate vaccine. Dog was treated with the tumor lysate+CD200 inhibitor designed for dogs. Dog was reimaged at 4 months post surgery, 24 hours post vaccination (FIGS. 17B, 17D) and are being followed for survival (FIG. 17E). Asterisks represent live dogs on trial as of Oct. 28, 2016.

FIGS. 18A-18E. Experimental Model. CD200 is solubilized from the tumor or endothelial interacting on its receptor (CD200R). This CD200/CD200R interaction induces the upregulation of PPIA through the MYC pathway decreasing TNF alpha and IL2 production needed for an immune response (FIG. 18A). Moreover, integrated pathway analysis (FIG. 18B) and experimental experiments demonstrated that CD200 induces monocyte activation resulting in myeloid derived suppressor cell (MDSC) expansion (FIG. 18C). With the use of CD200 inhibitor (P1A12), the peptide binds to the CD200 activating receptor on monocytes (FIG. 18D) inhibits the production of PPIA (FIG. 18E) and allowing for the dephosphorylation of NFAT.

(FIG. 19A) Vaccination scheme. Wildtype and CD200R knockout mice were vaccinated with tumor lysate or CD200 inhibitor. Mice were revaccinated 24 hours later with tumor lysate or CD200 inhibitor+tumor lysate. Eight slices (levels of skin samples) were analyzed for lymphocyte infiltration six hours after the 2$^{nd}$ vaccination; FIG. 19B) Immunohistochemistry results for tumor lysate+CpG; FIG. 19C) Immunohistochemistry results for tumor lysate+CpG+Antagonist (24 hrs); and FIG. 19D) Counts/Slice for wildtype and CD200R KO mice.

FIG. 20A) Cells isolated from wild type mice were analyzed for co-stimulation molecules and MHC-II expression levels. FIG. 20B) Cells were incubated for 24 hrs, washed 3 times and incubated with purified OT-I T-cells. Supernatants were analyzed for IFN gamma production.

FIG. 26A) Vaccination schedule, FIG. 246B) Glioma bearing mice were vaccinated with tumor lysate (TL)+CD200 inhibitor peptide (P1A12) id.+/−the polyclonal anti-CD200R inhibitor iv. A scrambled CD200 inhibitor was used as a control. Mice were monitored for survival.

DETAILED DESCRIPTION OF THE INVENTION

Figure 1:
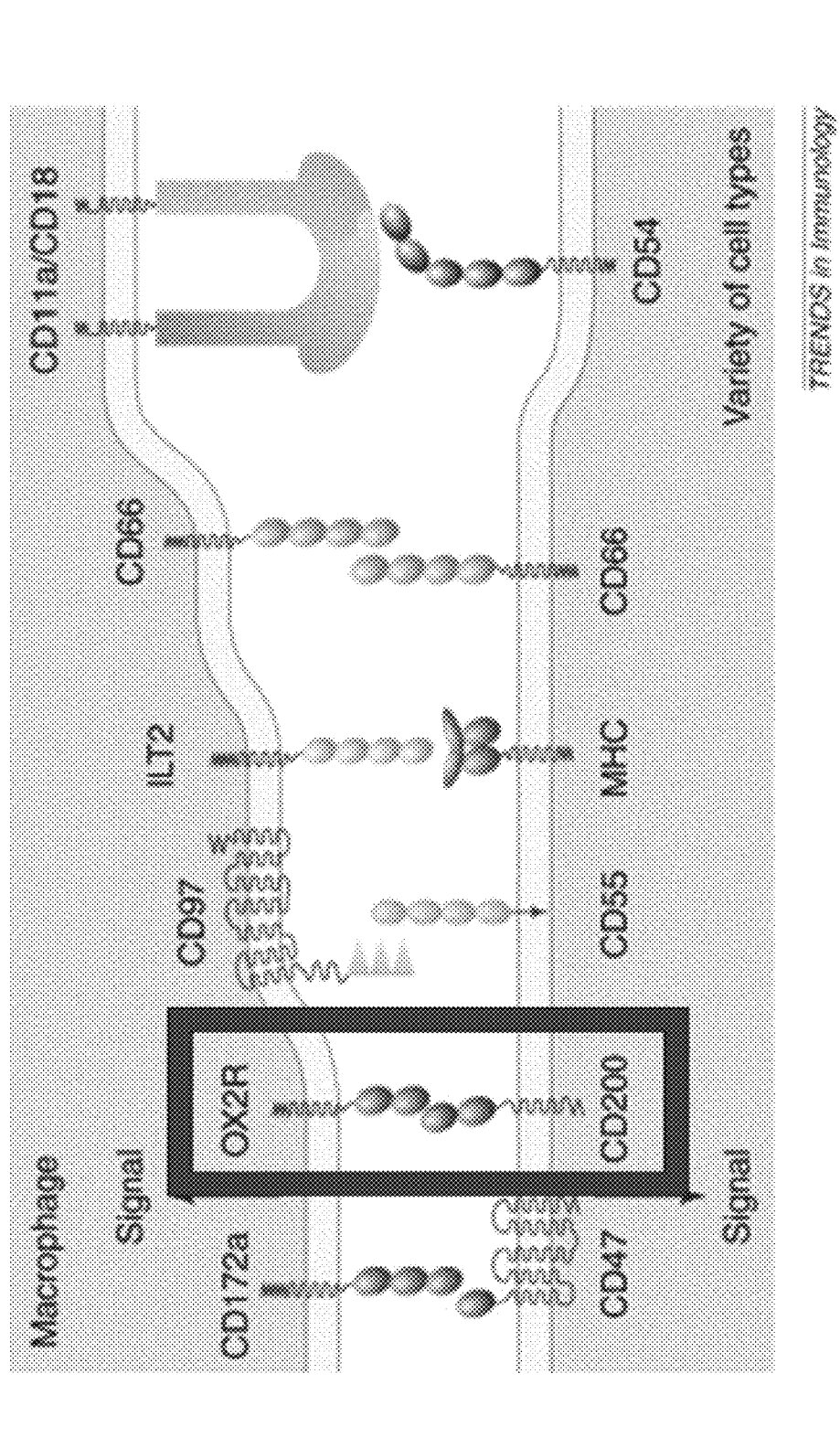
FIG. 1. Illustration of CD200 (OX-2) interaction with CD200R.

It has been found that the interaction of CD200 and CD200-Receptor (CD200R) creates an immune-suppressive tumor microenvironment. It has also been found that soluble CD200 enhances inhibition of leukocytes in the tumor microenvironment. Further, higher expression of CD200 on tumor cells is correlated to malignancies.

The present invention provides a composition comprising a cancer vaccine and a CD200 inhibitor.

Cancer Vaccine

As described herein, a cancer vaccine may be a tumor antigen vaccine. Tumor antigen vaccines are vaccines made of cancer cells (e.g., tumor lysate), parts of cancer cells, or pure tumor antigens (substances isolated from tumor cells). A tumor antigen vaccine may stimulate the body's immune system to find and kill cancer cells. For example, the cancer vaccine may comprise glioma cancer cells, breast cancer cells, or other solid tumor cancer cells, or parts of these cells or antigens derived from these cells. In certain embodiments, the cancer vaccine comprises a vaccine antigen, wherein cultured tumor cell derived lysates are the source of the antigen.

In certain embodiments, the cancer vaccine may be a GL261-derived vaccine. In certain embodiments, the cancer vaccine comprises a peptide containing an OVA-derived SIINFEKL epitope (SEQ ID NO: 18). In certain embodiments the peptide is EVSQLEQLESIINFEKLTE-EWTSSNVM (SEQ ID NO: 19).

CD200 Inhibitors

As used herein an inhibitor of CD200 is also referred to as a competitive inhibitor of CD200.

In certain embodiments a CD200 inhibitor binds to CD200 activation receptor, a receptor for CD200.

Peptides and Peptidomimetic

In certain embodiments a CD200 inhibitor may be a peptide. In certain embodiments, the CD200 inhibitor is a peptide that has a length of 5 to 20 amino acids. For example, in certain embodiments, the peptide is 5, 6, 7, 8, 9, 10, 11, 12, 13 14, 15, 16, 17, 18, 19 or 20 amino acids in length.

In certain embodiments, the peptide may correspond to a domain of CD200. Gorczynski et al. described specific regions of the CD200 protein which act as antagonists (J. Surg. Res 2008; 145(1): 87-96). Thus, in certain embodiments, the CD200 inhibitor may be a peptide described in Gorczynski et al. J. Surg. Res 2008; 145(1): 87-96. In certain embodiments, the CD 200 inhibitor may be:

TABLE 1

Mouse CD200 inhibitor

| Mouse CD200 Inhibitor | Peptide Sequence |
|---|---|
| Inhibitor 6059 | NTIGDGGCY (SEQ ID NO: 1) |
| Inhibitor 6061 | RCSLKTSQE (SEQ ID NO: 2) |
| Inhibitor 4004 | TASLRCSLKTSQE (SEQ ID NO: 3) |
| Inhibitor 4013 | LFNTFGSQKVSGT (SEQ ID NO: 4) |
| Inhibitor 4006 | SQKVSGTACLTLY (SEQ ID NO: 5) |
| P1 (Chen, International Immunology, 17(3), 289-296 (2005)) | VTWQKKKAVSPEN (SEQ ID NO: 8) |
| P1A12 | VTWQKKKAVSPAN (SEQ ID NO: 9) |

TABLE 2

Human CD200 inhibitor

| Human CD200 Inhibitor | Peptide Sequence |
|---|---|
| hP1 | SQKVSGTACLTLY (SEQ ID NO: 5) |
| hP2 | NITLEDEGCYMCLFN (SEQ ID NO: 10) |
| hP3 | VTFSENHGVVIQPAY (SEQ ID NO: 11) |
| hP4 | CLFNTFGFGKISGTA (SEQ ID NO: 12) |
| hP1A6 | SQKVSATACLTLY (SEQ ID NO: 13) |

TABLE 3

Canine CD200 Inhibitor

| Canine CD200 Inhibitor | Peptide Sequence |
|---|---|
| cP1 | VTWQKVKPVSLE-amide (SEQ ID NO: 14) |
| cP2 | NTTLEDEGCYKC-amide (SEQ ID NO: 15) |
| cP3 | LFNTFGSGKISG-amide (SEQ ID NO: 16) |
| cP4 | PASLRCSLQNPE-amide (SEQ ID NO: 17) |

*Tables 1-3: Changes to the natural amino acid sequence are shown in Bold/Underline.

Additionally, in other embodiments of the invention, a CD200 inhibitor may be one described in Kretz-Rommel, Journal of Immunology, 2008, 699-705; Chen, International Immunology, 17(3), 289-296 (2005); Gorczynski, International Scholarly Research Network, ISRN Immunology, Volume 2012, Article ID 682168; pages 1-18; US Patent Publication No. 2002/0168364; U.S. Pat. No. 6,955,811; or U.S. Pat. No. 7,902,151.

In certain embodiments, a CD200 inhibitor is anonnaturally occurring peptide that is not a product of nature. In certain embodiments, a CD200 inhibitor described herein comprises markedly different characteristics (e.g., structural, functional and/or other properties) as compared to naturally occurring peptides that correspond to a domain of CD200.

In certain embodiments, a CD200 peptide inhibitor is engineered to comprise a non-natural mutation(s), and therefore, is structurally different from its naturally occurring counterpart (see, Tables 1-3). In certain embodiments, the mutation(s) results in enhanced CD200 inhibitory activity and/or an enhanced ability to reverse or modulate immune suppression as compared to a naturally occurring peptide, and as a result, is structurally and functionally distinct from its naturally occurring counterpart in its natural state. Accordingly, certain embodiments of the invention provide a CD200 peptide inhibitor comprising one or more mutations, as compared to the sequence of a naturally occurring peptide derived from a CD200 domain.

As described herein, it was unexpectedly determined that mutating particular CD200 peptide inhibitors to include an alanine substitution at certain amino acid positions results in enhanced CD200 inhibitory activity and/or an enhanced ability to reverse or modulate immune suppression (e.g., the $6^{th}$ or $12^{th}$ amino acid, counting from left to right, in the peptide inhibitors may be substituted with an alanine residue). For example, the sequence of the mouse P1 CD200 inhibitor described by Chen, International Immunology, 17(3), 289-296 (2005) (VTWQKKKAVSPEN (SEQ ID NO:8)) may be modified by substituting the $12^{th}$ amino acid with an alanine to enhance its inhibitory activity (PA12: VTWQKKKAVSPAN (SEQ ID NO:9)). Similarly, the hP1 inhibitor (SQKVSGTACLTLY (SEQ ID NO:5)) may be modified by substituting the $6^{th}$ amino acid with an alanine to enhance its inhibitory activity (hP1A6: SQKVS ATACLTLY SEQ ID NO:13) (see, FIG. 16, showing enhanced TNF-α and IL-β production).

Accordingly, in certain embodiments, the mutation(s) is an alanine substitution (e.g., at amino acid position 1, 2, 3, 4, 5, 6, 7, 8, 9, 10, 11, 12, 13, 14 and/or 15). In certain embodiments, the alanine substitution is at amino acid position 6 (counting the amino acids within the peptide from left to right). In certain embodiments, the alanine substitution is at amino acid position 12 (counting the amino acids within the peptide from left to right).

In certain embodiments, the CD200 inhibitor is a peptidomimetic. As used herein, a "peptidomimetic" is a small protein-like chain chemically designed to mimic a peptide. In certain, embodiments the peptidomimetic is designed to possess certain modulated molecular properties as compared to an unmodified peptide, such as enhanced stability (e.g., in vivo half-life) or biological activity. For example, a peptidomimetic may be generated by chemically modifying a peptide described herein. Chemical modifications include, but are not limited to, inclusion of D-isomer amino acids, 3 aza-amino acids, altered backbones and/or incorporation of unnatural amino acids. For example, these strategies are based on the replacement of natural (L-) amino acids with the unnatural (D-) amino acids or 3 aza-amino acids. Other strategies include the replacement of amide bonds (—CONH—) with thioamides or N-methylated amides. Other methods involve changing the N- and C-terminal amino acids to amides, esters, or D-amino acids.

Accordingly, in certain embodiments, a CD200 peptide inhibitor is engineered to comprise one or more D-isomer amino acids. In certain embodiments, a CD200 peptide inhibitor comprises 1, 2, 3, 4, 5, 6, 7, 8, 9, 10, 11, 12, 13, 14, 15 or more D-isomer amino acids. In certain embodiments, about 10, 20, 30, 40, 50, 60, 70, 80, 90 or 100% of the amino acids are D-isomer amino acids.

In certain embodiments, a CD200 peptide inhibitor is engineered to comprise one or more unnatural amino acids (e.g., dehydroalanine, homoserine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). In certain embodiments, a CD200 peptide inhibitor comprises 1, 2, 3, 4, 5, 6, 7, 8, 9, 10, 11, 12, 13, 14, 15 or more unnatural amino acids. In certain embodiments, about 10, 20, 30, 40, 50, 60, 70, 80, 90 or 100% of the amino acids are unnatural amino acids.

Antibodies or Antibody Fragments

In certain embodiments, the at least one CD200 inhibitor is an antibody (e.g., an antibody that binds to a specific epitope of the activation CD200R, a receptor for CD200). Antibodies that bind to CD200R are known in the art and are commercially available.

As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$—$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of $F(ab')_2$. Other chemically crosslinked antibody fragments are also known to those skilled in the art. Pepsin digestion of an antibody yields two fragments; one is a $F(ab')_2$ fragment which comprises two antigen-binding domains and can cross-react with antigens, and the other is the remaining fragment (referred to as pFc'). Herein, an antibody fragment equivalent to that obtained by pepsin digestion is referred to as a "$F(ab')_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, $F(ab')_2$-SH fragments can be recovered directly from hosts, such as E. coli, and then allowed to form $F(ab')_2$ fragments by chemical crosslinking (Carter et al., Bio/Technology 10:163-167 (1992)). In an alternative method, $F(ab')_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

Use of CD200 Inhibitors

As described herein, a CD200 inhibitor or a composition as described herein comprising a CD200 inhibitor may be used to reverse or modulate immune suppression. CD200 is an immunosuppressive protein that negatively regulates immune cells bearing the CD200R (e.g., suppresses antigen-specific $CD8^+$ T cell responses). As described herein, "reversing or modulating immune suppression" refers to altering, impeding, reducing the immunosuppressive properties of the CD200 protein and/or tumor. In certain embodiments, the CD200 protein activity is reduced in a mammal by 1%, 2%, 3%, 4%, 5%, 10%, 20%, 30%, 40%, 50%, 60%, 70%, 80%, 90%, 100% as compared to the activity on the tumor in the absence of the CD200 protein. For example, immunosuppressive cells, such as myeloid-derived suppressor cells and regulatory T cells show increased activity while dendritic cells (DCs) appear to be impaired in tumors and sentinel lymph nodes in cancer patients. Accordingly, in certain embodiments, administration of a CD200 inhibitor or a composition as described herein comprising a CD200 inhibitor could decrease the activity of immunosuppressive cells, such as myeloid-derived suppressor cells and regulatory T cells and/or could increase the activity of DCs in the tumor microenvironment and/or sentinel lymph nodes. In certain embodiments, reversal or modulation could be ascertained by assessing cytokine profiles as described herein (e.g., cytokine profiles could be determined before and after administration of a CD200 inhibitor and compared; see also, the Examples).

As referred herein, the "tumor microenvironment" is the normal cells, molecules and blood vessels that surround and feed a tumor cell. A tumor can change its microenvironment and the microenvironment can affect how a tumor grows and spreads.

As described herein, a CD200 inhibitor may enhance the efficacy of a cancer vaccine (e.g., when administered simultaneously or sequentially). For example, in certain embodiments the CD200 inhibitor and cancer vaccine may be in a combined formulation (i.e., a composition described herein) or may be in separate formulations for sequential or simultaneous administration.

As described herein, "enhancing efficacy" means a beneficial immune response is generated by the administration of a CD200 inhibitor and cancer vaccine that is greater than the beneficial immune response generated by the administration of just the cancer vaccine. In certain embodiments, administration of a CD200 inhibitor and a cancer vaccine (e.g., a composition described herein) reduces the size of a tumor (volume) in a mammal by 1%, 2%, 3%, 4%, 5%, 10%, 20%, 30%, 40%, 50%, 60%, 70%, 80%, 90%, 100% and this reduction is more than the reduction from administration the cancer vaccine alone. In certain embodiments, the administration of a CD200 inhibitor and a cancer vaccine (e.g., simultaneous or sequential administration) results in a synergistic effect.

Agonist of CD200

As used herein, an agonist of CD200 has an equivalent biological effect as CD200. Certain CD200 agonists have been previously described, for example by Gorczynski et al. J. Surg. Res 2008; 145(1): 87-96, including agonist 4005 (SPENMVTYSKT (SEQ ID NO:6)) and agonist 4012 (TYSKTHGVVTQ (SEQ ID NO:7)).

Pharmaceutical Compositions

The present invention also provides, in certain embodiments, a pharmaceutical composition which comprises a pharmaceutically acceptable carrier or diluent and, as an active ingredient, a composition as described herein. In certain embodiments, the composition is formulated for oral administration or injection.

The present invention also provides, in certain embodiments, a composition as described herein for use in a method of treatment of a human or animal body by therapy.

The present invention also provides, in certain embodiments, a composition as described herein for use in medical therapy.

The present invention also provides, in certain embodiments, a composition as described herein for use in the treatment of a disease or disorder arising from abnormal cell growth, function or behavior.

The present invention also provides, in certain embodiments, the use of a composition as described herein in the manufacture of a medicament for treating a disease or disorder arising from abnormal cell growth, function or behavior. In certain embodiments, the disease or disorder is cancer. In certain embodiments, the cancer is selected from solid tumors of the colon, breast, brain, liver, ovarian, gastric, lung, and head and neck. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a method of treating a disease or disorder arising from abnormal cell growth, function or behavior, which method comprises administering to a patient in need thereof a composition as described herein. In certain embodiments, the disease or disorder is cancer. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a process for producing a pharmaceutical composition comprising combining a composition as described herein with a pharmaceutically acceptable carrier.

The present invention also provides, in certain embodiments, a kit for treating cancer, comprising: (a) a first pharmaceutical composition comprising a composition as described herein; and (b) instructions for use.

The present invention further provides nucleic acid sequences that encode the CD200 inhibitor peptides described above. The nucleic acids encoding the CD200 peptides can be produced using the methods well known in the art (see, e.g., Sambrook and Russell, 2001).

Accordingly, certain embodiments of the invention provide a nucleic acid molecule encoding a CD200 inhibitor peptide as described herein.

Certain embodiments of the invention provide an expression cassette comprising a nucleic acid molecule described herein. In certain embodiments, the expression cassette described herein further comprises a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene.

Certain embodiments of the invention provide a viral vector comprising an expression cassette described herein. Examples of appropriate vectors include adenoviral, lentiviral, adeno-associated viral (AAV), poliovirus, HSV, or murine Maloney-based viral vectors. In certain embodiments, the vector is an adenovirus (Ad).

In certain embodiments, the viral vector is delivered directly into the tumor mass of a mammal. In certain embodiments, a cancer vaccine is administered to the mammal prior to delivery of the viral vector, simultaneously with the viral vector delivery or after delivery of the viral vector.

The present invention provides cells (such as a mammalian cell) containing the expression cassette or vectors described above. The present invention also provides a nonhuman mammal containing the expression cassette or vectors described above.

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified composition can be isolated, lyophilized and stabilized. The composition may then be adjusted to an appropriate concentration, optionally combined with a suitable vaccine adjuvant, and packaged for use.

Adjuvants

An "adjuvant" is any molecule or compound that non-specifically stimulates the humoral and/or cellular immune response. They are considered to be nonspecific because they only produce an immune response in the presence of an antigen. Adjuvants allow much smaller doses of antigen to be used and are essential to inducing a strong antibody response to soluble antigens. For example, when a therapeutic agent is administered in conjunction with an adjuvant, the therapeutic agent can be administered before, after, and/or simultaneously with the adjuvant. Adjuvants are known in the art and may include, but are not limited to, CpG oligonucleotides, Poly:ICLC and imiquimod.

Methods for Making Tumor Lysates

Tumor lysates are made by extracting a sample of the tumor to be treated from the subject. The tumor cells are then lysed. Methods of making effective tumor lysates include, but are not limited to, freeze thaw method, sonication, microwave, boiling, high heat, detergent or chemical-based cell lysis, electric or current-based lysis, and other physical methods, such as extreme force.

In certain embodiments, such as when a glioma is to be treated, EGF receptor VIII variant and IL-13 receptor alpha-2, which are glioma specific receptors (or expression vectors encoding these proteins), may be added to the tumor lysate.

Formulations and Methods of Administration

The vaccines and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Additional ingredients such as fragrances or antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In certain embodiments, the vaccine of the present invention reduces the size of the tumor in the subject by at least about 10%-100% (volume of tumor).

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 100, 90, 80, 70, 60, 50, 40 or 20 sequential nucleotides that is transcribed and translated into a peptide. Such a peptide may be a competitive inhibitor to CD200 and bind to CD200R. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art as described by Adelman et al. (1983). Briefly, a nucleic acid encoding a peptide described herein can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding the peptide. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13mp18 and M13mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the RNA, or the like. Such elements may be included in the DNA as desired to obtain the optimal expression in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of E. coli and the luciferase gene from firefly Photinus pyralis. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein. For example, Sambrook and Russell, infra, provides suitable methods of construction.

The recombinant DNA can be readily introduced into the host cells, e.g., mammalian, bacterial, yeast or insect cells by transfection with an expression vector composed of DNA encoding the peptide (e.g., CD200 inhibitor) by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed above, a "transfected", "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the peptide (e.g., a CD200 inhibitor).

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell", comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining a regulatable promoter with an endogenous coding sequence via homologous recombination.

Methods for Introducing the Expression Cassettes of the Invention into Cells

The condition amenable to gene therapy may be a prophylactic process, i.e., a process for preventing disease or an undesired medical condition. Thus, the instant invention embraces a system for delivering peptides, such as CD200 inhibitors, that have a prophylactic function (i.e., a prophylactic agent) to the mammalian recipient.

The nucleic acid material (e.g., an expression cassette encoding a CD200 inhibitor peptide) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the peptide together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain a regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of peptide (e.g., a CD200 inhibitor) generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding the peptide that are in the cell.

In one embodiment of the present invention, an expression cassette may contain a pol II promoter that is operably linked to a nucleic acid sequence encoding a peptide (e.g., a CD200 inhibitor). Thus, the pol II promoter, i.e., a RNA polymerase II dependent promoter, initiates the transcription of the RNA, which encodes the peptide of interest. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the peptide may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

In one embodiment, a pol II promoter that effectively directs the expression of the RNA in the cell type, organelle, and organism chosen for expression will be employed. Those of ordinary skill in the art of molecular biology generally know the use of promoters for protein expression, for example, see Sambrook and Russell (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the peptide, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the peptide(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for expressing a peptide described herein.

The instant invention also provides methods for genetically modifying cells of a mammalian recipient in vivo. According to one embodiment, the method comprises introducing an expression vector for expressing a peptide described herein in cells of the mammalian recipient in situ by, for example, injecting the vector into the recipient.

Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the treatment of cancer has been accomplished with recombinant adenoviral vectors.

The selection and optimization of a particular expression vector for expressing a specific peptide (e.g., a CD200 inhibitor) in a cell can be accomplished by obtaining the nucleic acid sequence encoding the peptide, possibly with one or more appropriate control regions (e.g., promoter, insertion sequence); preparing a vector construct comprising the vector into which is inserted the nucleic acid sequence encoding the peptide; transfecting or transducing cultured cells in vitro with the vector construct; and determining whether the peptide is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the peptide into the host cell genome, thereby permitting the nucleic acid sequence encoding the peptide to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the peptide into an undesirable position in the target cell genome which, for example, leads to unregulated cell growth and (2) the need for target cell proliferation in order for the nucleic acid sequence encoding the peptide carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate the peptide (e.g., a CD200 inhibitor) in a CNS cancer tumor (e.g, a glioma). A suitable vector for this application is an FIV vector or an AAV vector. For example, one may use AAV5. Also, one may apply poliovirus or HSV vectors.

Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered to accommodate expression cassettes in distinct regions.

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain. An important consideration for the present application is that AAV5 transduces striatal and cortical neurons, and is not associated with any known pathologies.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the viruses' native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

Definitions

"Bound" refers to binding or attachment that may be covalent, e.g., by chemically coupling, or non-covalent, e.g., ionic interactions, hydrophobic interactions, hydrogen bonds. Covalent bonds can be, for example, ester, ether, phosphoester, amide, peptide, imide, carbon-sulfur bonds, carbon-phosphorus bonds, and the like. The term "bound" is broader than and includes terms such as "conjugated," "coupled," "fused" and "attached."

The invention encompasses isolated or substantially purified protein (or peptide) compositions. In the context of the present invention, an "isolated" or "purified" polypeptide is a polypeptide that exists apart from its native environment and is therefore not a product of nature. A polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Wild-type" refers to the normal gene, or organism found in nature without any known mutation.

"Operably-linked" refers to the association of molecules so that the function of one is affected by the other. For example, operably-linked nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., dehydroalanine, homoserine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein) The term also comprises natural and unnatural amino acids bearing a cyclopropyl side chain or an ethyl side chain.

The invention encompasses isolated or substantially purified protein compositions. In the context of the present invention, an "isolated" or "purified" polypeptide is a polypeptide that exists apart from its native environment. The terms "polypeptide" and "protein" are used interchangeably herein. An isolated protein molecule may exist in a purified form or may exist in a non-native environment such as, for example, a transgenic host cell or bacteriophage. For example, an "isolated" or "purified" protein, or biologically active portion thereof, may be substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. In certain embodiments, an "isolated" or "purified" protein may include cell lysates. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of a protein.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred if little or no change in biological activity is desired.

Thus, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., *E. coli*) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional peptide of interest, for example a CD200 inhibitor. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

"Constitutive expression" refers to expression using a constitutive or regulated promoter. "Conditional" and "regulated expression" refer to expression controlled by a regulated promoter.

"Expression" refers to the transcription and/or translation of an endogenous gene, heterologous gene or nucleic acid segment, or a transgene in cells. Expression may also refer to the production of protein.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

(e)(ii) For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m 81.5° C.+16.6(\log M)+0.41(\% GC)-0.61(\% form)-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

As discussed above, the terms "isolated and/or purified" in terms of a nucleic acid refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is complementary or hybridizes to a sequence in a gene of interest and remains stably bound under stringent conditions (as defined by methods well known in the art). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, an antigen-presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g., using a $^{51}Cr$ release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

Certain embodiments of the invention will now be illustrated by the following non-limiting Examples.

Example 1

Figure 2A:
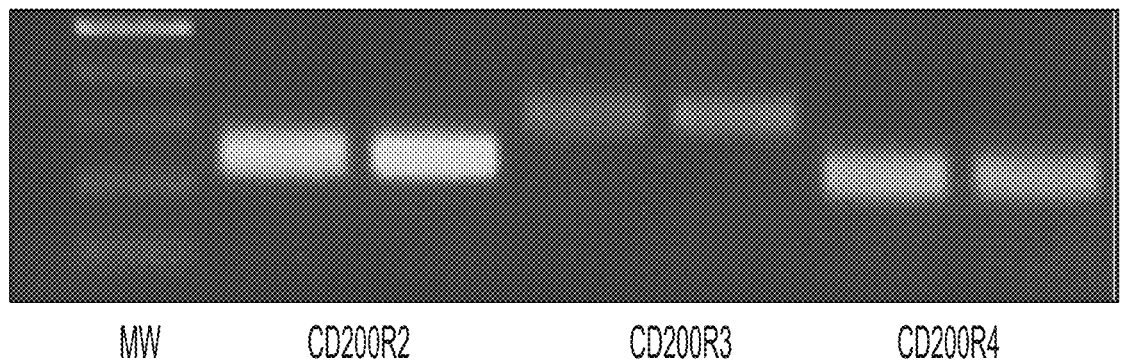
FIGS. 2A-2D. CD200 inhibitors target CD200 activation receptors. CD200 activation receptors on FIG. 2A) murine dendritic cells and FIG. 2B) human monocytes (CD14) and a monocyte cell line (THP).
Figure 2B:
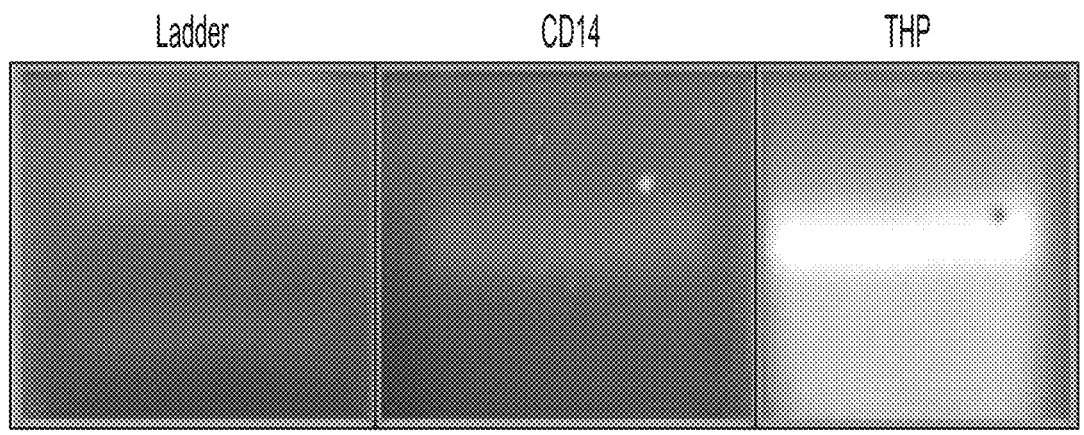

Determination of how Select Inhibitors Reverse CD200-Induced Immune Suppression in Sentinel Lymph Nodes Tumor microenvironments and the sentinel lymph nodes exist under immunosuppressive conditions that inhibit the ability of the immune system to eliminate cancer cells and prevent reoccurrence. While researchers have generated signaling pathway inhibitors to overcome immunosuppressive cascades in either cancer or immune cells, or both, little efficacy has been achieved. CD200 is an immunosuppressive protein that negatively regulates immune cells bearing the inhibitory CD200 receptor (CD200R1) (FIG. 1). However, the CD2000 receptor family also has several unique isoforms (activation receptors CD200R2, CD200R3, CD200R4 and CD200R5) (FIG. 2A). CD200R5 is restricted to CD-1 strain of mice, and one activation receptor in humans (FIG. 2B). Recently, it has been reported that CD200 contains domains that have been hypothesized to bind to the activation receptors modulating/reversing the suppressive properties of the protein.

Figure 2C:
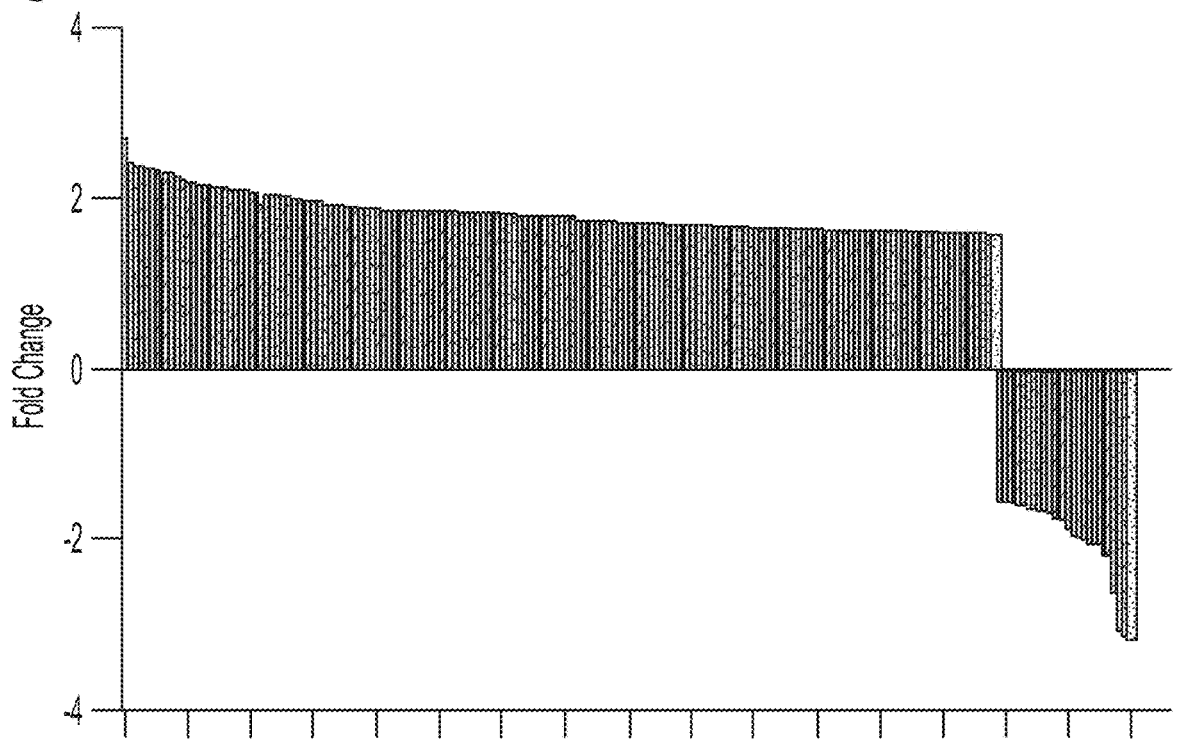
Figure 2D:
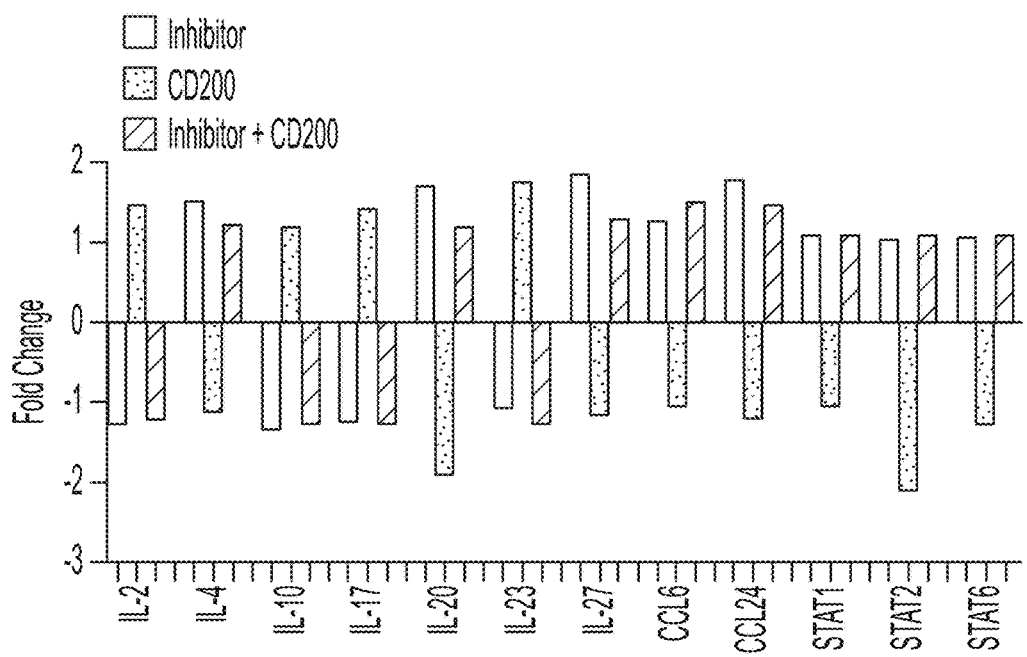
Figure 13B:
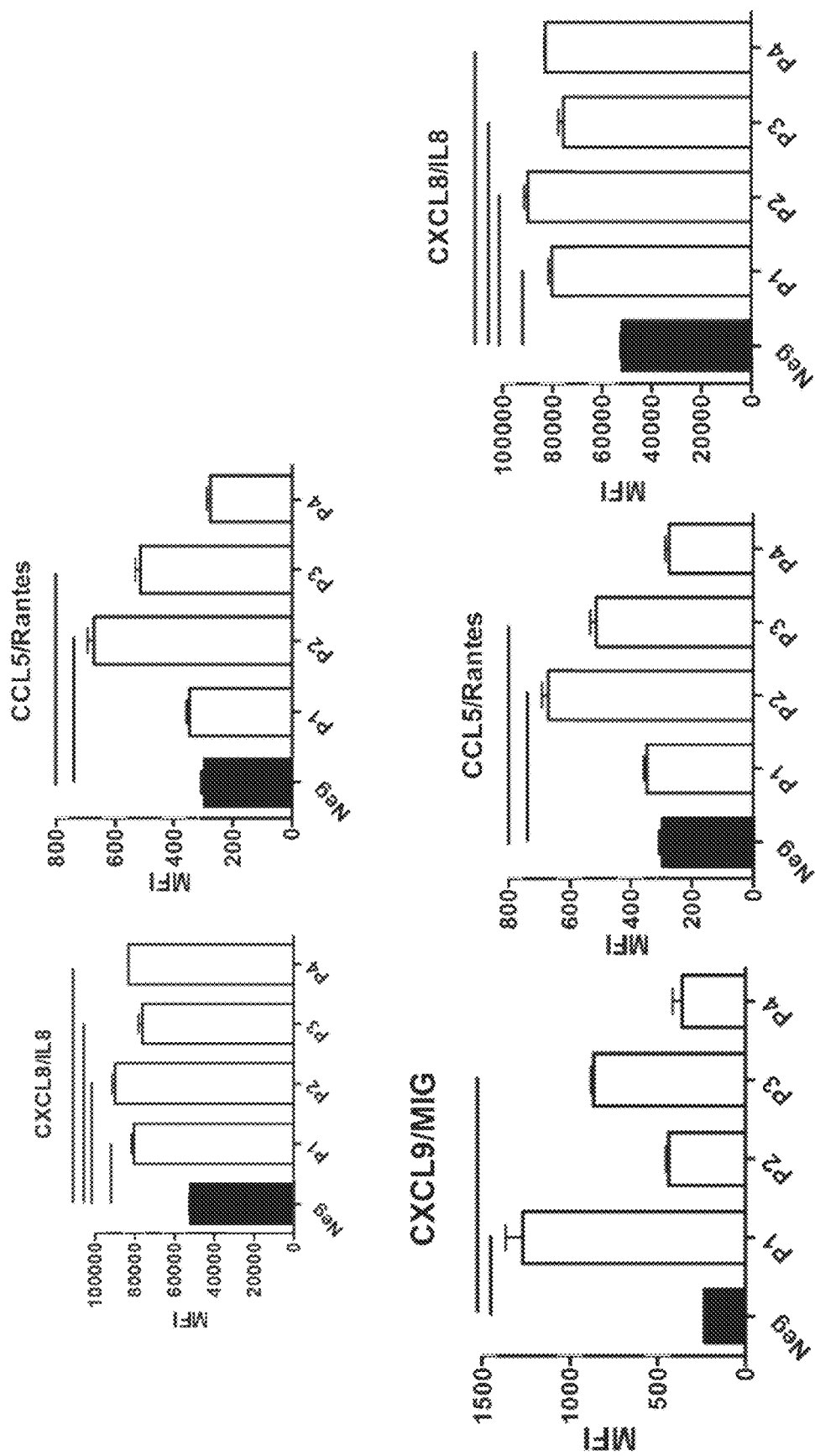
Figure 16:
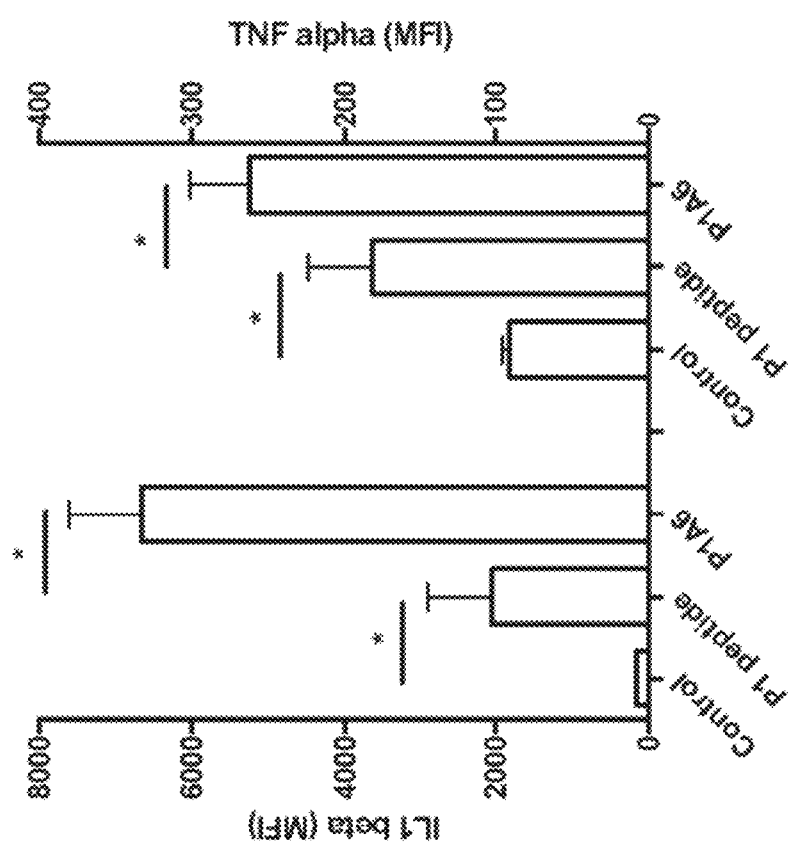
FIG. 16. Human CD11b cells were isolated and the purified CD11b cells were differentiated to immature dendritic cells using GM-CSF and IL4. Cells were pulsed with human P1 peptide, or a mutated version thereof comprising an alanine substitution (denoted by P1 and the amino acid substitution and position; e.g., P1A1, P1A2, P1A3, P1A4, P1A5, P1A6, etc.) (see, Table 2). Supernatants were analyzed for cytokine production. The results indicated that substituting the 6$^{th}$ amino acid with an alanine significantly enhanced response.
Figure 19A:
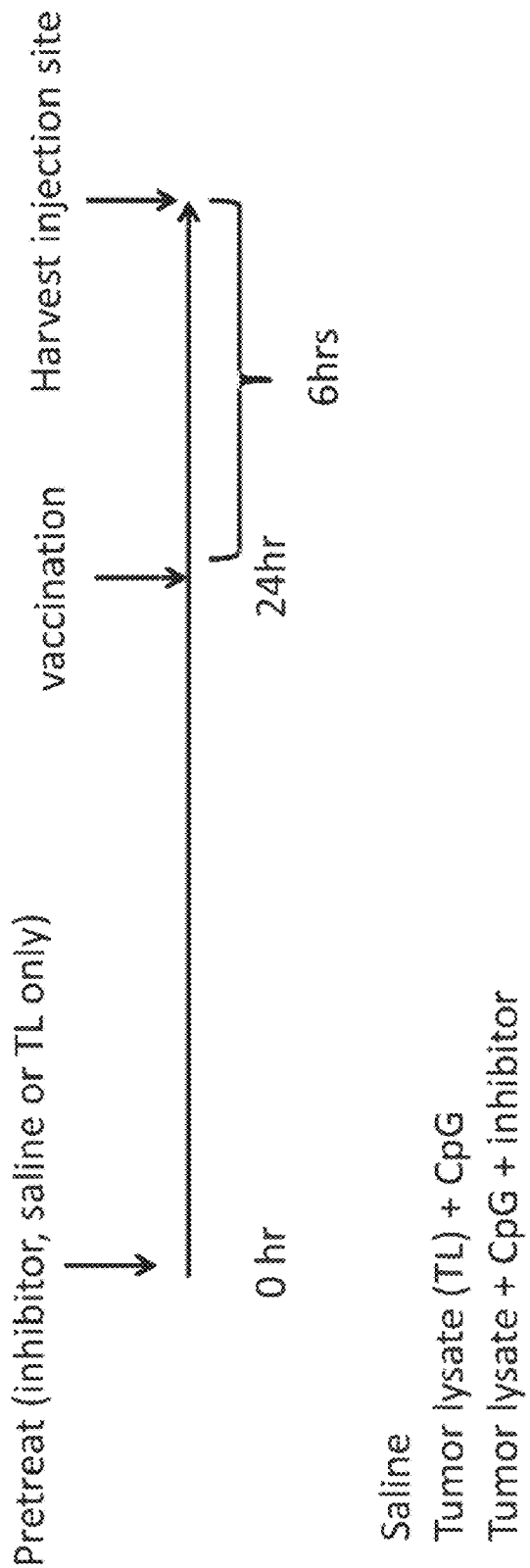
FIGS. 19A-19D. CD200 Inhibitor Enhances Chemotaxis.
Figure 19B:
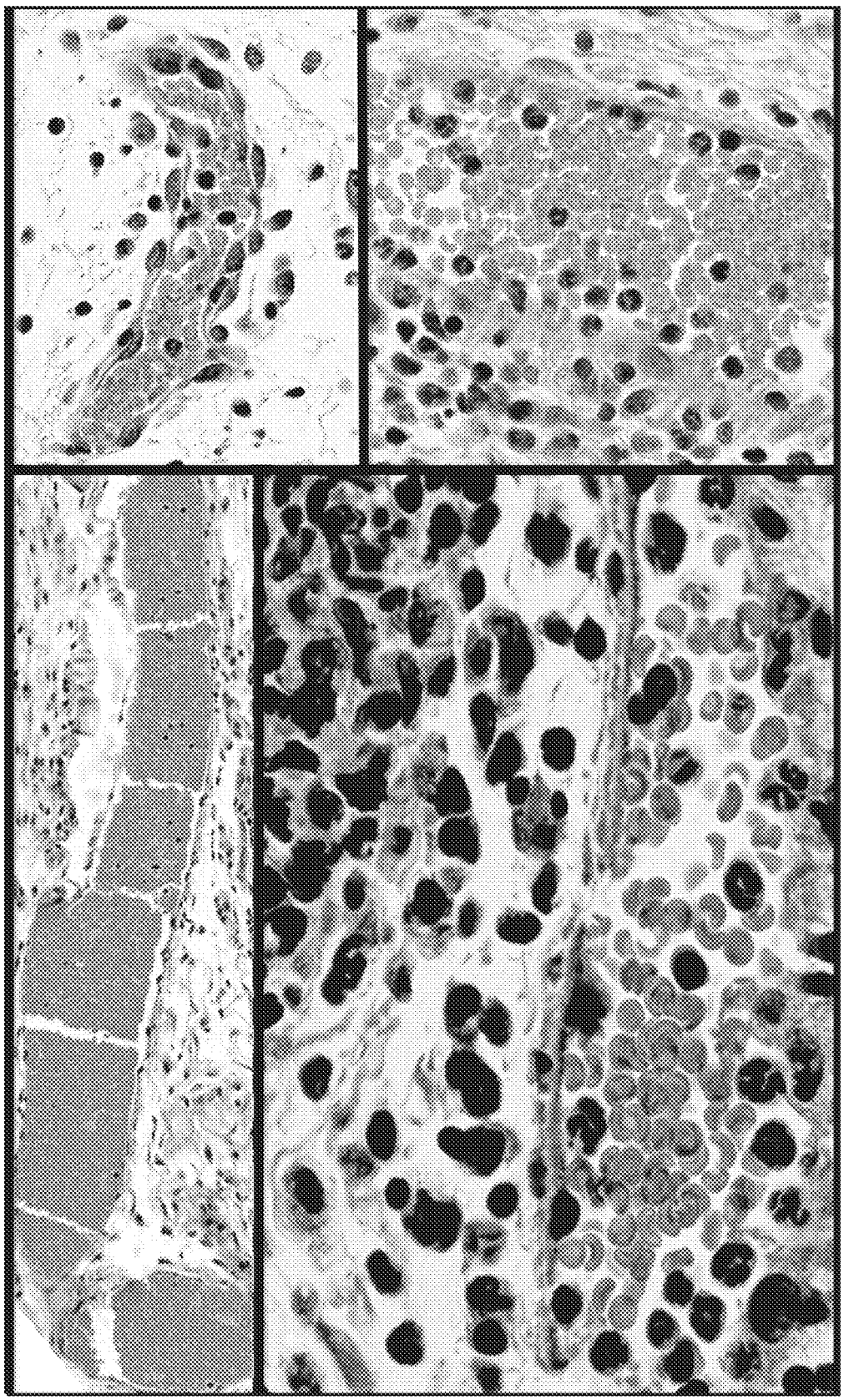
Figure 19C:
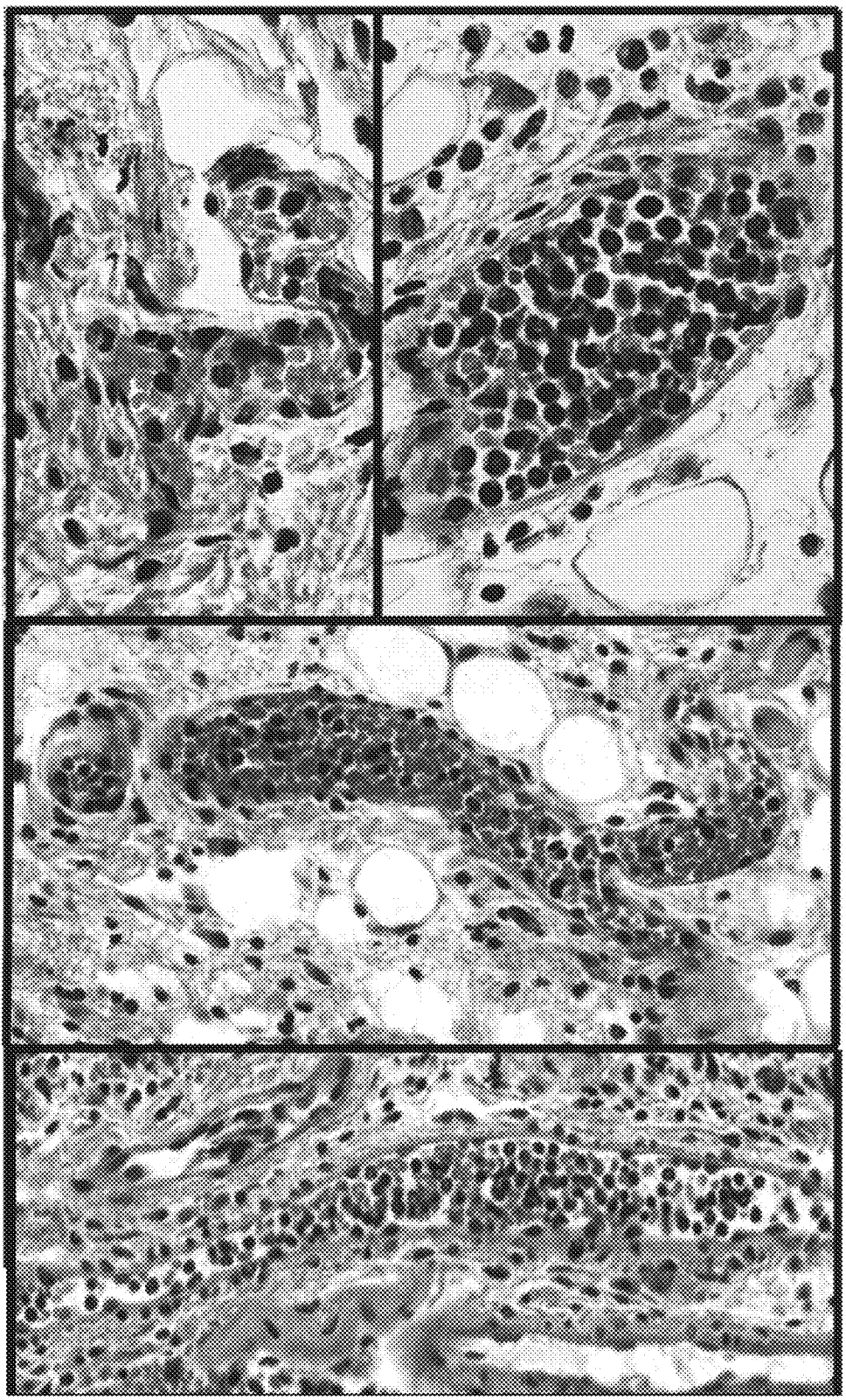
Figure 19D:
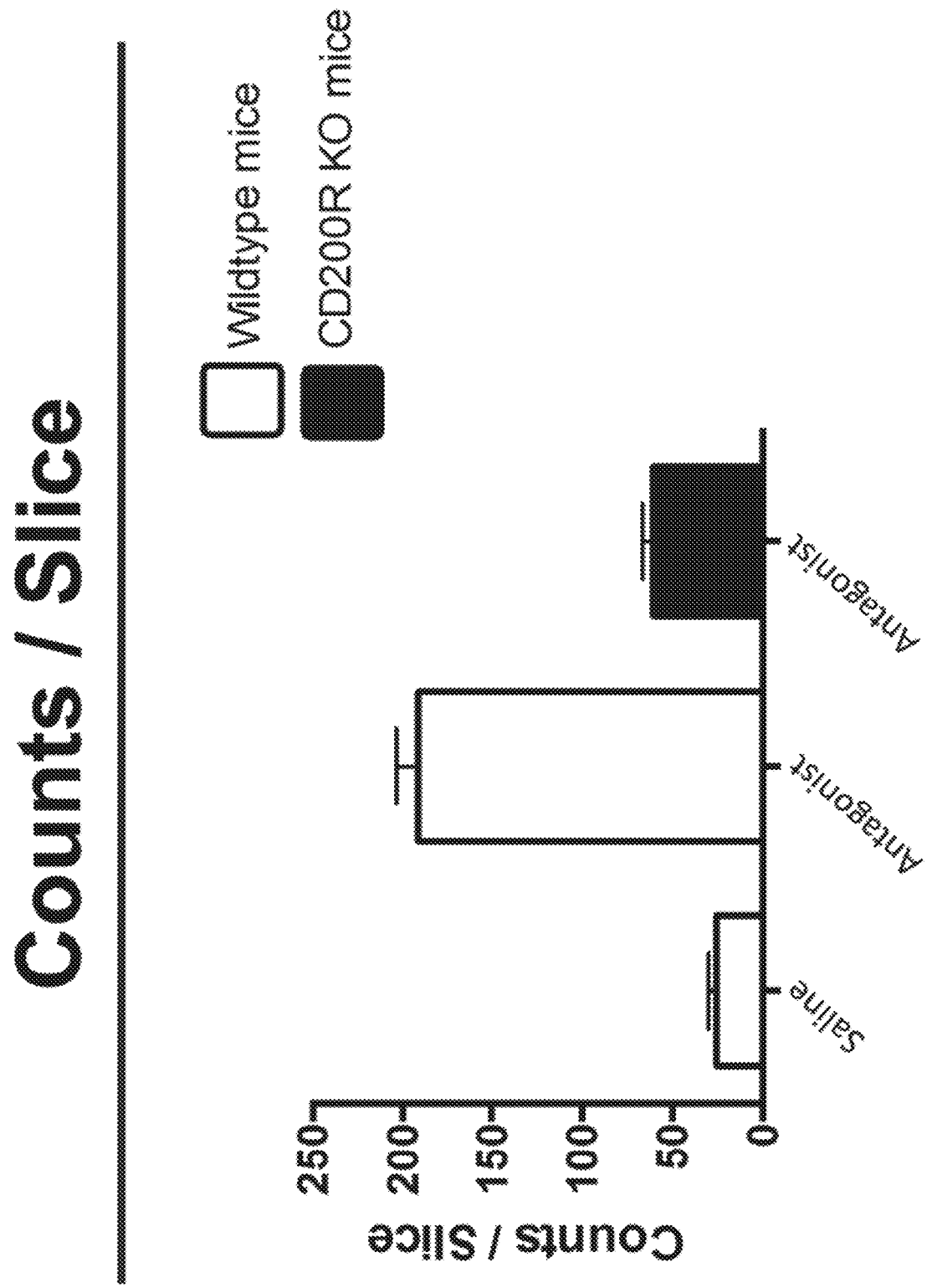
Figure 20B:
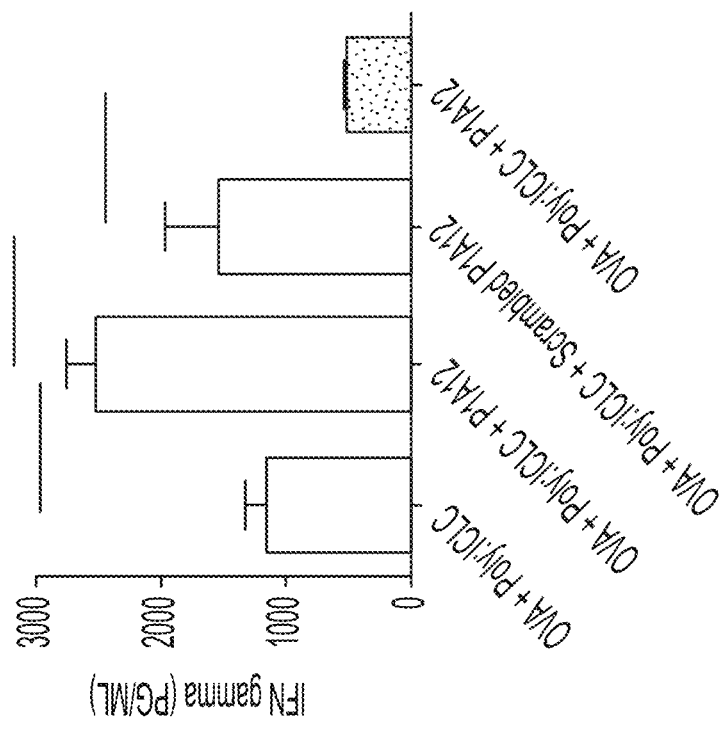
FIGS. 20A-20B. CD200 Inhibitor Activate CD11b Cells. Purified monocytes from wildtype (white bars) or CD200 receptor knock out mice (black bar) were pulsed with OVA or OVA+CD200 inhibitor (P1A12). Scrambled P1A12 inhibitor was used as a control.
Figure 20A:
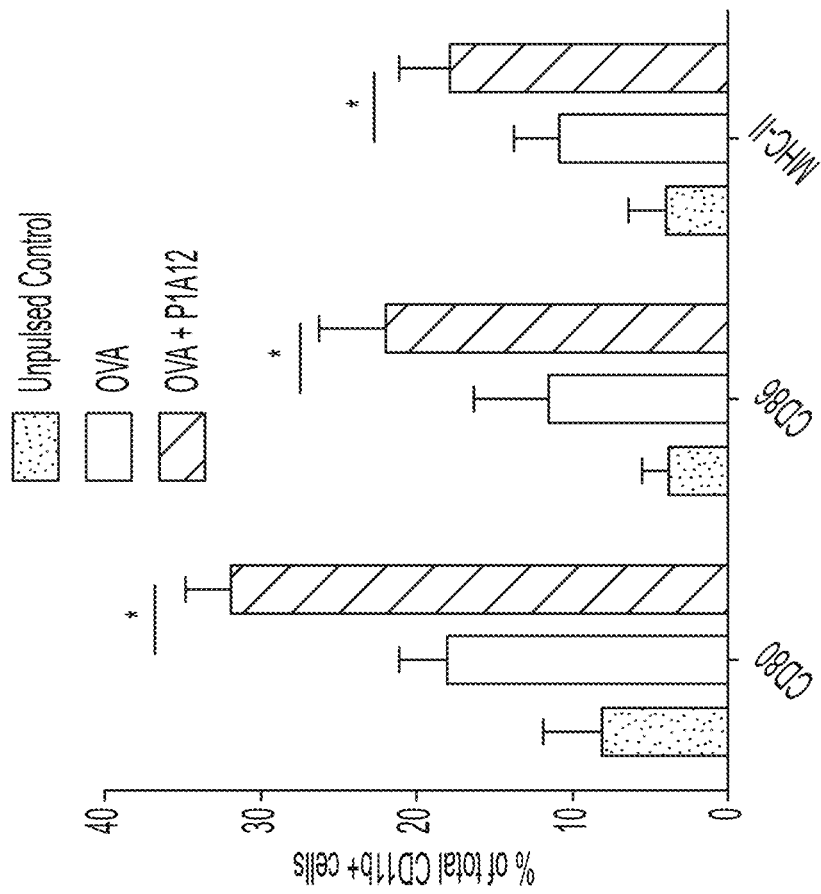
Figure 21:
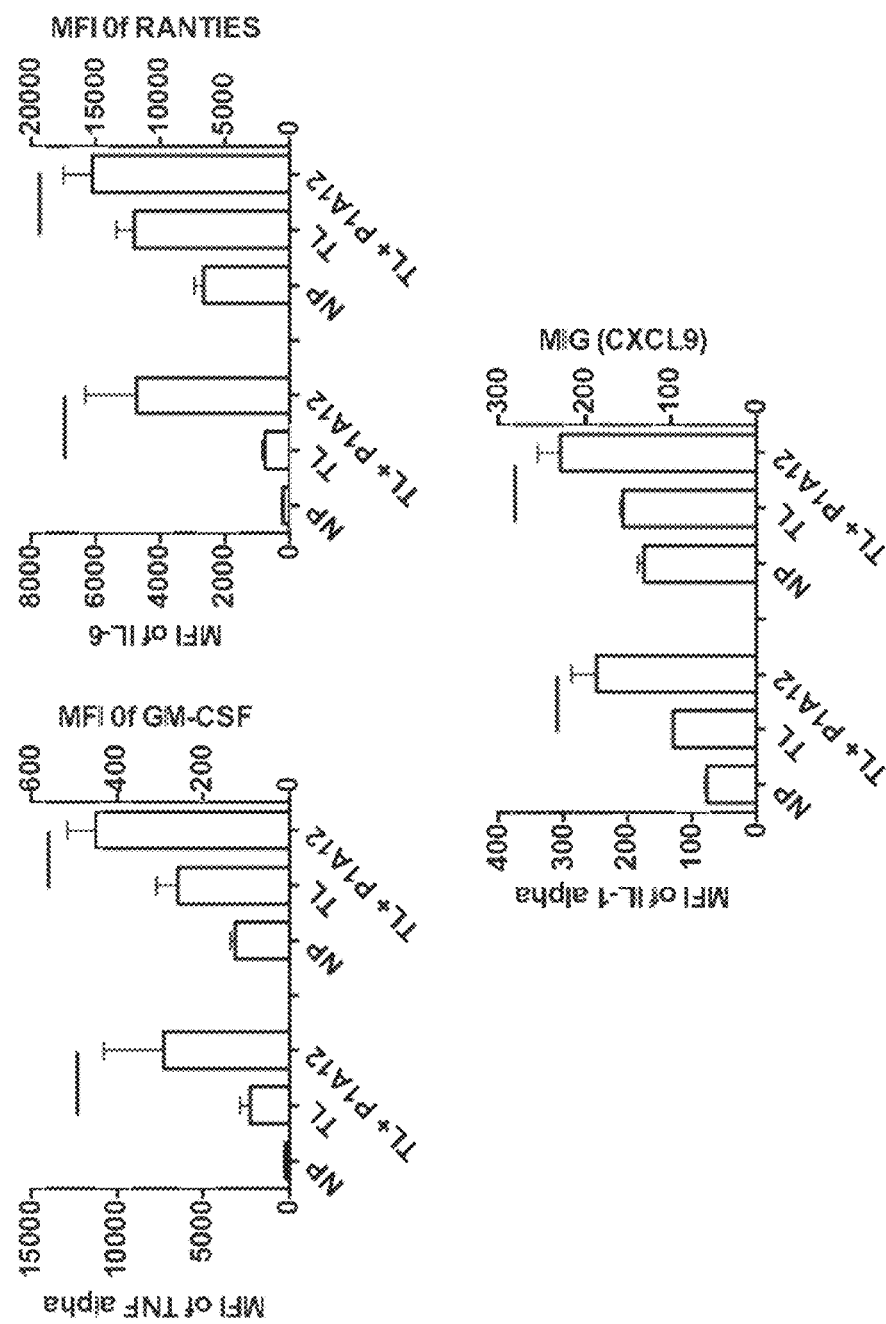
FIG. 21. Purified monocytes from wildtype mice were pulsed with tumor lysate (TL) or tumor lysate+CD200 inhibitor (P1A12). Cells were incubated for 48 hrs and analyzed for cytokine and chemokine production.
Figure 22:
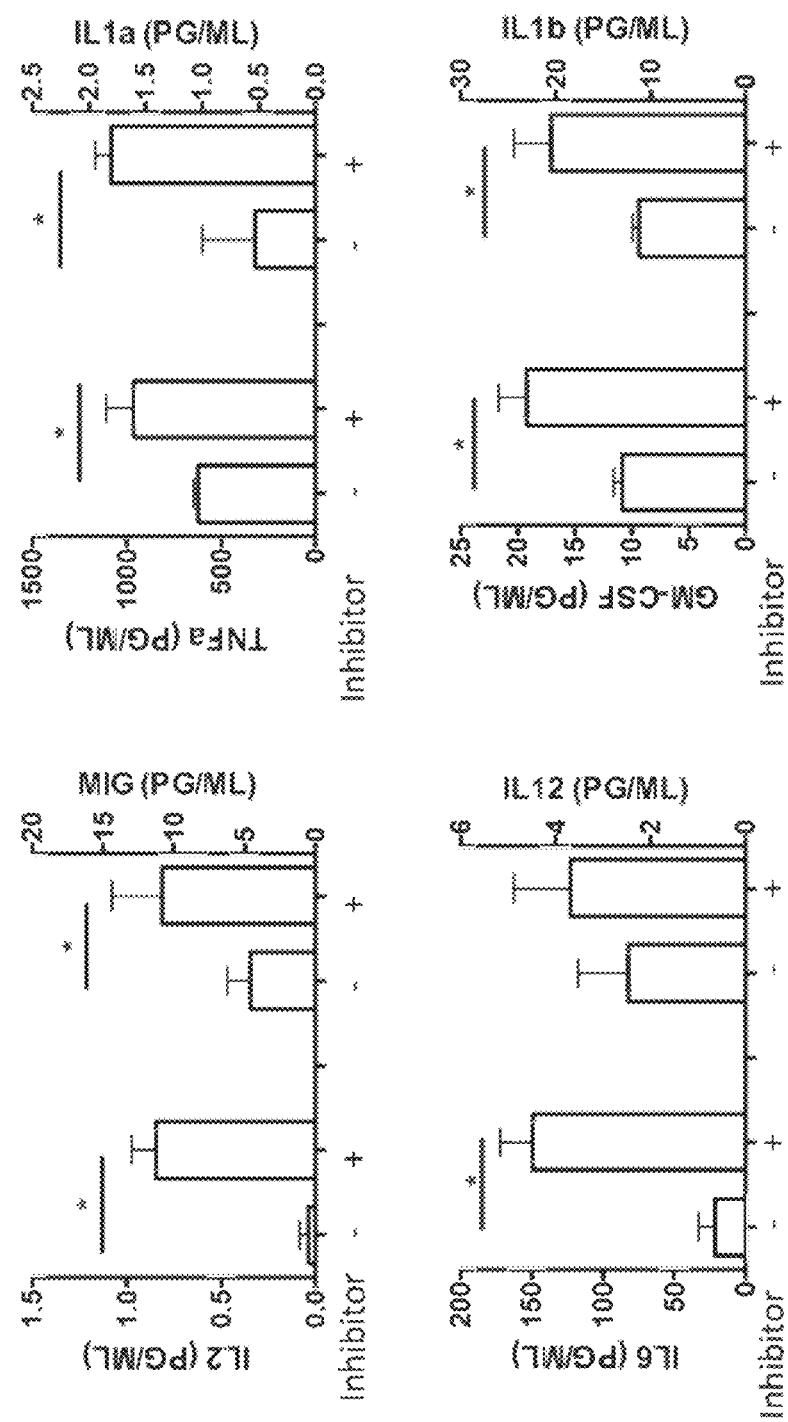
FIG. 22. Purified bone marrow dendritic cells were pulsed with CD200 inhibitor (P1A12). Cells were incubated for 48 hrs and analyzed for cytokine and chemokine production.

As described herein, the ability of these CD200 inhibitors targeting the activation receptor to activate the receptors (FIG. 2D) reverse the suppressive properties of the CD200 protein (FIG. 2C) (Xiong et al., Immunother 2016; 8(9): 1059-1071) CD200 inhibitors activate antigen-presenting cells. Murine CD11b cells were pulsed with the CD200 inhibitor (P1A12). 48 hours later, supernatants were analyzed for cytokine and chemokine production (FIG. 22). The same results were found by pulsing human dendritic cells with the human CD200 inhibitor (FIGS. 13A-13B). Responses were enhanced by substituting the $6^{th}$ amino acid with an alanine (FIG. 16). We also determined the enhanced chemokine production enhanced leukocyte infiltration into tumor site. Non-tumor bearing mice were vaccinated with saline, tumor lysate or the CD200 inhibitor P1A12 alone. Twenty-four hours later, mice were re-vaccinated with saline, tumor lysate+the adjuvant CpG or tumor lysates, CpG+the CD200 inhibitor. Six hours later, vaccination site was analyzed for leukocyte infiltration (FIG. 19D). Described herein are studies designed to: i) optimize the inhibitors, ii) evaluate CD200/CD200R interactions on the ability of dendritic cells to present antigen, iii), and determine the CD200 derived competitive inhibitors mechanism(s) of action.

Figure 6A:
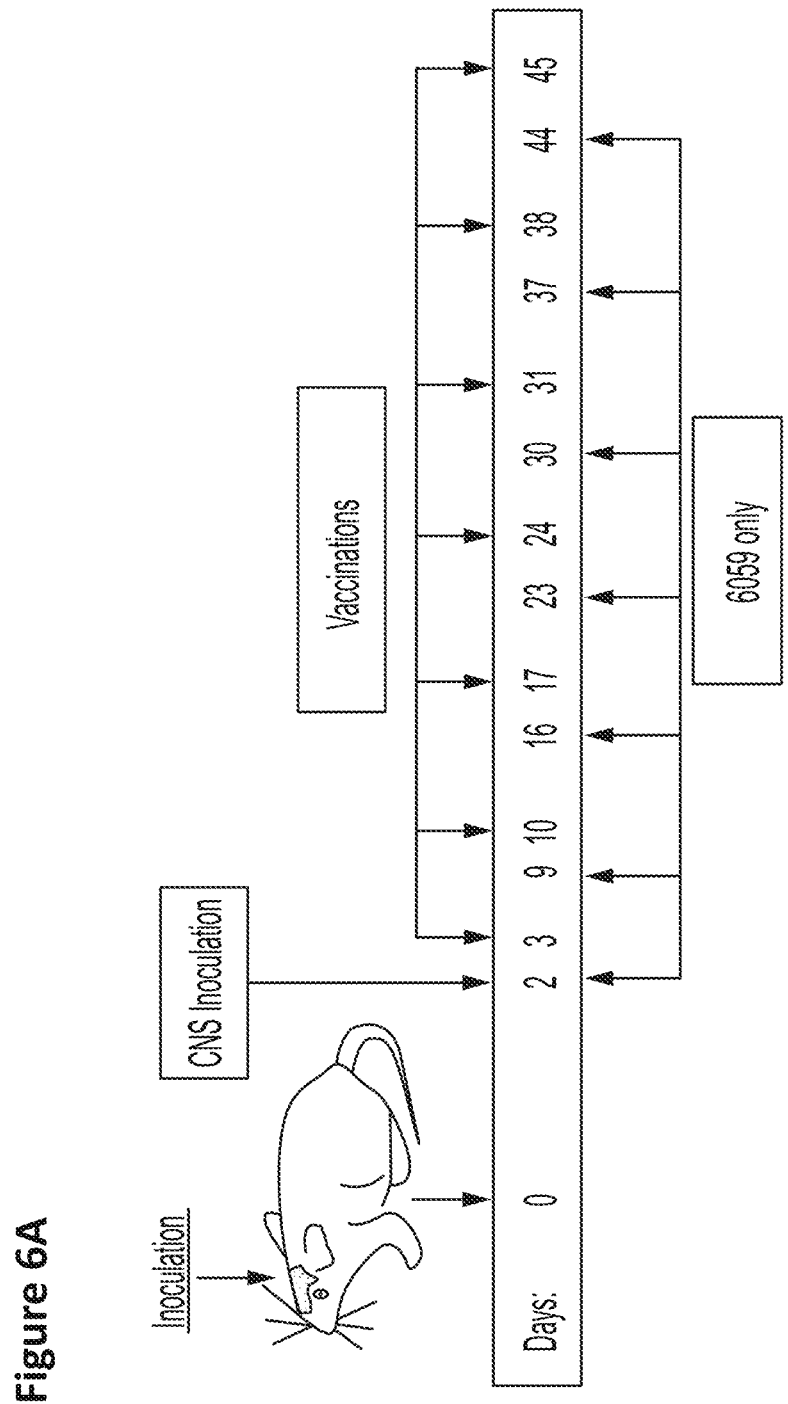
FIGS. 6A-6B.
Figure 6B:
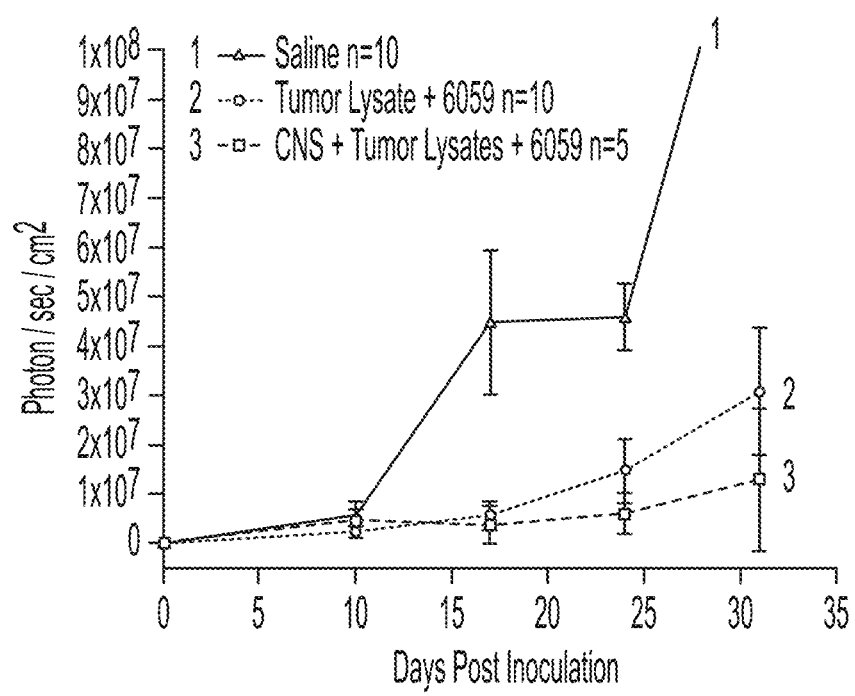

When cancer is detected in the clinic, patients are generally immunosuppressed due to the generation of immunosuppressive conditions in tumor-associated microenvironments. Immunosuppressive cells, such as myeloid-derived suppressor cells and regulatory T cells show increased activity while dendritic cells (DCs) appear to be impaired in tumors and sentinel lymph nodes in cancer patients. Because of the inhibitory CD200 receptor (CD200R1) expressed on T cells (Wright et al., J Immunol 2003; 171(6): 3034-46; Gorczynski et al., J Immunol 2000; 165(9): 4854-60; Gorczynski et al., J Immunol 2004; 172(12): 7744-9), CD200 secretion from the tumor microenvironment interaction with the CD200R1 are proposed to exert both direct and indirect effects on T cell activation (FIG. 6).

Figure 18A:
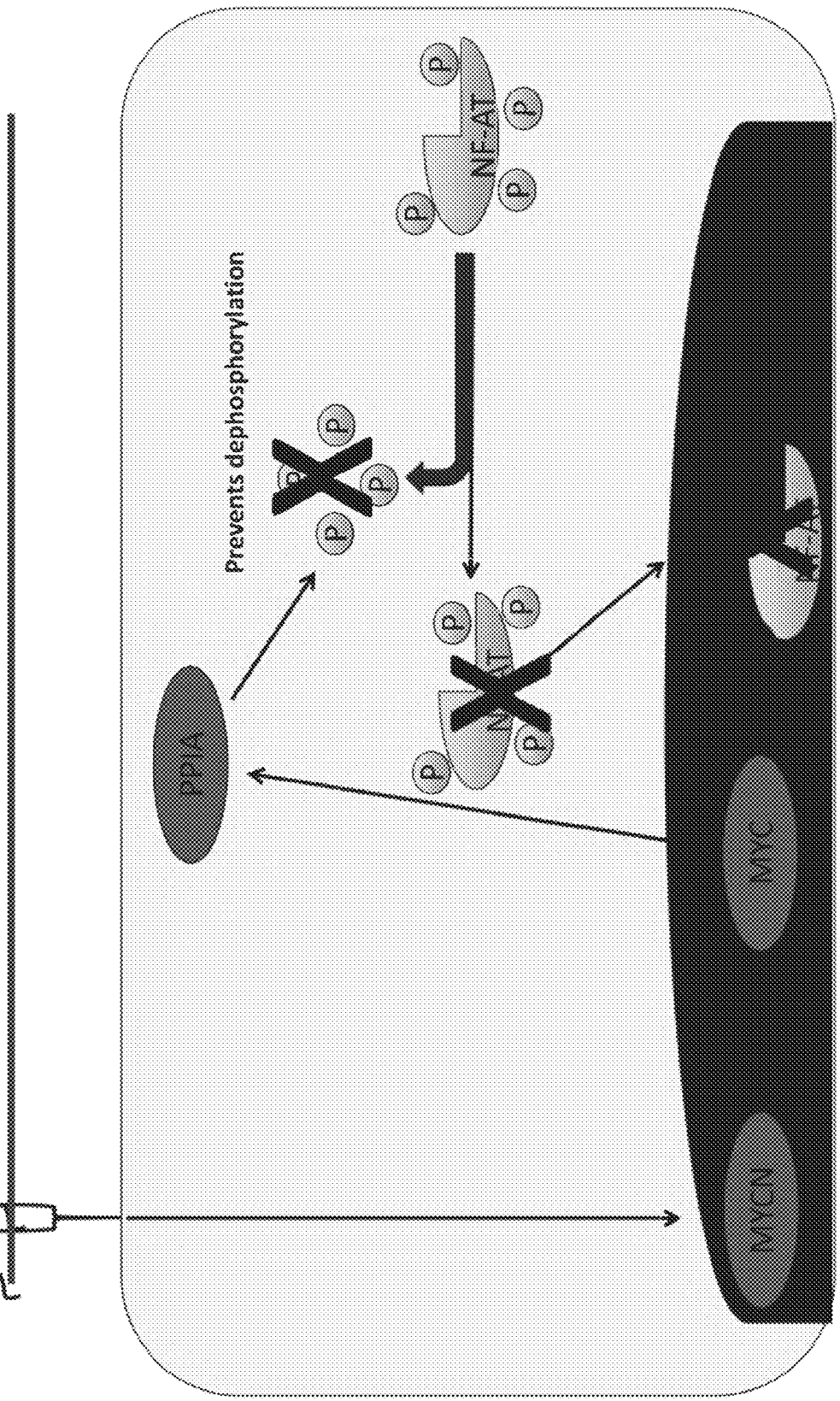
Figure 18B:
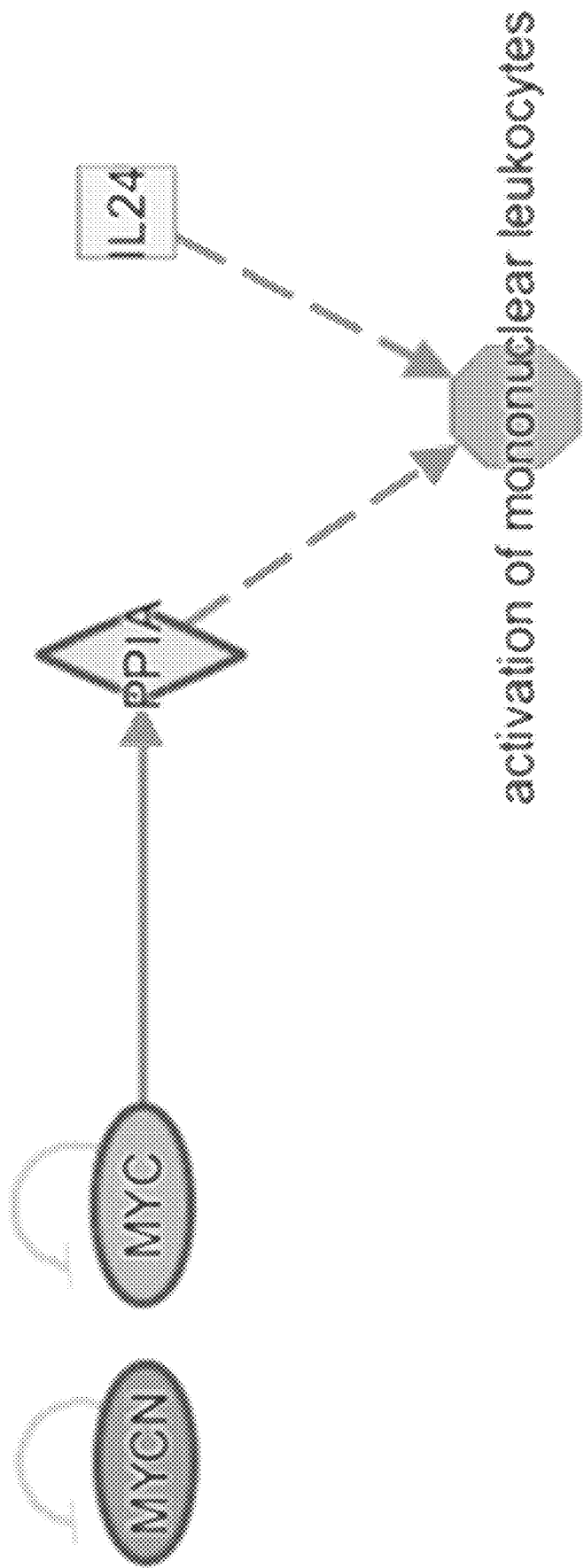
Figure 23:
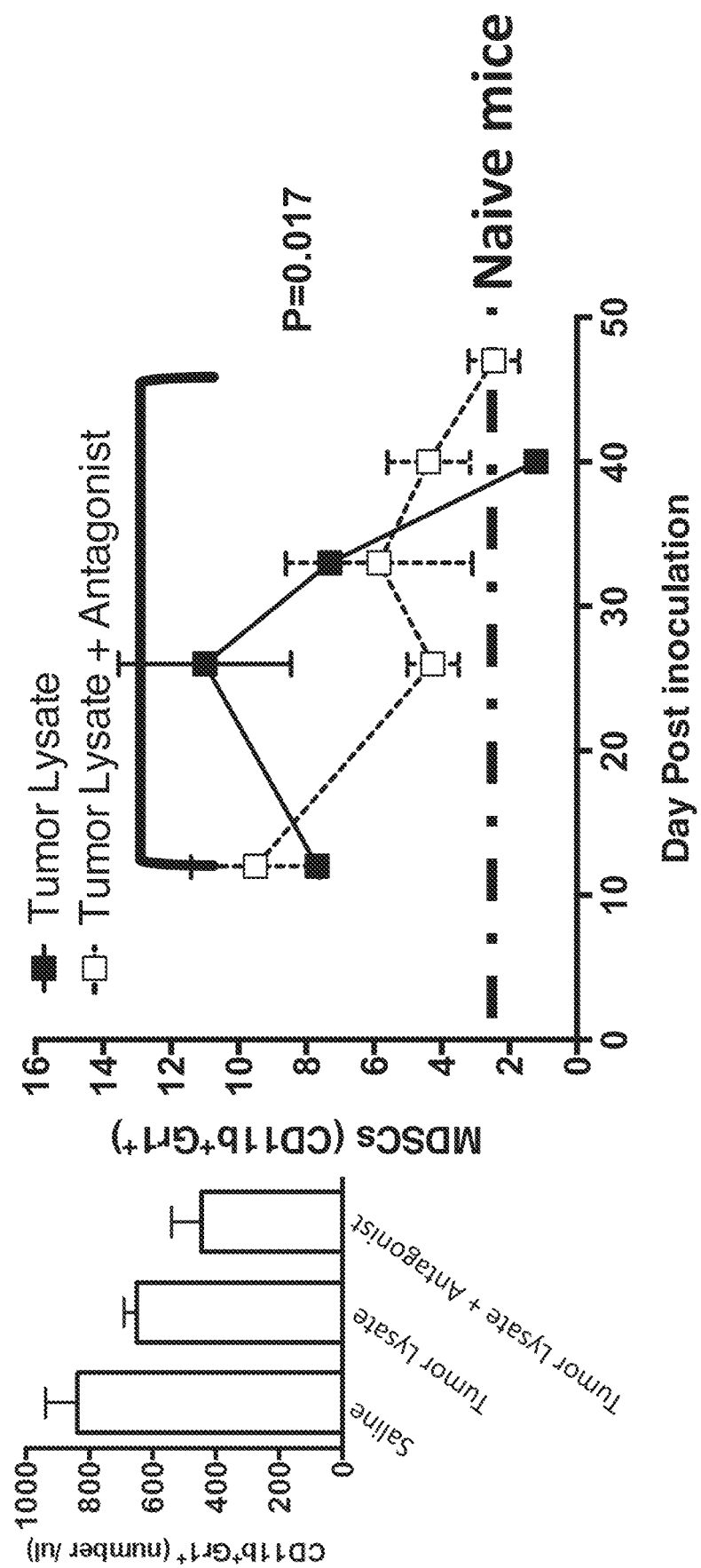
FIG. 23. Mice were vaccinated with tumor lysate+/− CD200 inhibitor. Mice were followed over time for MDSC populations. P value of 0.017 represents a significant difference in MDSC percentage between days 10 and 50 In mice receiving antagonist.
Figure 24:
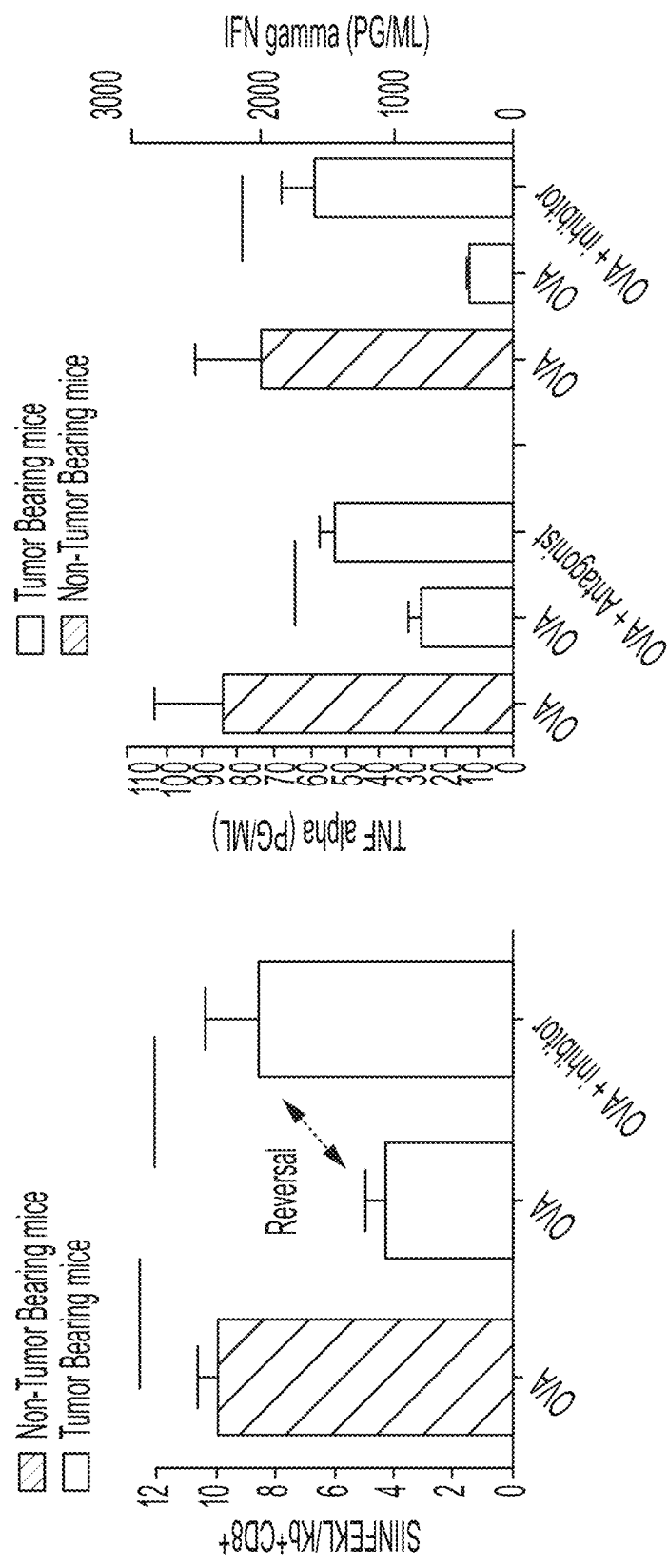
FIGS. 24A-24B. Tumor bearing or non-tumor bearing mice were vaccinated with OVA+ and adjuvant Poly: ICLC+/−CD200 inhibitor P1A12. Mice were sacrificed and lymphocytes were measured for OVA specific T-cell proliferation (FIG. 24A). Lymphocytes were restimulated with OVA, supernatants were measured for cytokine production (FIG. 24B).

Although multiple graft rejection studies have determined CD200 to be immunosuppressive, Gorczynski et.al. reported that specific peptide domains within the CD200 protein have agonist (exhibit the same immune-suppressive effects) or antagonist (act as competitive inhibitors for CD200) activity for the CD200R (Gorczynski et al., J Surg Res 2008; 145(1): 87-96). These antagonist have been reported to reverse the differentiation to as myeloid-derived suppressor cells following interaction with soluble CD200 (FIG. 18C) (Moertel et al., J Immunother Can; 2(1):46) and in vivo (FIG. 23). The mechanism of CD300 protein inhibition has been determined through the upregulation of an immunosuppressive protein PPIA (FIGS. 18A-18E) which is inhabited with the use of the CD200 inhibitor P1A12.

Figure 3B:
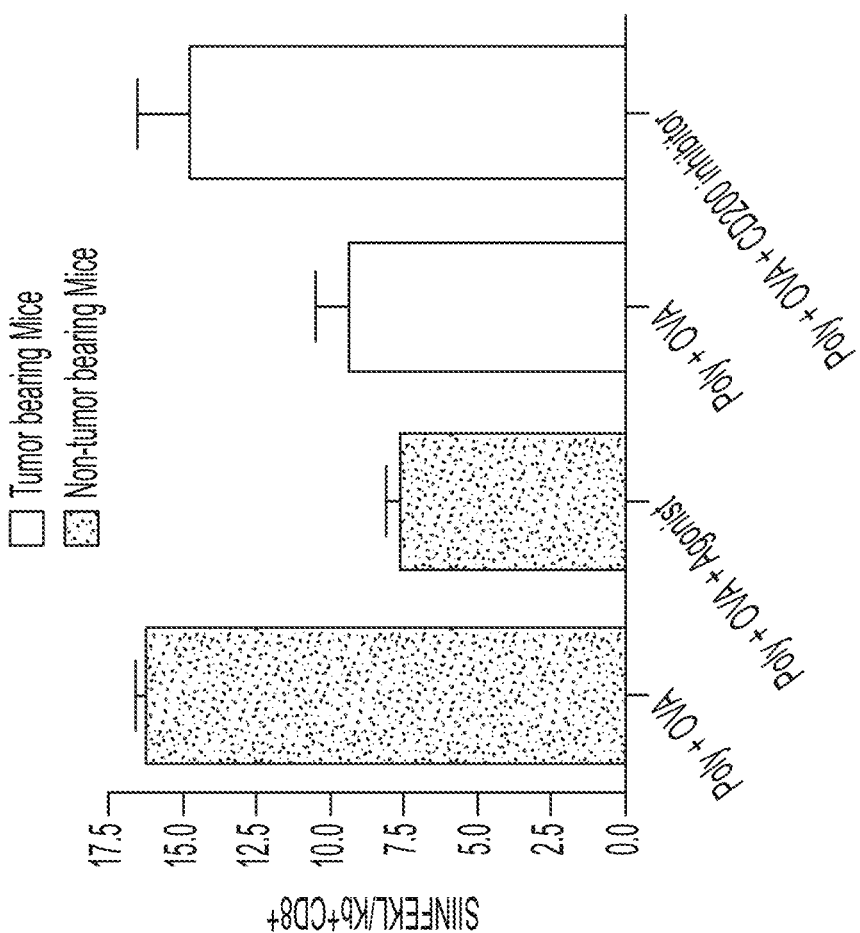
FIGS. 3A-3B.
Figure 3A:
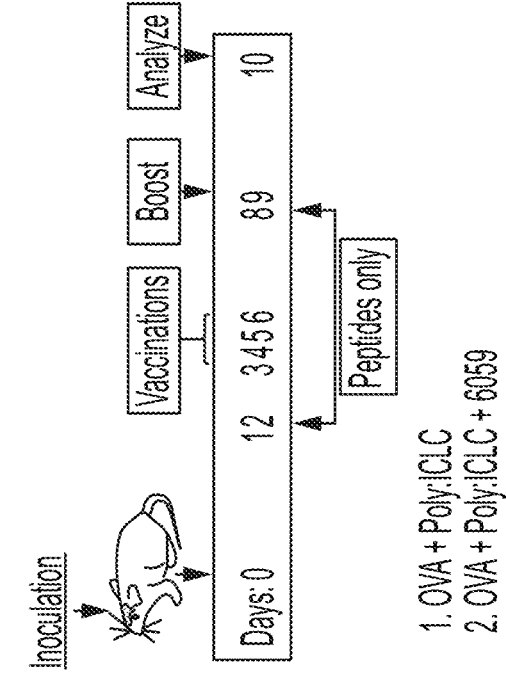

Gorczynski et.al. described agonist and antagonist peptides derived from CD200, now described as CD200 inhibitor by Xiong et al., 2016; Immunity, 13(2) 233-242). To determine if agonist peptides mimicked immune suppression elicited by intact CD200, select agonists were mixed with OVA and wildtype (non-tumor-bearing) CD57BL/6 mice were immunized in a prime-boost model (Ohlfest et al., J Immunol 2013; 190(2): 613-20). These CD200-derived agonists suppressed antigen-specific CD8$^+$ T cell proliferative responses in non-tumor-bearing mice to levels equivalent to those routinely seen in tumor-bearing mice (FIGS. 3A-3B). These data support the proposal that CD200 suppresses antigen-specific CD8$^+$ T cell responses as described herein.

Figure 7:
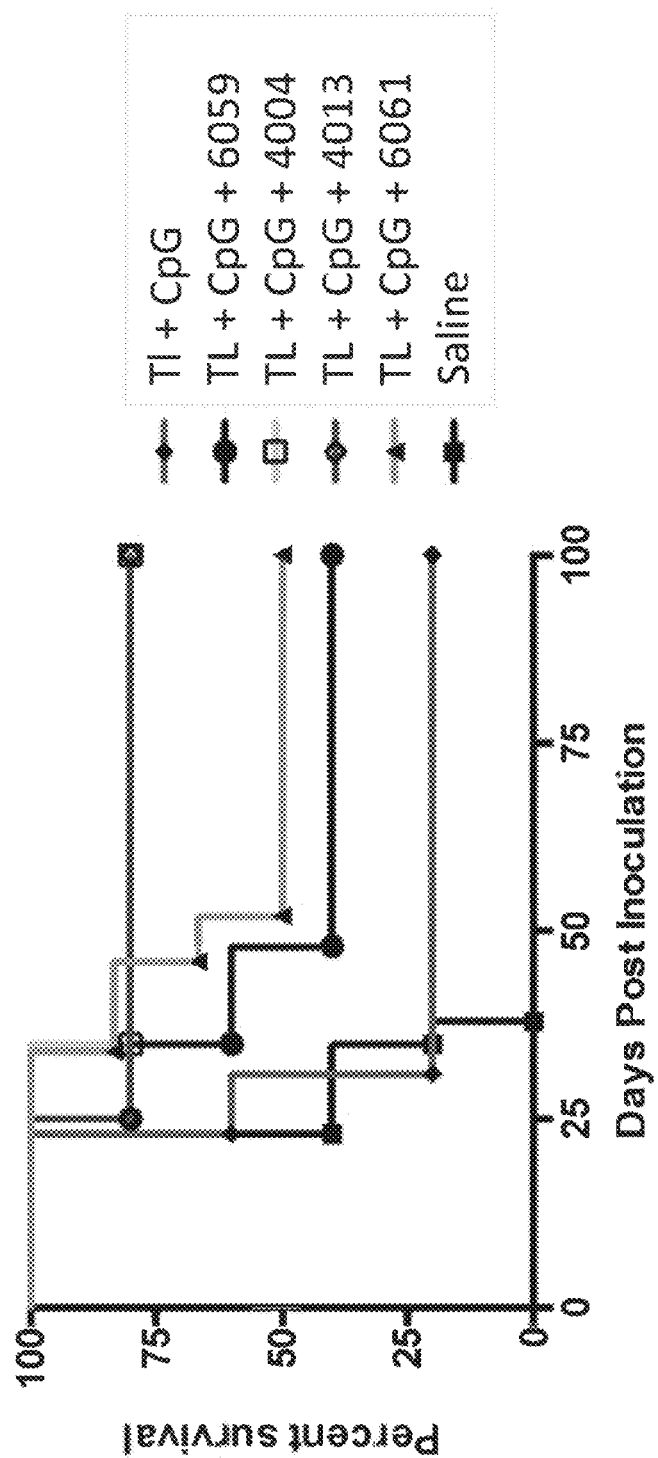
FIG. 7. Different CD200 inhibitor induces alternant immune responses. A) GL261 or B) EMT6 breast tumor-bearing mice were given different murine CD200 inhibitors. C) Human immature dendritic cells were given different CD200 inhibitors. Inhibitor numbers represent in-house nomenclature. Further analysis determined that different CD200 inhibitors bind to different murine CD2000 activation receptors eliciting different immune responses.
Figure 8:
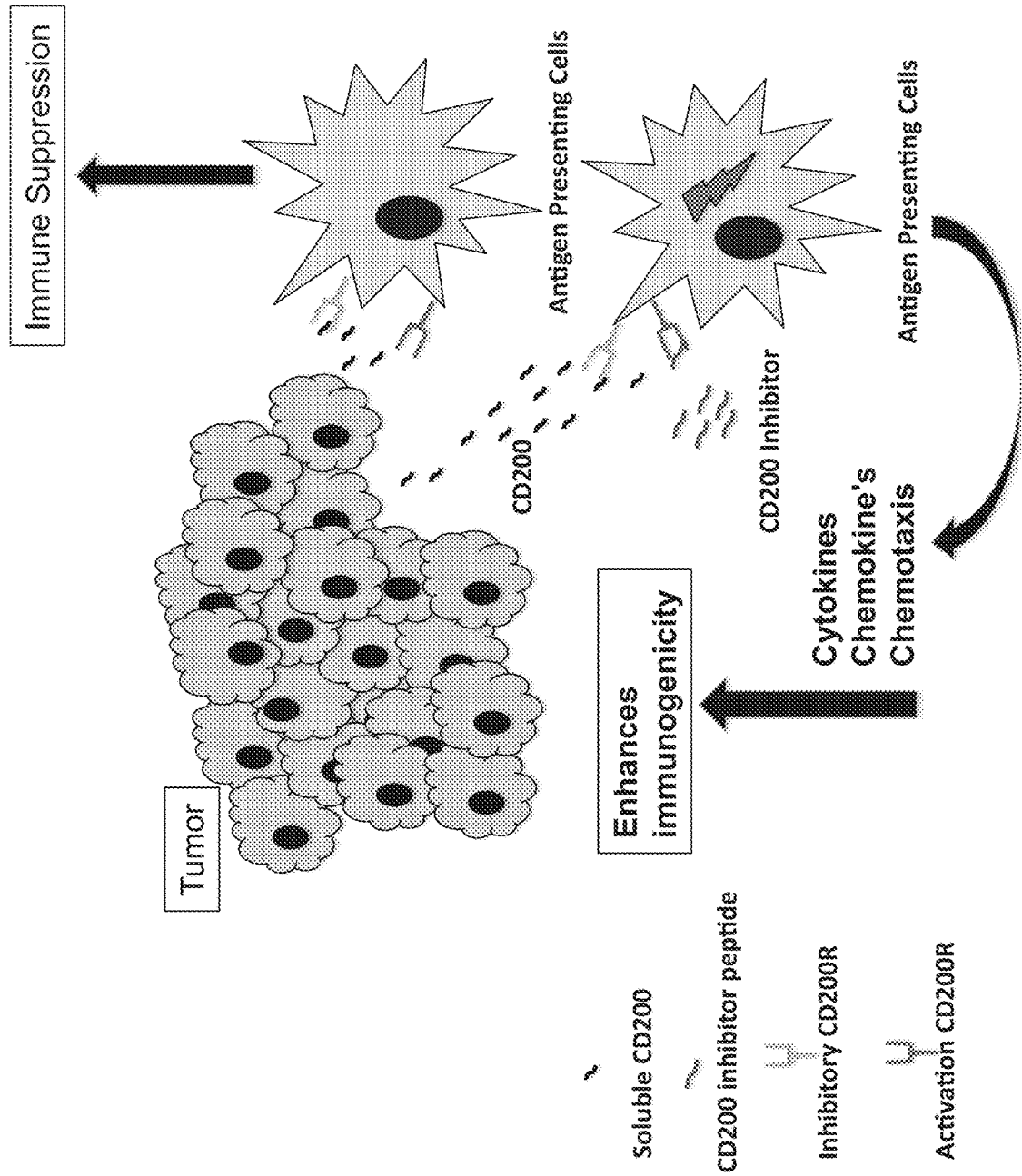
FIG. 8. Scheme illustrating consistent delivery of soluble CD200 from the CNS, which will enhance CD200-mediated immunosuppression in the draining lymph nodes. The addition of our CD200 inhibitor binds to the CD200 activation receptor activating the cell overpowering the inhibitory signals of soluble CD200.
Figure 9B:
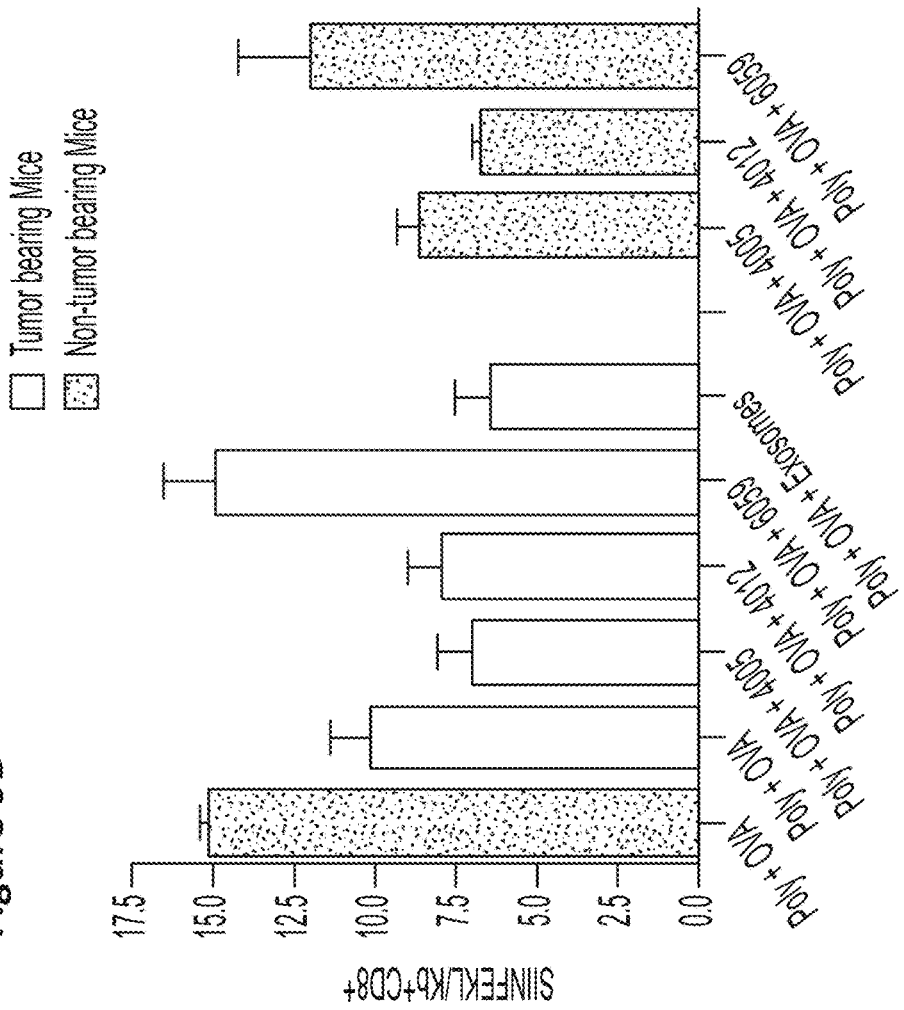
FIGS. 9A-B.
Figure 9A:
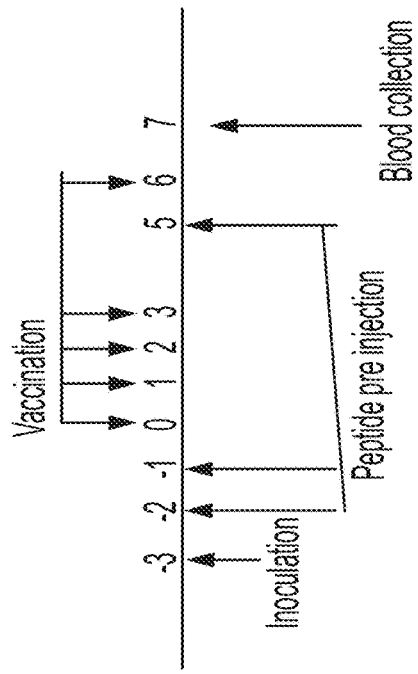
Figure 10:
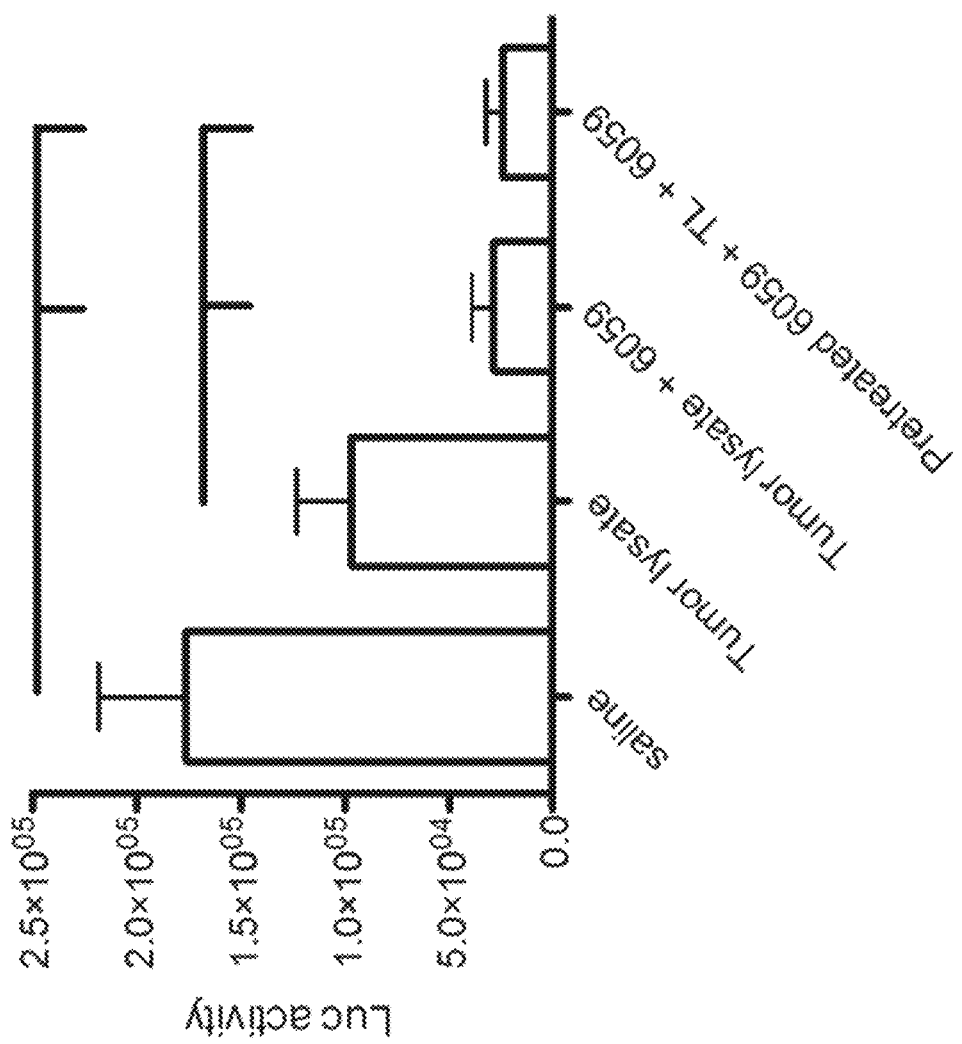
FIG. 10. In vivo survival study. Four groups were studied for tumor growth: (1) Saline; (2) Tumor lysate; (3) Tumor Lysate+CD200 inhibitor 6059; (4) Pretreated mice with CD200 inhibitor 6059 only 2 days prior to vaccination with tumor lysate+CD200 inhibitor 6059. All vaccinations were administered in the back of the neck in tumor bearing mice.

Whether the different antagonists described by Gorczynski et.al. (J Surg Res 2008; 145(1): 87-96) could modulate or reverse the suppressive effects of the tumor microenvironment was also investigated (J ImmunTher Can 2014; 2 (1) 46. It was concluded that different antagonists either act through different CD200R isoforms or have different biological effects on the same receptor as shown in a murine breast tumor, glioma, and with human model (FIGS. 7A-7B). They demonstrated that the optimal inhibitor for glioma tumors had incremental survival benefits in breast cancer, In contrast, the inhibitor that resulted in approximately 80% survival in our breast cancer model had no significant affect in our glioma model. Differential immune responses were also found between two human CD200 inhibitor peptides we are testing.

Figure 11A:
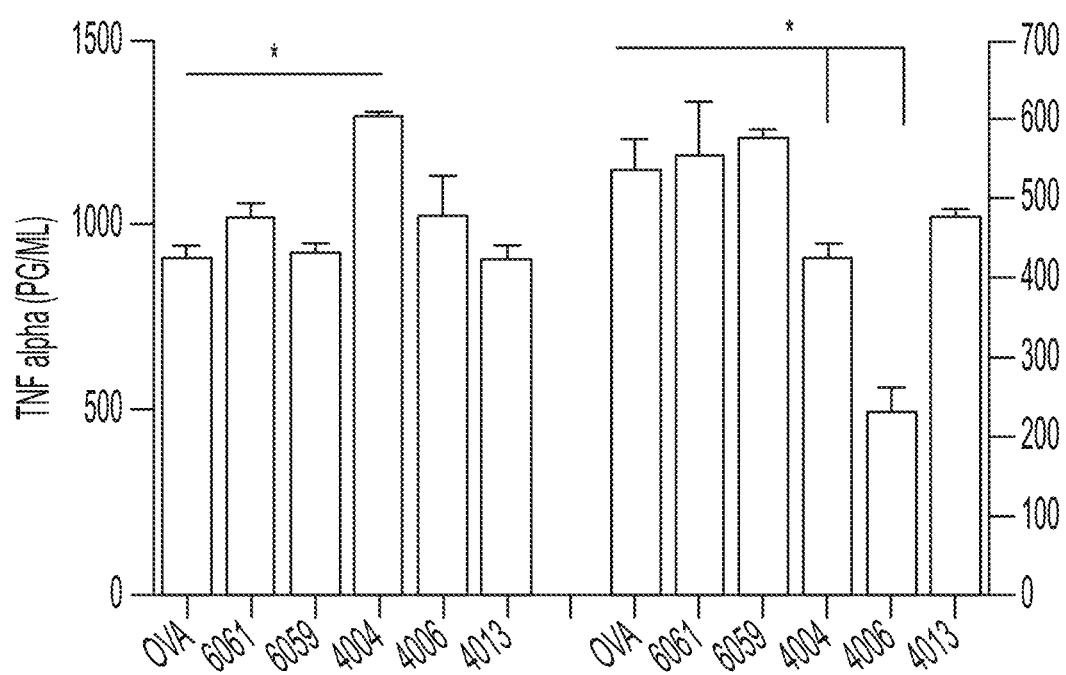
FIGS. 11A-11B. Splenocytes were pulsed with OVA+an inhibitor peptide and incubated for 24 h. Following incubation, cells were washed, purified OT1 were added to wells and incubated for an additional 48 hours then analyzed for FIG. 11A) TNFa and IL-6 production.
Figure 11B:
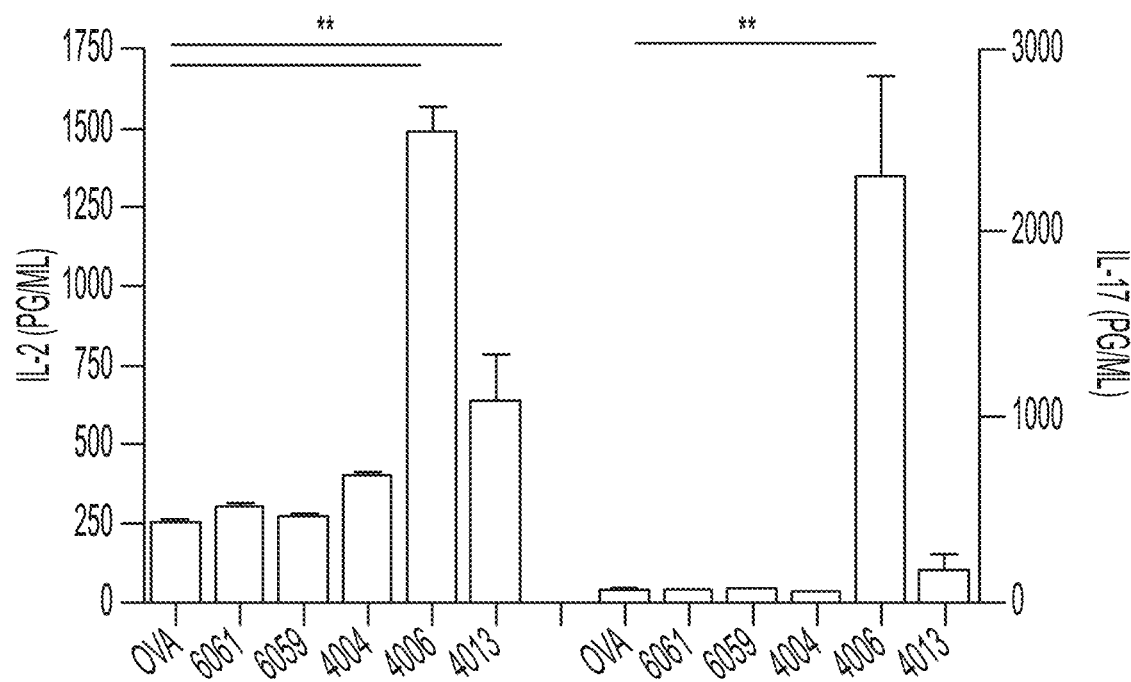

Clustal Omega program indicates that the 3 different murine CD200 inhibitors (P1=P1A12, P2=4013 and P3=4006, Table 1) have higher binding specificity to different activation receptors. The P3 inhibitor has higher binding specificity to receptor R2, P2 has higher binding specificity to receptor R3 and P1 has higher binding specificity to receptor to R4. We hypothesize that the two different human CD200 inhibitor peptides (peptide 1=hP1 & peptide 2=hP2, table 2) are hitting different activation receptors on dendritic cells, although only one has been identified. This demonstrated the importance of understanding the different immune responses directed by our inhibitors. We want to generate the immune response most beneficial for our patients. These conclusions were supported by experiments where splenocytes were pulsed with OVA+selected CD200 inhibitors (6061, 6069, 4004, 4006, 4013) for 24 hours. The splenocytes were then washed and cultured for 48 hours with the addition of OT-1 T cells. The cultures were then assessed for cytokine production using a Flow cytometric bead array. It was found that different cytokine profiles were elicited by inhibitors 4004 and 4006 compared to the others (FIGS. 11A-11B).

Whether the CD200 inhibitors were capable of modulating/reversing the suppressive effects the tumor exhibits in the cervical lymph nodes was subsequently investigated. It was concluded that the addition of an inhibitor reversed tumor induced suppression. This conclusion was determined by vaccinating mice with OVA+the inhibitor peptide 6059 in a prime boost model (Ohlfest et. al., (J Immunol 2013; 190(2): 613-20) (FIG. 12A). We demonstrated a strong suppressive effect as routinely seen in tumor-bearing mice (FIG. 12A). To validate our observations, lymphocytes were harvested from the cervical lymph nodes of the inhibitor 6059 treated mice and restimulated with the OVA peptide SIINFEKL (SEQ ID NO: 18). After 48 hrs, the culture supernatant was analyzed for cytokine production demonstrating the ability of the antagonist to modulate/reverse glioma-induced suppression (FIGS. 4A-4B). Interestingly, vaccinating non-tumor bearing mice with OVA+glioma-derived exosomes+the antagonist 6059 partially reversed the suppression induced by exosomes (FIG. 12C). These experiments support the hypothesis that exosomes express the CD200 protein thereby inhibiting the ability to prime a T cell response in the draining lymph nodes of glioma bearing mice. Other CD200 inhibitors were similarly evaluated (FIGS. 3A-3B, 9A-9B and 24A-24B).

Figure 5A:
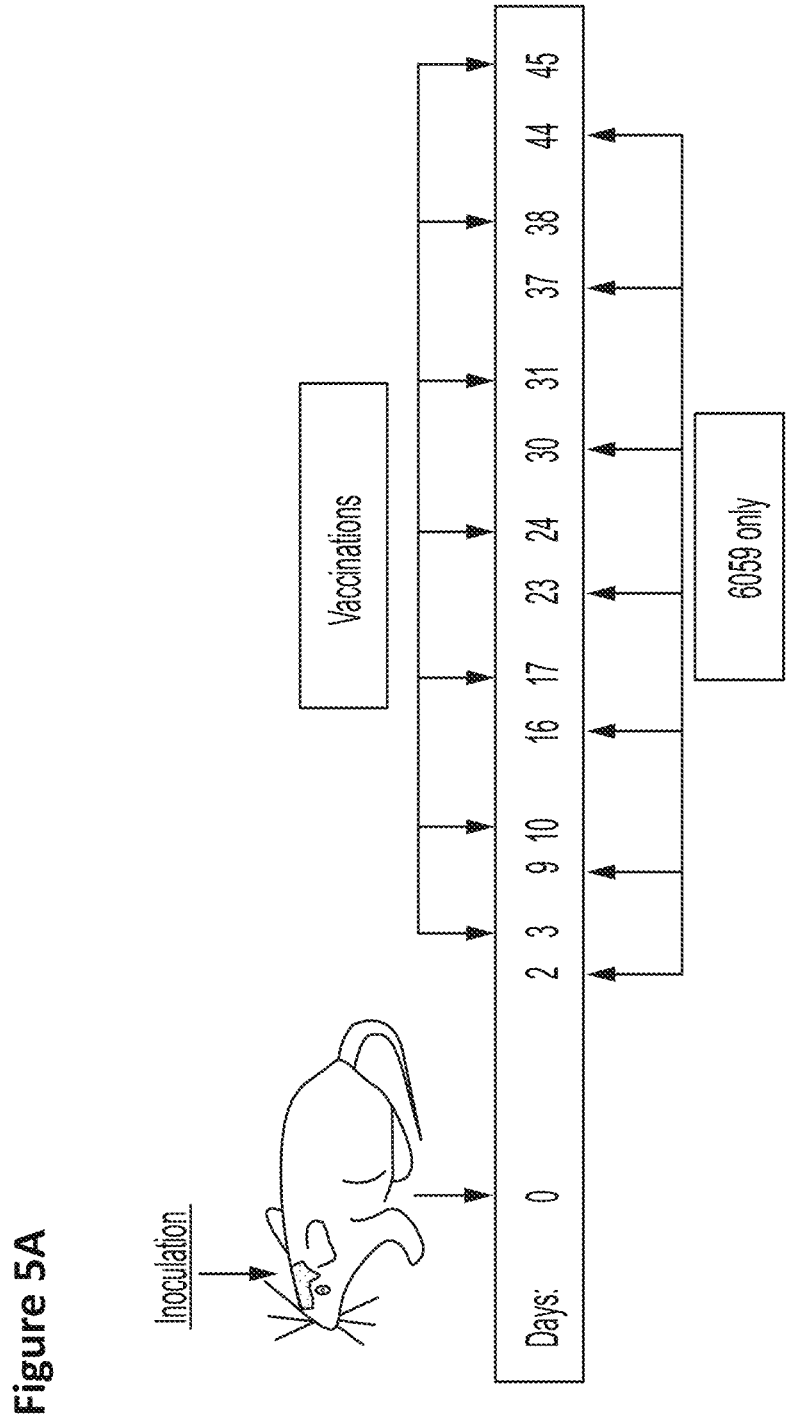
FIGS. 5A-5C.
Figure 5C:
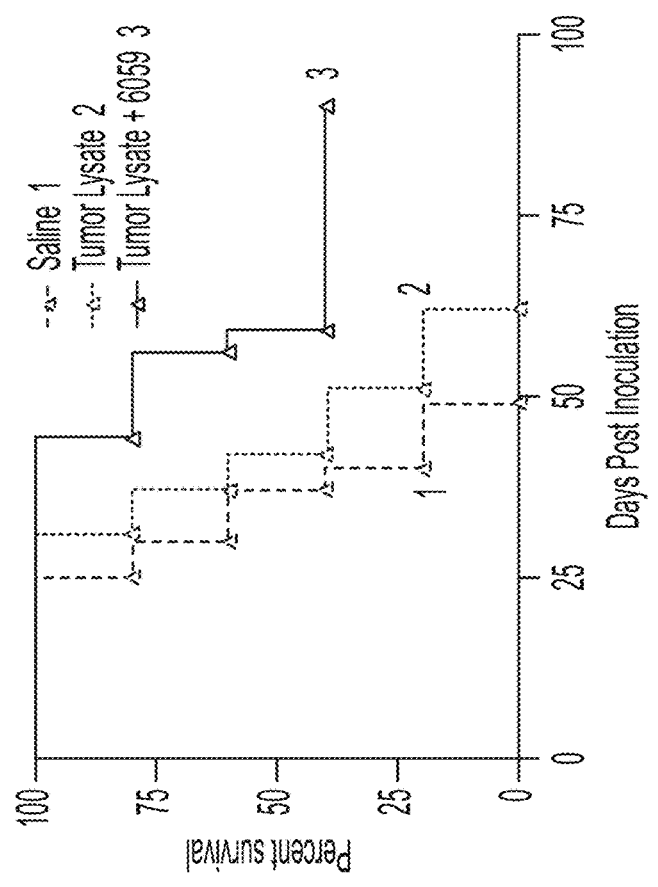
Figure 5B:
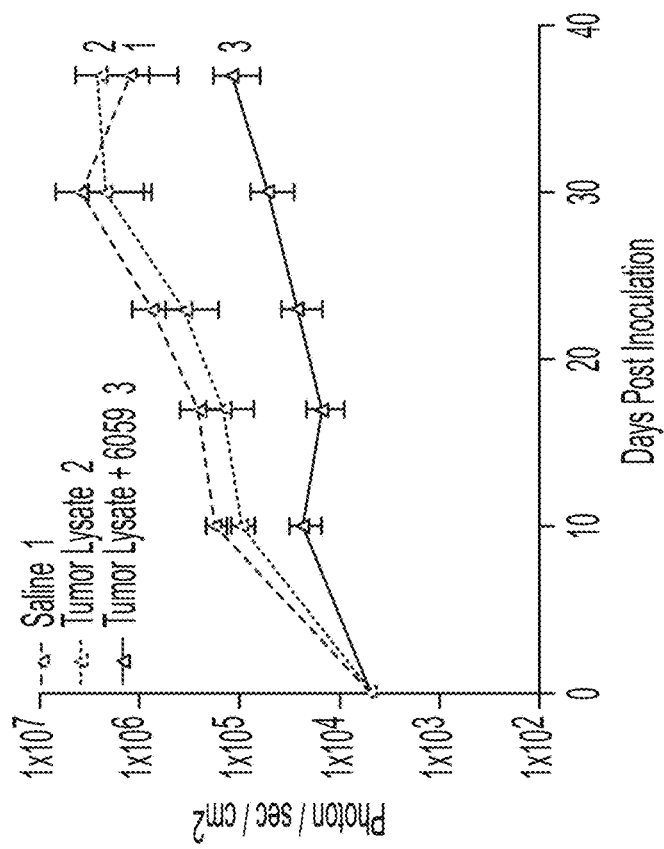
Figure 17A:
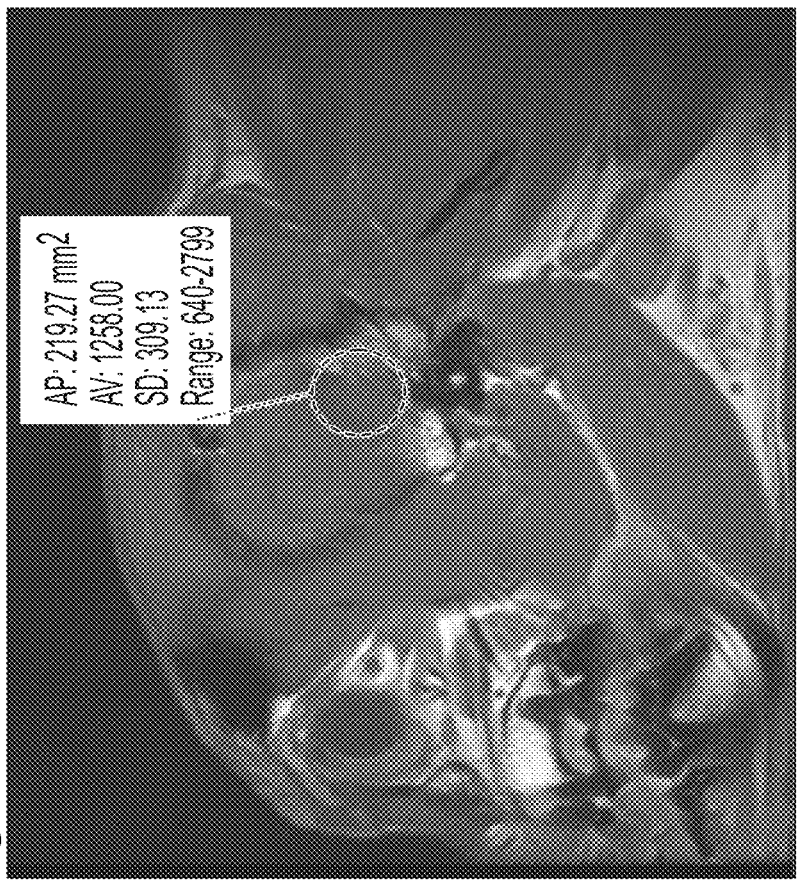
Figure 17B:
Figure 17E:
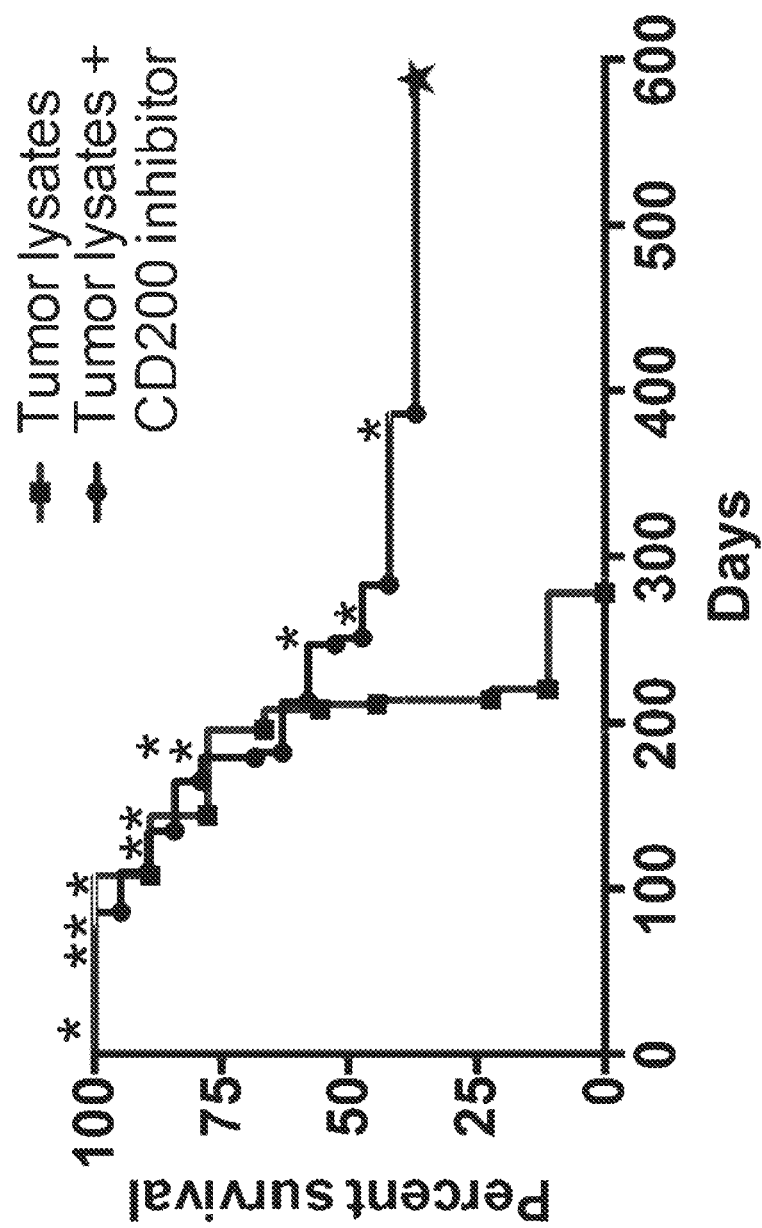

Whether vaccination with CD200 inhibitor could enhance the survival of tumor-bearing mice was also studied. It was concluded that the addition of the inhibitors enhances survival benefit in the GL261 model (FIG. 5A). GL261 tumor bearing mice were vaccinated weekly with saline, tumor lysates (TL) or tumor lysates+an inhibitor (6059). These experiments show that tumors grow faster in mice vaccinated with saline or tumor lysate alone compared to mice vaccinated with tumor lysate plus an inhibitor (data not shown) resulting in an increased survival benefit in the GL261 (FIG. 5A) model resulting in extended survival (FIG. 5B). These results translated to a breast carcinoma (EMT6) model (FIG. 7B) tumor model. In addition, a canine specific CD200 inhibitor demonstrated an enhanced survival benefit. Privet pet come to the University of Minnesota veterinary clinic diagnosed with high-grade gliomas were given autologous tumor lysates or tumor lysates+canine specific CD200 inhibitor. Within 4 months, some of the dogs with remaining tumor demonstrated total regression (FIGS. 17A-17D) resulting in enhanced survival (FIG. 17E).

Figure 26B:
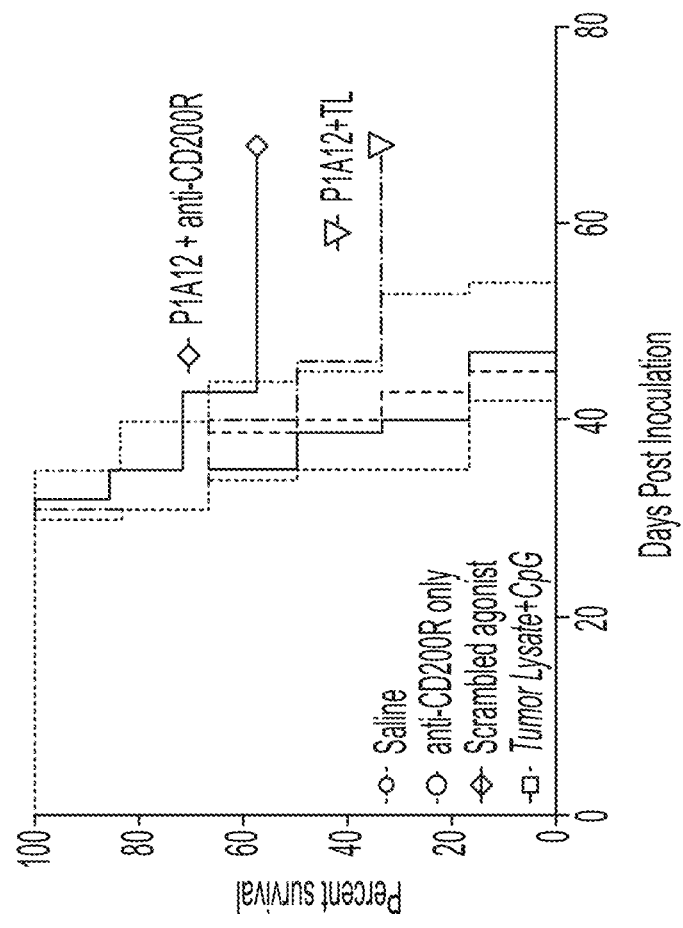
FIGS. 26A-26B. A polyclonal antibody (anti-CD200R) was generated against for the same epitope site on the CD200 receptor as the P1A12 mouse antagonist (Fisher Scientific). The antibody was specifically designed against the same epitope as the P1A12 antagonist to avoid the induction of immune suppression.
Figure 26A:
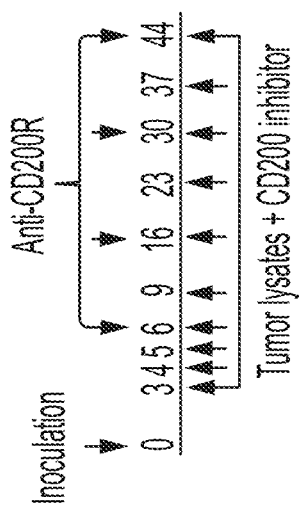

The CD200 peptide inhibitors are designed to activate antigen-presenting cells, however, activated T cells need protection from soluble CD200. Anti-CD200 receptor developed for a specific epitope was given systemically following vaccination with tumor lysates+CD200 inhibitor P1A12 and followed for survival (FIGS. 26A-26B).

Optimization of the Competitive Inhibitors

One of the major hurdles in cancer immunotherapy is overcoming immunosuppression in both the tumor microenvironment and sentinel lymph nodes. Described herein is the optimization of the CD200 inhibitor peptide domains to overcome tumor-induced immunosuppression in both the sentinel lymph nodes and the tumor microenvironment.

Using mixed leukocyte reactions, Gorczynski et.al. (J Surg Res 2008; 145(1): 87-96) reported that specific regions of the CD200 protein act as agonists or act as antagonists (also described herein as "CD200 inhibitors"). Mice express five isoforms of the CD200R that exhibit tissue-restricted expression and heterogeneity of function (Wright G J, Cherwinski H, Foster-Cuevas M, et al. Characterization of the CD200 receptor family in mice and humans and their interactions with CD200. J Immunol 2003; 171(6): 3034-46; Gorczynski R, Boudakov I, Khatri I. Peptides of CD200 modulate LPS-induced TNF-alpha induction and mortality in vivo. J Surg Res 2008; 145(1): 87-96; Gorczynski R, Chen Z, Kai Y, Lee L, Wong S, Marsden P A. CD200 is a ligand for all members of the CD200R family of immunoregulatory molecules. J Immunol 2004; 172(12): 7744-9; Gorczynski R M, Chen Z, Clark D A, et al. Structural and functional heterogeneity in the CD200R family of immunoregulatory molecules and their expression at the fetomaternal interface. Am J Reprod Immunol 2004; 52(2): 147-63). The different inhibitors may work through different receptors resulting in different biologic responses. The experiments described herein determine if the different inhibitors work through alternative pathways allowing the potential use of multiple inhibitors that may synergize with each other, thereby enhancing the ability to induce a tumoricidal response.

Methods: Since mice have five identified CD200Rs, we need to determine if the CD200-derived peptide inhibitors function through multiple receptors. Accordingly, wildtype splenocytes will be blocked using anti-CD200R1, anti-CD200R2, anti-CD200R3, or anti-CD200R1 (Gorczynski R, Lee L, Boudakov I. Augmented Induction of CD4$^+$CD25$^+$ Treg using Monoclonal Antibodies to CD200R. Transplantation 2005; 79: 1180-83). Following incubation, cells are pulsed with OVA+Poly:ICLC in the presence or absence of recombinant mouse CD200Fc chimeric protein (rmCD200Fc, R&D Systems) with or without the addition of the individual peptides. Following a 24 hr incubation, purified OT-I CD8 T cells are added for 48 hr and then the supernatants are analyzed for Th1/Th2 cytokines using a flow cytometric bead array and TGFβ production by ELISA. To determine the effects the inhibitors have on restoration of a proliferative response, splenocytes are pulsed from wildtype mice with the same treatment groups as described above. Following a 24 hr incubation, purified CFSE labeled OT-I CD8 T cells are added to the cells. After 48 h incubation cells are analyzed by flow cytometry for proliferation. If appropriate, peptides are combined into a mixture to determine if blocking CD200 binding to multiple receptors enhances the immune response.

In summary, blood and cervical node lymphocytes are analyzed for SIINFEKL/K$^b$ specific CD8$^+$ T cells ("SIINFEKL" disclosed as SEQ ID NO: 18). Lymphocytes isolated from cervical lymph nodes are stimulated with a peptide containing the core OVA-derived SIINFEKL epitope ("SIINFEKL" disclosed as SEQ ID NO: 18) (EVSQLEQLE SIINFEKLTEEWTSSNVM). Supernatants are analyzed using a flow cytometric bead array (BD Bioscience) for the levels of Th1, Th2, and Th17 cytokines. A commercial ELISA assay (R&D Systems) is used to measure levels of TGFβ produced. A separate aliquot of cells is analyzed for surface expression of CD8 and SIINFEKL/K$^b$ binding ("SIINFEKL" disclosed as SEQ ID NO: 18) and intracellular expression IFN-γ$^1$.

Evaluate CD200/CD200R Interactions on the Ability of Dendritic Cells to Present Antigen.

Dendritic cells (DCs) are the most powerful known antigen-presenting cells. Dendritic cells patrol the tissues of the body for pathogens and signs of damage. Upon injection, tumor cells or cell components are taken up and processed by DCs in the skin and secondary lymphoid organs, which then bridge innate and adaptive immunity. CD200 binds to the CD200R1 on dendritic cells altering their functional response (Li Y, Zhao L D, Tong L S, et al. Aberrant CD200/CD200R1 expression and function in systemic lupus erythematosus contributes to abnormal T-cell responsiveness and dendritic cell activity. Arthritis Res Ther 2012; 14(3): R123).

Purified bone marrow derived DCs (BMDCs) are used for murine studies. Experimental endpoints include: i) co-stimulatory marker expression, ii) OVA cross presentation, and iii) cytokine production. To investigate the ability to translate to humans, iDC are pulsed with the CMV peptide pp65+ hCD200Fc+/−inhibitor. Experimental endpoints include i) co-stimulatory marker expression and ii) cytokine production.

In summary, BMDCs are matured using a protocol modified from Inaba et al. (Ohlfest J R, Andersen B M, Litterman A J, et al. Vaccine injection site matters: qualitative and quantitative defects in CD8 T cells primed as a function of proximity to the tumor in a murine glioma model. J Immunol 2013; 190(2): 613-20; Wick D A, Martin S D, Nelson B H, Webb J R. Profound CD8+ T cell immunity elicited by sequential daily immunization with exogenous antigen plus the TLR3 agonist poly(I:C). Vaccine 2011; 29(5): 984-93). Briefly, femurs and tibias are removed from C57BL/6 mice and flushed with PBS. Cells are washed and plated in complete RPMI 1640 containing 20 ng/mL GM-CSF. Non-adherent cells are removed and media replaced every three days. Six days post-bone, loosely adherent cells are harvested, washed and plated in 96 well plates at 100,000 cells/200 µl per well. Cells are pulsed with OVA+CpG, OVA+CpG+mCD200Fc, OVA+CpG+inhibitor, or OVA+CpG+CD200Fc+inhibitor. CD200Fc is given 30 minutes prior to pulsing. Non-pulsed wells are used as a control. Following 24 hr incubation, dendritic cells are stained with antibodies to CD11c, CD86, CD80, and HLA-II and analyzed by flow cytometry. Supernatants are analyzed for IL-6 and IL-12 production. To test for the effects of CD200 on OVA cross presentation, DCs are stained with 25-D1.16 to measure antigen expression. 25-D1.16 is a monoclonal antibody that specifically binds SIINFEKL (SEQ ID NO: 18) only when presented by H-2K$^b$. 5×10$^5$ HLA-A2$^+$ immature DCs derived from CD14$^+$ peripheral blood monocytes are pulsed with 10 g of the CMV peptide pp65$_{495-503}$ (NLVPMVATV (SEQ ID NO: 20))+/− hCD200Fc+/−inhibitor.

Determine the CD200 Derived Competitive Inhibitors Mechanism(s).

It has been demonstrated using a prime boost model that the inhibitor peptide 6059 reversed the suppressive effects in tumor-bearing mice.

In the following experiments, wildtype mice are inoculated with GL261 cells and vaccinated. Mice will be vaccinated with i) saline, ii) 65 µg of GL261 tumor lysate tumor lysate, or iii) 65 µg of GL261 tumor lysate tumor lysates+ optimized Inhibitors. Experiments are performed as described above. We will study the effects of our novel inhibitors on: i) T cell expansion, ii) cytokine response and iii) cytolytic response observed in the cervical lymph nodes, iv) lymphocyte infiltration and caspase 3/7 activity, v) development of immunological memory, and vi) survival benefit. Moreover, this work is translated to our human T cell response using a CMV assay as described by Olin et al. (Olin M R, Andersen B M, Litterman A J, et al. Oxygen is a master regulator of the immunogenicity of primary human glioma cells. Cancer Res 2011; 71(21): 6583-9).

In summary, the effects on T cells were studied by measuring SIINFEKL specific T cell expansion ("SIINFEKL" disclosed as SEQ ID NO: 18), recall response measured by cytokine production and the generation of a CTL response. Moreover, mice (n=10/treatment group) are inoculated with luciferase-expressing GL261 glioma cells as described and vaccinated with i) saline, ii) tumor lysate, or iii) tumor lysates+optimized inhibitors on days 3, 10, 17, 24, and 31. In a separate experiment, a group of mice (n=6) are sacrificed on days 7 and 14. Brains are harvested and analyzed by immunohistochemistry for CD3 infiltration and active caspase activity as described by Olin et al. (Olin M R, Andersen B M, Zellmer D M, et al. Superior efficacy of tumor cell vaccines grown in physiologic oxygen. Clin Cancer Res 2010; 16(19): 4800-8). In a second group of mice (n=5), brain infiltrating lymphocytes will be harvested as previously described (Ohlfest J R, Andersen B M, Litterman A J, et al. Vaccine injection site matters: qualitative and quantitative defects in CD8 T cells primed as a function of proximity to the tumor in a murine glioma model. J Immunol 2013; 190(2): 613-20) and phenotyped for CD4 or CD8 populations. In addition, mice are imaged weekly and monitored for survival. Following survival (100 days post inoculation), mice are re-inoculated with GL261 in the contralateral hemisphere and followed for survival. Newly inoculated mice (no vaccination) are used as a control. Further, $5 \times 10^5$ HLA-A2$^+$ CMV$^+$ immature DCs derived from CD14$^+$ peripheral blood monocytes are pulsed with 10 μg of the CMV peptide pp65$_{495-503}$ (NLVPMVATV (SEQ ID NO: 20))+/−hCD200Fc or OVA+CD200Fc+CD200 inhibitor (FIG. 15). Cells are matured as described previously (Olin M R, Andersen B M, Litterman A J, et al. Oxygen is a master regulator of the immunogenicity of primary human glioma cells. Cancer Res 2011; 71(21): 6583-9; Inaba K, Inaba M, Romani N, et al. Generation of large numbers of dendritic cells from mouse bone marrow cultures supplemented with granulocyte/macrophage colony-stimulating factor. J Exp Med 1992; 176(6): 1693-702). Following maturation, $5 \times 10^5$ PBMCs from same donor are added and cultured for 48 hours. Supernatants are analyzed for IFNγ and granzyme B production by cytometric bead array (BD Biosciences) (Olin M R, Andersen B M, Litterman A J, et al. Oxygen is a master regulator of the immunogenicity of primary human glioma cells. Cancer Res 2011; 71(21): 6583-9). CMV sera-negative PBMCs are used as a control. All experiments are run in triplicate. The ANOVA analysis of the data is performed using the Bonferroni multiple comparison test (with control), as well as the Dunnett's two-sided multiple comparison test (also with control), for parametric variables, and in the case of non-parametric variables, using the Kruskal-Wallis ANOVA with the Kruskal-Wallis multiple comparison z-value test (Dunn's test).

Example 2

Overcoming the Immunosuppressive Effects of the Tumor Microenvironment within the Central Nervous System Even if the inhibitors are used to prime a T cell response in lymph nodes, the activated T cells encounter an immunosuppressive tumor microenvironment. To alleviate this hurdle, suppression of the tumor effects in the microenvironment is sought.

Figure 14A:
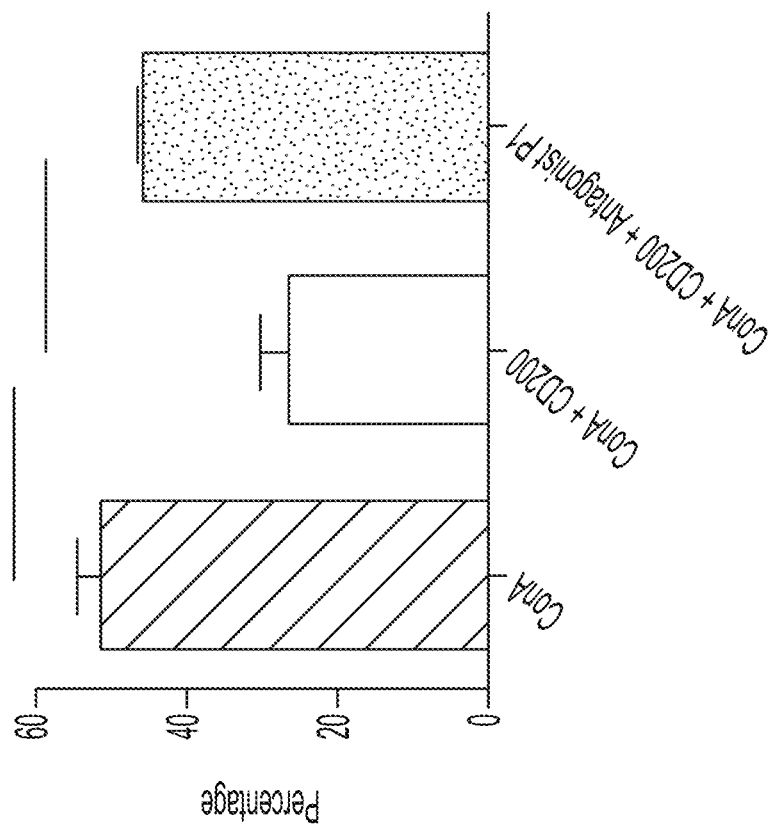
FIGS. 14A-14B. CFSE labeled human PBMCs were pulsed with ConA; ConA+hCD200; or ConA+hCD200+ CD200 inhibitor. Cells were analyzed by flow cytometry 48 hours later.
Figure 14B:
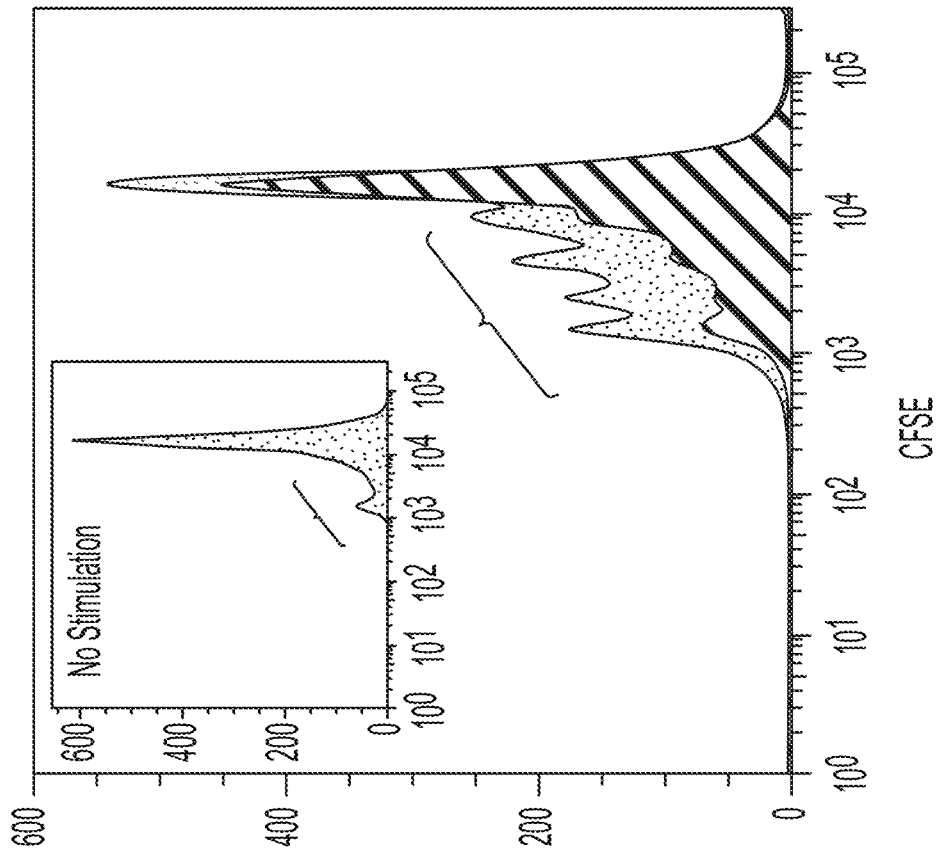
Figure 25:
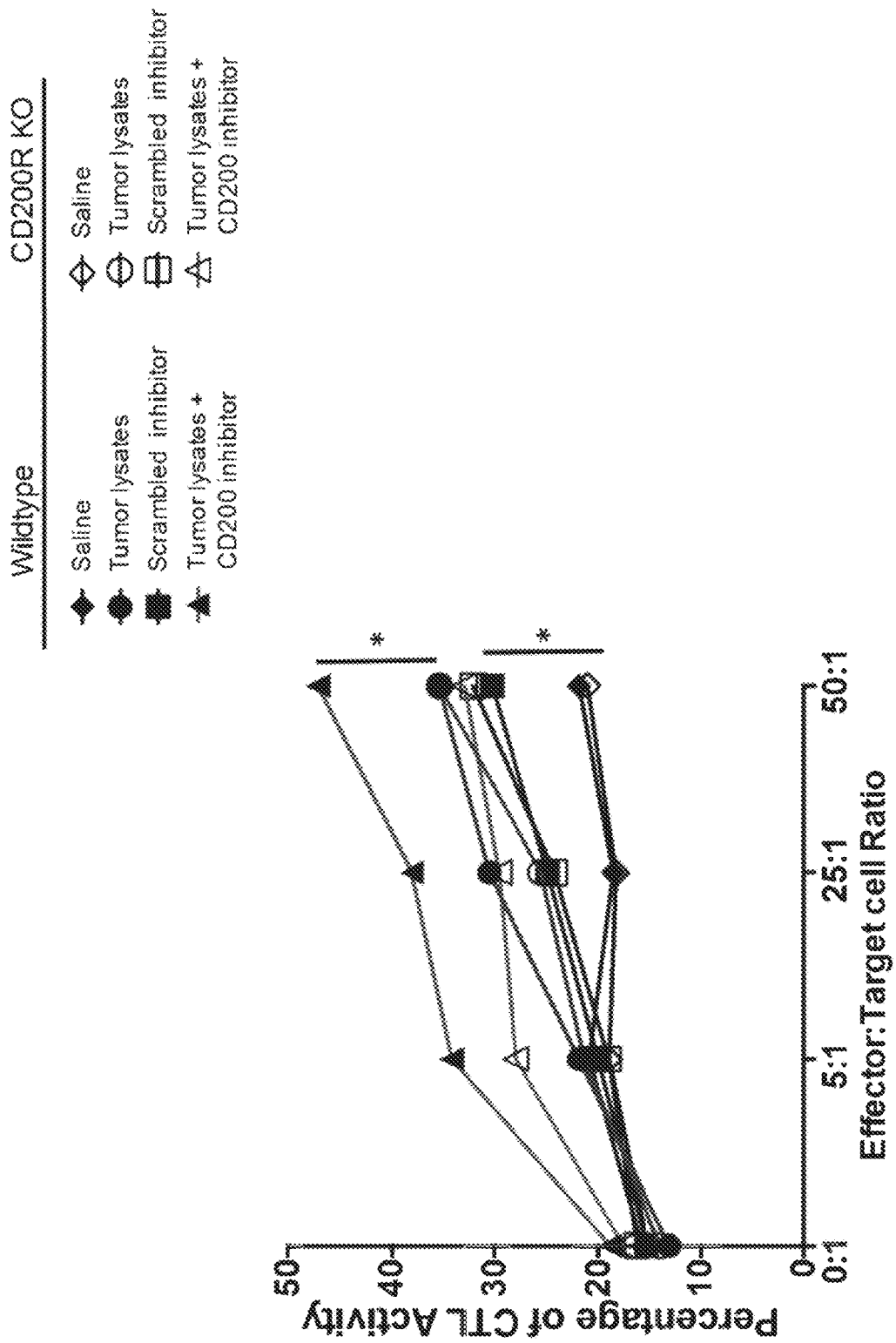
FIG. 25. Wildtype and CD200R knock out mice were vaccinated on days 4-7, 15 and 22. Lymphocytes from draining lymph nodes were harvested and incubated with GL261 cells at various effector:target cell ratios and analyzed for a cytolytic response.

Patients with glioblastoma exhibit systemic immune suppression effecting resulting in deficient adaptive immune responses. These deficiencies are due to the enriched immunosuppressive factors secreted by the tumor suppressing T cell proliferation (FIGS. 14A-14B) and cytotoxic function (FIG. 25). Immunosuppression plays an important role in tumor progression in patients with glioblastoma. Reversing immune suppression to provide an effective immune targeting allows patients with glioma to have less tumor progression and improved outcomes.

It has been found that the inhibitors can reverse or modulate the immunosuppressive tumor microenvironment. Tumor-bearing mice were inoculated in the brain with 10 μg of the inhibitor 6059 at the same coordinates at which the tumor was injected two days previously. This was followed by weekly injections of tumor lysate+inhibitor (FIGS. 5A-5B). Tumor growth was delayed in mice receiving the 6059 inhibitor.

The inventors have been focusing on CD200 competitive inhibitors to overcome the suppressive effects of the tumor in the draining lymph nodes. However, even if a tumoricidal response is enhanced, the suppressive properties of the tumor microenvironment decrease the cytolytic response.

The optimized CD200 inhibitor peptide is tested in the CNS of tumor bearing mice. 15,000 luciferase expressing GL261 cells are inoculated as described above. Adenovirus is inoculated using the same coordinates as tumor on day 2 post glioma inoculation. On day 4, mice are vaccinated subcutaneously in the back of the neck with a combination of i) tumor lysates+Poly:ICLC (tumor lysate column), ii) inhibitors with tumor lysates+Poly:ICLC (with vaccine column) or iii) adenovirus in the CNS (in CNS column) as outlined in Table 3.

TABLE 3

|  | Tumor Lysate | With vaccine | In CNS |
|---|---|---|---|
| Group 1 | − | − | − |
| Group 2 | + | − | − |
| Group 3 | + | + | − |
| Group 4 | + | − | + |
| Group 5 | + | + | + |

All mice receiving tumor lysates receive Poly:ICLC as an adjuvant. As a positive control, a group of mice receive the inhibitors using Alzet pumps infusing the inhibitor at a constant concentration of 1 μg/μL at a rate of 0.5 μL/hr into the tumor environment. Experiments are performed as described above, and it is determined what are the effects of the novel inhibitors on: i) lymphocyte infiltration and caspase 3/7 activity, ii) development of immunological memory, and iii) survival.

A constant delivery system of novel inhibitor into the CNS maintaining an environment favorable for the immune system is developed. An adenovirus vector is generated that encodes selected inhibitor(s). The vectors used in this study are first generation, replication-deficient, recombinant adenovirus type 5 vectors (Ad), with deletions in the E1 and E3 regions. The expression cassette containing the transgene will be inserted within the E1 region (Southgate T, Kroeger K M, Liu C, Lowenstein P R, Castro M G. Gene transfer into neural cells in vitro using adenoviral vectors. Curr Protoc Neurosci 2008; Chapter 4: Unit 4 23). The Ad vector encoding the optimized inhibitor to be secreted into the tumor microenvironment is constructed, scaled up and purified. Transgene expression is under the control of the human CMV promoter (Curtin J F, King G D, Barcia C, et al. Fms-like tyrosine kinase 3 ligand recruits plasmacytoid dendritic cells to the brain. J Immunol 2006; 176(6): 3566-77; Ali S, King G D, Curtin J F, et al. Combined immunostimulation and conditional cytotoxic gene therapy provide long-term survival in a large glioma model. Cancer Res 2005; 65(16): 7194-204). All viral preparations is tested to be free of replication-competent adenovirus (RCA) and lipopolysaccharide (LPS) contamination using methodologies previously described (Puntel M, Kroeger K M, Sanderson N S, Thomas C E, Castro M G, Lowenstein P R. Gene transfer into rat brain using adenoviral vectors. Curr Protoc Neurosci 2010; Chapter 4: Unit 4 24; King G D, Muhammad A K, Curtin J F, et al. Flt3L and T K gene therapy eradicate multifocal glioma in a syngeneic glioblastoma model. Neuro Oncol 2008; 10(1): 19-31). The efficacy of Ads to express transgenes within the tumor microenvironment in rat and mouse intracranial, syngeneic GBM models has been extensively tested and validated. The present data indicate that using Ads delivered directly into the tumor mass, it is possible to achieve widespread and stable therapeutic transgene expression, elicit tumor regression and long-term anti-GBM immunological memory (Ghulam Muhammad A K, Candolfi M, King G D, et al. Antiglioma immunological memory in response to conditional cytotoxic/immune-stimulatory gene therapy: humoral and cellular immunity lead to tumor regression. Clin Cancer Res 2009; 15(19): 6113-27; Candolfi M, Yagiz K, Foulad D, et al. Release of HMGB1 in response to proapoptotic glioma killing strategies: efficacy and neurotoxicity. Clin Cancer Res 2009; 15(13): 4401-14; curtin J F, Liu N, Candolfi M, et al. HMGB1 mediates endogenous TLR2 activation and brain tumor regression. PLoS Med 2009; 6(1): e10; Curtin J F, Candolfi M, Fakhouri T M, et al. Treg depletion inhibits efficacy of cancer immunotherapy: implications for clinical trials. PLoS One 2008; 3(4): e1983).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reversing or modulating immune suppression in a patient having a cancer associated with overexpression of CD200, which method comprises administering to the patient in need thereof a composition comprising a CD200 inhibitor, wherein the CD200 inhibitor is a mutant of naturally-occurring CD200 peptide, wherein the CD200 inhibitor is 13 to 20 amino acids in length, and wherein the peptide comprises the amino acid sequence VTWQKKAAVSPEN (SEQ ID NO: 21).

2. The method of reversing or modulating immune suppression of claim 1, further comprising administering
   (i) a cancer vaccine;
   (ii) a cancer vaccine that is a tumor lysate; or
   (iii) a tumor lysate that is substantially devoid of CD200.

3. The method of reversing or modulating immune suppression of claim 1, wherein the composition further comprises a pharmaceutically acceptable carrier and/or diluent and/or an adjuvant.

4. The method of reversing or modulating immune suppression of claim 3, wherein the adjuvant is administered before, concurrently or after administration of composition.

5. The method of reversing or modulating immune suppression of claim 1, wherein the composition further comprises a cancer therapy.

6. The method of reversing or modulating immune suppression of claim 1, wherein the composition is administered at least twice, or wherein the administration comprises administering at least three doses of the composition, or the administration comprises administering at least five doses of the composition, or the administration comprises administering at least ten doses of the composition.

7. The method of reversing or modulating immune suppression of claim 6, wherein at least two consecutive dosages of the administration are separated by an interval of about one week, or wherein at least two consecutive dosages of the administration are separated by an interval of about one month.

8. A method of reversing or modulating immune suppression of claim 1, wherein the cancer is selected from glioblastoma, melanoma, prostate, endometrial, ovarian, breast, lung, head and neck, hepatocellular, thyroid, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia cancers.

9. The method of reversing or modulating immune suppression of claim 1, wherein the patient is a human.

10. The method of reversing or modulating immune suppression of claim 1, further comprising administering a chemotherapy agent.

11. The method of reversing or modulating immune suppression of claim 10, wherein the chemotherapy agent is sunititib, ontak, cyclophosphamide, gemcitabine, and/or retionoic acid.

12. A method of reversing or modulating immune suppression in a tumor microenvironment or sentinel lymph nodes in a patient having a cancer associated with overexpression of CD200, which method comprises administering to the patient in need thereof a composition of comprising a CD200 inhibitor, wherein the CD200 inhibitor is a mutant of naturally-occurring CD200 peptide, wherein the CD200 inhibitor is 13 to 20 amino acids in length, and wherein the peptide comprises the amino acid sequence VTWQKKAAVSPEN (SEQ ID NO: 21).

13. The method of reversing or modulating immune suppression in a tumor microenvironment or sentinel lymph nodes of claim 12, further comprising administering
   (i) a cancer vaccine;
   (ii) a cancer vaccine that is a tumor lysate; or
   (iii) a tumor lysate that is substantially devoid of CD200.

14. The method of reversing or modulating immune suppression in a tumor microenvironment or sentinel lymph nodes of claim 12, wherein the composition further comprises a pharmaceutically acceptable carrier and/or diluent and/or an adjuvant.

15. The method of reversing or modulating immune suppression in a tumor microenvironment or sentinel lymph nodes of claim 12, wherein the adjuvant is administered before, concurrently or after administration of composition.

16. The method of reversing or modulating immune suppression in a tumor microenvironment or sentinel lymph nodes of claim 12, wherein the composition further comprises a cancer therapy.

17. The method of reversing or modulating immune suppression in a tumor microenvironment or sentinel lymph nodes of claim 12, wherein the composition is administered at least twice, or wherein the administration comprises administering at least three doses of the composition, or the administration comprises administering at least five doses of the composition, or the administration comprises administering at least ten doses of the composition.

18. The method of reversing or modulating immune suppression in a tumor microenvironment or sentinel lymph nodes of claim 17, wherein at least two consecutive dosages of the administration are separated by an interval of about one week, or wherein at least two consecutive dosages of the administration are separated by an interval of about one month.

19. A method of reversing or modulating immune suppression in a tumor microenvironment or sentinel lymph nodes of claim 12, wherein the cancer is selected from glioblastoma, melanoma, prostate, endometrial, ovarian, breast, lung, head and neck, hepatocellular, thyroid, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia cancers.

20. The method of reversing or modulating immune suppression in a tumor microenvironment or sentinel lymph nodes of claim 12, wherein the patient is a human.

21. The method of reversing or modulating immune suppression in a tumor microenvironment or sentinel lymph nodes of claim 12, further comprising administering a chemotherapy agent.

22. The method of reversing or modulating immune suppression in a tumor microenvironment or sentinel lymph nodes of claim 12, wherein the chemotherapy agent is sunititib, ontak, cyclophosphamide, gemcitabine, and/or retionoic acid.

* * * * *